(12) United States Patent
Sanchez et al.

(10) Patent No.: US 11,690,595 B2
(45) Date of Patent: Jul. 4, 2023

(54) METHODS AND APPARATUSES FOR OFFLOADING ULTRASOUND DATA

(71) Applicant: BFLY Operations, Inc., Guilford, CT (US)

(72) Inventors: Nevada J. Sanchez, Guilford, CT (US); Graham Peyton, Madison, CT (US); Hamid Soleimani, Guilford, CT (US)

(73) Assignee: BFLY Operations, Inc, Burlington, MA (US)

( * ) Notice: Subject to any disclaimer, the term of this patent is extended or adjusted under 35 U.S.C. 154(b) by 743 days.

(21) Appl. No.: 16/379,093

(22) Filed: Apr. 9, 2019

(65) Prior Publication Data

US 2019/0343484 A1 Nov. 14, 2019

Related U.S. Application Data

(60) Provisional application No. 62/655,158, filed on Apr. 9, 2018.

(51) Int. Cl.
*A61B 8/00* (2006.01)
*G01S 7/52* (2006.01)
*G01S 15/89* (2006.01)

(52) U.S. Cl.
CPC .......... *A61B 8/4472* (2013.01); *A61B 8/4236* (2013.01); *A61B 8/56* (2013.01); *G01S 7/52017* (2013.01); *G01S 15/8906* (2013.01)

(58) Field of Classification Search
CPC .................................................. A61B 8/4472
See application file for complete search history.

(56) References Cited

U.S. PATENT DOCUMENTS

| 5,598,845 A | 2/1997 | Chandraratna et al. |
| 6,126,598 A * | 10/2000 | Entrekin ............. G01S 7/52025 600/437 |
| 6,780,154 B2 * | 8/2004 | Hunt ................... A61B 8/4427 600/446 |

(Continued)

FOREIGN PATENT DOCUMENTS

| WO | WO 2006/114735 A1 | 11/2006 |
| WO | WO 2010/020939 A2 | 2/2010 |

OTHER PUBLICATIONS

International Search Report and Written Opinion dated Jul. 1, 2019 in connection with International Application No. PCT/US2019/026505.

(Continued)

*Primary Examiner* — Joseph M Santos Rodriguez
(74) *Attorney, Agent, or Firm* — Boston & Galway, LLC

(57) ABSTRACT

Aspects of the technology described herein relate to wirelessly offloading, from a wearable ultrasound device, ultrasound data sufficient for forming one or more ultrasound images therefrom. The wearable ultrasound device may include an ultrasound patch. Indications that may be monitored with such a device, and therapeutic uses that may be provided by such a device, are also described. Methods and apparatuses are also described for compounding multilines of ultrasound data on an ultrasound device configured to collect the ultrasound data. Additionally, certain aspects of the technology relate to non-uniform grouping of ultrasound transducers that share a transmit/receive circuit in an ultrasound device.

23 Claims, 15 Drawing Sheets

(56) References Cited

U.S. PATENT DOCUMENTS

| | | | |
|---|---|---|---|
| 8,852,103 | B2 | 10/2014 | Rothberg et al. |
| 9,067,779 | B1 | 6/2015 | Rothberg et al. |
| 9,327,142 | B2 | 5/2016 | Rothberg et al. |
| 9,521,991 | B2 | 12/2016 | Rothberg et al. |
| 10,175,347 | B2 | 1/2019 | Chen et al. |
| 10,856,840 | B2 | 12/2020 | Rothberg et al. |
| 2002/0082500 | A1 | 6/2002 | Henderson et al. |
| 2005/0101865 | A1* | 5/2005 | Hao ............ G01S 7/52038 600/447 |
| 2005/0119574 | A1 | 6/2005 | Maerfeld et al. |
| 2006/0241454 | A1* | 10/2006 | Ustuner .......... G01S 7/5209 600/447 |
| 2006/0293596 | A1 | 12/2006 | Jago et al. |
| 2008/0208057 | A1 | 8/2008 | Hoctor et al. |
| 2009/0069693 | A1 | 3/2009 | Burcher et al. |
| 2009/0099456 | A1* | 4/2009 | Burcher .......... A61B 8/5276 600/459 |
| 2011/0055447 | A1 | 3/2011 | Costa |
| 2014/0180111 | A1 | 6/2014 | Gopinathan et al. |
| 2014/0276048 | A1 | 9/2014 | Kiley et al. |
| 2014/0288428 | A1 | 9/2014 | Rothberg et al. |
| 2015/0080724 | A1* | 3/2015 | Rothberg .......... G03B 27/52 600/439 |
| 2016/0104267 | A1 | 4/2016 | Hancock |
| 2017/0042507 | A1 | 2/2017 | Koning et al. |
| 2017/0105700 | A1 | 4/2017 | Bar-Zion et al. |
| 2017/0160388 | A1 | 6/2017 | Chen et al. |
| 2017/0258386 | A1 | 9/2017 | Woltjer et al. |
| 2017/0360397 | A1 | 12/2017 | Rothberg et al. |

OTHER PUBLICATIONS

[No Author Listed], NovioMini-Wearable bladder monitor. Meuleman Electronics. Retrieved from the internet https://meuleman.io/cases/noviomini-wearable-bladder-monitor/. Last accessed May 30, 2019; 7 pages.

Bhuyan et al. Miniaturized, wearable, ultrasound probe for on-demand ultrasound screening. Ultrasonics Symposium (IUS). 2011 IEE International. IEEE. 2011.

Tsakalakis et al., A wearable ultrasound multi-transducer array system for abdominal organs monitoring. Bioinformatics and Bioengineering (BIBE). 2013 IEEE 13$^{th}$ International Conference on. IEEE, 2013.

Van Leuteren et al., URIKA, continuous ultrasound monitoring for the detection of a full bladder in children with dysfunctional voiding: a feasibility study. Biomedical Physics & Engineering Express. Feb. 6, 2017; 3(1):017005.

International Preliminary Report on Patentability dated Oct. 22, 2020 in connection with International Application No. PCT/US2019/026505.

Adams et al., Multifollicular ovaries: clinical and endocrine features and response to pulsatile gonadotropin releasing hormone. The Lancet. Dec. 28, 1985;326(8469-8470):1375-79.

Ahuja et al., Ultrasound of malignant cervical lymph nodes. Cancer Imaging. 2008;8(1):48.

Arif et al., Noninvasive Diagnosis of Bladder Outlet Obstruction in Patients with Lower Urinary Tract Symptoms Using Ultrasound Decorrelation Analysis. The Journal of urology. Aug. 1, 2016;196(2):490-7.

Bateman et al., Measurement of gastric emptying by real-time ultrasound. Gut. Jun. 1, 1982;23(6):524-7.

Batzer et al., Landmarks during the first forty-two days of gestation demonstrated by the β-subunit of human chorionic gonadotropin and ultrasound. American journal of obstetrics and gynecology. Aug. 15, 1983;146(8):973-9.

Baumann et al., Estimation of central venous pressure by ultrasound. Resuscitation. Feb. 1, 2005;64(2):193-9.

Brennan et al., Handcarried ultrasound measurement of the inferior vena cava for assessment of intravascular volume status in the outpatient hemodialysis clinic. Clinical Journal of the American Society of Nephrology. Jul. 1, 2006;1(4):749-53.

Bright et al., Ultrasound estimated bladder weight and measurement of bladder wall thickness—useful noninvasive methods for assessing the lower urinary tract?.The Journal of urology. Nov. 1, 2010;184(5):1847-54.

Burov et al., Nonlinear ultrasound: Breakdown of microscopic biological structures and nonthermal impact on a malignant tumor. Doklady Biochemistry and Biophysics.Mar. 1, 2002;383(1-6):101-104.

Chandraratna et al., 'Hands-Free' Continuous Transthoracic Monitoring of Pericardiocentesis Using a Novel Ultrasound Transducer. Echocardiography. Aug. 2003;20(6):491-4.

Chen et al. Use of bedside ultrasound to assess degree of dehydration in children with gastroenteritis. Society for Academic Emergency Medicine. Oct. 2010; 17:1042-47.

Coussios et al., Role of acoustic cavitation in the delivery and monitoring of cancer treatment by high-intensity focused ultrasound (HIFU). International journal of hyperthermia. Jan. 1, 2007;23(2):105-20.

Creditt et al., Abdominal Aortic Aneurysm Ultrasound. Clinical Ultrasound. Springer. Cham. 2018; 135-147.

Curra et al., Therapeutic ultrasound: Surgery and drug delivery. Acoustical science and technology. 2003;24(6):343-8.

Darwiche et al., Measurement of gastric emptying by standardized real-time ultrasonography in healthy subjects and diabetic patients. Journal of Ultrasound in Medicine. Oct. 1999;18(10):673-82.

Delon-Martin et al., Venous thrombosis generation by means of high-intensity focused ultrasound. Ultrasound in medicine & biology. Jan. 1, 1995;21(1):113-9.

Denbow et al., Preclinical development of noninvasive vascular occlusion with focused ultrasonic surgery for fetal therapy, American journal of obstetrics and gynecology. Feb. 1, 2000;182(2):387-92.

Dicuio et al., Measurements of urinary bladder volume: comparison of five ultrasound calculation methods in volunteers. Arch Ital Urol Androl. Mar. 2005;77(1):60-2.

Enwemeka, The Effects of Therapeutic Ultrasound on Tendon Healing: A Biomechanical Study. American journal of physical medicine & rehabilitation. Dec. 1, 1989;68(6):283-7.

Finlay et al., Duplex and Color Doppler Sonography of hemodialysis arteriovenous fistulas and grafts. Radiographics. Sep. 1993;13(5):983-9.

Fornage et al., Clinical, mammographic, and sonographic determination of preoperative breast cancer size. Cancer. Aug. 15, 1987;60(4):765-71.

Franco et al., Ultrasound assessment of intravesical prostatic protrusion and detrusor wall thickness—new standards for noninvasive bladder outlet obstruction diagnosis?. The Journal of urology. Jun. 1, 2010;183(6):2270-4.

Garra, Tissue elasticity imaging using ultrasound. Applied radiology. Apr. 25, 2011;40(4):24.

Gelet et al., Transrectal high intensity focused ultrasound for the treatment of localized prostate cancer: factors influencing the outcome. European urology. 2001;40(2):124-9.

Gokhale, Ultrasound characterization of breast masses. The Indian journal of radiology & imaging. Aug. 2009;19(3):242.

Goldflam et al., Focus on: inferior vena cava ultrasound. ACEP Now. Jun. 2011;6:24-5.

Grajo et al., Compression elasticity imaging of the breast: an overview. Applied Radiology. Oct. 1, 2012;41(10):18.

Grondin et al., Real-time monitoring of high intensity focused ultrasound (HIFU) ablation of in vitro canine livers using harmonic motion imaging for focused ultrasound (HMIFU). Journal of Visualized Experiments. Nov. 3, 2015(105):1-7.

Gubler et al., Bedside sonographic control for positioning enteral feeding tubes: a controlled study in intensive care unit patients. Endoscopy. Dec. 2006;38(12):1256-60.

Gullace et al., Echocardiographic assessment of the inferior vena cava wall motion for studies of right heart dynamics and function. Clinical cardiology. Jul. 1984;7(7):393-404.

Hagen-Ansert, Textbook of Diagnostic Sonography, 8th Edition. Volume One. Elsevier, Inc. 2018.

(56) References Cited

OTHER PUBLICATIONS

Hagen-Ansert, Textbook of Diagnostic Sonography, 8th Edition. Volume Two. Elsevier, Inc. 2018.

Han et al., The diagnostic efficacy of 3-dimensional ultrasound estimated bladder weight corrected for body surface area as an alternative nonurodynamic parameter of bladder outlet obstruction. The Journal of urology. Mar. 1, 2011;185(3):964-9.

Haude et al., Continuous and Noninvasive Monitoring of Cardiac Output by Transesophageal Doppler Ultrasound. Transesophageal Echocardiography: A New Window to the Heart. 1989:260-6.

Husain et al., Sonographic diagnosis of pneumothorax. Journal of emergencies, trauma, and shock. Jan. 2012;5(1):76.

Hynynen et al., Noninvasive arterial occlusion using MRI-guided focused ultrasound. Ultrasound in medicine & biology. Jan. 1, 1996;22(8):1071-7.

Hynynen et al., Potential adverse effects of high-intensity focused ultrasound exposure on blood vessels in vivo. Ultrasound in medicine & biology. Jan. 1, 1996;22(2):193-201.

Ikee et al., Correlation between the resistive index by Doppler ultrasound and kidney function and histology. American Journal of Kidney Diseases. Oct. 1, 2005;46(4):603-9.

Indik et al., Association of umbilical venous with inferior vena cava blood flow velocities. Obstetrics & Gynecology. Apr. 1, 1991;77(4):551-7.

Jalaguier-Coudray et al., Solid masses: what are the underlying histopathological lesions?. Diagnostic and interventional imaging, Feb. 1, 2014;95(2):153-68,.

Keshavarzi et al., Treatment of uterine leiomyosarcoma in a xenograft nude mouse model using high-intensity focused ultrasound: a potential treatment modality for recurrent pelvic disease. Gynecologic oncology. Sep. 1, 2002;86(3):344-50.

Kessler et al., Ultrasound assessment of detrusor thickness in men—can it predict bladder outlet obstruction and replace pressure flow study?. The Journal of urology. Jun. 2006;175(6):2170-3.

Lee, Signal processing techniques for operator independent Doppler ultrasound: potential for use in transcranial Doppler ultrasound. MS Thesis, Ryerson University. 2011. 84 pages.

Lensing et al., Detection of deep-vein thrombosis by real-time B-mode ultrasonography. New England Journal of Medicine. Feb. 9, 1989;320(6):342-5.

Lichtenstein et al., A lung ultrasound sign allowing bedside distinction between pulmonary edema and COPD: the comet-tail artifact. Intensive care medicine. Dec. 1, 1998;24(12):1331-4.

Lin et al., Treatable domain and optimal frequency forbrain tumors during ultrasound hyperthermia. International Journal of Radiation Oncology* Biology* Physics. Jan. 1, 2000;46(1):239-47.

Lipton, Estimation of central venous pressure by ultrasound of the internal jugular vein. The American journal of emergency medicine. Jul. 1, 2000;18(4):432-4.

Luo et al., Pulse wave imaging of the human carotid artery: an in vivo feasibility study. IEEE transactions on ultrasonics, ferroelectrics, and frequency control .Jan. 30, 2012;59(1):132-81.

Magann et al., Ultrasound estimation of amniotic fluid vol. using the largest vertical pocket containing umbilical cord: measure to or through the cord?. Ultrasound in obstetrics & gynecology. Nov. 1, 2002;20(5):464-7.

Manieri et al., The diagnosis of bladder outlet obstruction in men by ultrasound measurement of bladder wall thickness. The Journal of urology. Mar. 1998;159(3):761-5.

Markert et al., Nonthermal ultrasound and exercise in skeletal muscle regeneration. Archives of physical medicine and rehabilitation. Jul. 1, 2005;86(7):1304-10.

Mencaglia, Energy focused ultrasound for the clinical treatment of uterine myoma. Ultrasound Med. Biol.. 2000;26:A207.

Milunsky et al., Genetic Disorders and the Fetus: Diagnosis. Prevention, and Treatment. Seventh Edition. John Wiley & Sons. Inc. 2016.

Mitragotri et al., Low-Frequency Sonophoresis: A Noninvasive Method of Drug Delivery and Diagnostics. Biotechnology progress. 2000;16(3):488-92.

Mitragotri et al., Transdermal delivery of heparin and low molecular weight heparin using low-frequency ultrasound. Pharmaceutical research. Aug. 1, 2001;18(8):1151-6.

Mitragotri et al., Ultrasound-mediated transdermal protein delivery. Science. Aug. 11, 1995;269(5225):850-3.

Mlosek et al., The use of high frequency ultrasound imaging in skin moisturization measurement. Skin Research and Technology. May 2013;19(2):169-75.

Modi et al., Accuracy of inferior vena cava ultrasound for predicting dehydration in children with acute diarrhea in resource-limited settings. PloS One. Jan. 14, 2016;11(1):1-12.

Nakashiki et al., Usefulness of a novel ultrasound transducer for continuous monitoring treadmill exercise echocardiography to assess coronary artery disease. Circulation Journal. 2006;70(10):1297-302.

Nedel et al., A simple and fast ultrasonographic method of detecting enteral feeding tube placement in mechanically ventilated, critically ill patients. Journal of Intensive Care. Dec. 2017;5(1):1-3.

Park et al., An innovative ultrasound technique for evaluation of tumor vascularity in breast cancers: superb micro-vascular imaging. Journal of Breast Cancer. Jun. 1, 2016;19(2):210-3.

Patrelli et al., Maternal hydration therapy improves the quantity of amniotic fluid and the pregnancy outcome in third-trimester isolated oligohydramnios: a controlled randomized institutional trial. Journal of Ultrasound in Medicine. Feb. 2012;31(2):239-44.

Payen et al., Ultrasonic strategies to monitor drug delivery. Journal of Drug Delivery Science and Technology. Jan. 1, 2013;23(1):47-56.

Pershad et al., Bedside limited echocardiography by the emergency physician is accurate during evaluation of the critically ill patient. Pediatrics. Dec. 1, 2004;114(6).

Petersen et al., The pulsatitity index and the resistive index in renal arteries. Associations with long-term progression in chronic renal failure. Nephrology, dialysis, transplantation: official publication of the European Dialysis and Transplant Association-European Renal Association. Jul. 1, 1997;12(7):1376-80.

Phelan et al., Amniotic fluid volume assessment with the four-quadrant technique at 36-42 weeks' gestation. Journal of Reproductive Medicine for the Obstetrician and Gynecologist. Jan. 1, 1987;32(7):540-2.

Phelan et al., Polyhydramnios and perinatal outcome. Journal of perinatology: official journal of the California Perinatal Association. Dec. 1990;10(4):347-50.

Pöhls et al., Fetal lung volumetry by three-dimensional ultrasound. Ultrasound in obstetrics & gynecology. Jan. 1998;11(1):6-12.

Prina et al., Lung ultrasound in the evaluation of pleural effusion. Jornal Brasileiro de Pneumologia. Feb. 2014;40(1):1-5.

Queenan et al., Ultrasound scanning of ovaries to detect ovulation in women. Fertility and sterility. Aug. 1, 1980;34(2):99-105.

Quiñones et al., A new, simplified and accurate method for determining ejection fraction with twodimensional echocardiography. Circulation. Oct. 1981;64(4):744-53.

Rakhmetova, Ultrasound Transducer Design for Continuous Fetal Heartbeat Monitoring, MS thesis, Høgskolen i Sørøst-Norge. Jul. 2016:103 pages.

Rantanen et al., Effects of therapeutic ultrasound on the regeneration of skeletal myofibers after experimental muscle injury. The American journal of sports medicine. Jan. 1999;27(1):54-9.

Rutherford et al., The four-quadrant assessment of amniotic fluid volume: an adjunct to antepartum fetal heart rate testing. Obstetrics and Gynecology. Sep. 1, 1987;70(3):353-6.

Schroeder et al., Role of power Doppler techniques and ultrasound contrast enhancement in the differential diagnosis of focal breast lesions. European radiology. Jan. 1, 2003;13(1):68-79.

Seo et al., Noninvasive arterial blood pressure waveform monitoring using two-element ultrasound system. IEEE transactions on ultrasonics, ferroelectrics, and frequency control. Apr. 14, 2015;62(4):776-84.

Tachibana, Transdermal delivery of insulin to alloxan-diabetic rabbits by ultrasound exposure. Pharmaceutical research. Jul. 1, 1992;9(7):952-4.

(56) References Cited

OTHER PUBLICATIONS

Takikawa et al. Low-intensity pulsed ultrasound initiates bone healing in rat nonunion fracture model. Journal of ultrasound in medicine. Mar. 2001;20(3):197-205.

Teodorescu et al., Duplex ultrasound evaluation of hemodialysis access: a detailed protocol. International journal of nephrology. Jan. 1, 2012;2012.

Uchida et al., Transrectal high intensity focused ultrasound for treatment of patients with stage T1b-2n0m0 localized prostate cancer: a preliminary report. Urology. Mar. 1, 2002;59(3):394-8.

Vaezy et al., Control of splenic bleeding by using high intensity Ultrasound. Journal of Trauma and Acute Care Surgery. Sep. 1, 1999;47(3):521-5.

Van Der Voort et al., Electrogastrography as a diagnostic tool for delayed gastric emptying in functional dyspepsia and irritable bowel syndrome. Neurogastroenterology & Motility. Oct. 2003;15(5):467-73.

Van Leuteren et al., URIKA, continuous ultrasound monitoring for the detection of a full bladder in children with dysfunctional voiding: a feasibility study. Biomedical Physics & Engineering Express. Feb. 6, 2017;3(1):8 pages.

Visioli et al., Preliminary results of a phase I dose escalation clinical trial using focused ultrasound in the treatment of localised tumours. European journal of ultrasound. Mar. 1, 1999;9(1):11-8.

Wang et al. Lung ultrasound: a promising tool to monitor ventilator-associated pneumonia in critically ill patients. Critical Care. Dec. 1, 2016;20(1):320.

Wei et al., Quantification of renal blood flow with contrast-enhanced ultrasound. Journal of the American College of Cardiology. Mar. 15, 2001;37(4):1135-40.

Wilkin et al., Influence of therapeutic ultrasound on skeletal muscle regeneration following blunt contusion. International journal of sports medicine. Jan. 2004;25(01):73-7.

Wladimiroff et al., Doppler ultrasound assessment of cerebral blood flow in the human fetus. BJOG: An International Journal of Obstetrics & Gynaecology. Apr. 1986;93(5):471-5.

Wu et al. Bedside ultrasound of the abdominal aorta clinical and practice management. ACEP Now. 2010.7 pages.

Wu et al., Pathological changes in human malignant carcinoma treated with high-intensity focused ultrasound. Ultrasound in medicine & biology. Aug. 1, 2001;27(8):1099-106.

Yen et al., Ultrasound stimulation of carotid baroreceptors: initial canine results. IEEE International Ultrasonics Symposium (IUS) Oct. 21, 2015:1-4.

Young et al., Effect of therapeutic ultrasound on the healing of full-thickness excised skin lesions. Ultrasonics. May 1, 1990;28(3):175-80.

EP19784407.9, Nov. 23, 2021, Extended European Search Report.
Extended European Search Report for European Application No. 19784407.9, dated Nov. 23, 2021.

\* cited by examiner

METHODS AND APPARATUSES FOR OFFLOADING ULTRASOUND DATA

CROSS-REFERENCE TO RELATED APPLICATIONS

The present application claims the benefit under 35 U.S.C. § 119(e) of U.S. Patent Application Ser. No. 62/655,158, filed Apr. 9, 2018 under B 1348.70072US00 and entitled "METHODS AND APPARATUSES FOR OFFLOADING ULTRASOUND DATA," which is hereby incorporated herein by reference in its entirety.

FIELD

Generally, the aspects of the technology described herein relate to ultrasound devices. Some aspects relate to offloading of ultrasound data from ultrasound devices.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using a probe), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

Aspects of this disclosure relate to wearable ultrasound devices, such as methods for offloading ultrasound images from a wearable ultrasound device, circuit architectures for reducing the size of a wearable ultrasound device, various indications that may be monitored through ultrasound images offloaded from a wearable ultrasound device, and various therapies that a wearable ultrasound device may deliver.

According to one aspect, a method includes wirelessly offloading, from a wearable ultrasound device, ultrasound data sufficient for forming one or more ultrasound images therefrom. In some embodiments, the one or more ultrasound images include information indicative of a size or shape of a tumor. In some embodiments, the one or more ultrasound images include information indicative of an elasticity of a tumor. In some embodiments, the one or more ultrasound images include information indicative of a vascularity of a tumor. In some embodiments, the one or more ultrasound images include information indicative of a fullness or a volume of a bladder. In some embodiments, the one or more ultrasound images include information indicative of a bladder outlet obstruction.

In some embodiments, the one or more ultrasound images include information indicative of a pulse wave velocity or a blood pressure. In some embodiments, the one or more ultrasound images include information indicative of a diameter of a blood vessel. In some embodiments, the one or more ultrasound images include information indicative of a volume of a blood vessel. In some embodiments, the one or more ultrasound images include information indicative of a collapsibility of a blood vessel. (IVC collapsibility may be calculated by measuring maximum IVC diameter ($IVC_{max}$) and minimum IVC diameter ($IVC_{min}$) and calculating IVC collapsibility as ($IVC_{max}$-$IVC_{min}$)/$IVC_{max}$×100.) In some embodiments, the one or more ultrasound images include information indicative of a blood flow rate through a blood vessel. In some embodiments, the one or more ultrasound images include information indicative of a wall motion of a blood vessel. In some embodiments, the blood vessel is an inferior vena cava. In some embodiments, the one or more ultrasound images include information indicative of an intravascular volume.

In some embodiments, the one or more ultrasound images include information indicative of a left ventricular wall motion. In some embodiments, the one or more ultrasound images include information indicative of a cardiac output. In some embodiments, the one or more ultrasound images include information indicative of a cardiac ejection fraction. In some embodiments, the one or more ultrasound images include information indicative of a central venous pressure. In some embodiments, the one or more ultrasound images include information indicative of a peripheral blood flow rate.

In some embodiments, the one or more ultrasound images include information indicative of an abdominal aortic aneurysm. In some embodiments, the one or more ultrasound images include information indicative of a deep vein thrombosis. In some embodiments, the one or more ultrasound images include information indicative of a fetal heartbeat. In some embodiments, the one or more ultrasound images include information indicative of a pregnancy. In some embodiments, the one or more ultrasound images include information indicative of a follicle growth in ovaries. In some embodiments, the one or more ultrasound images include information indicative of dehydration. In some embodiments, the one or more ultrasound images include information indicative of a skin moisturization. In some embodiments, the one or more ultrasound images include information indicative of an amniotic fluid volume.

In some embodiments, the one or more ultrasound images include information indicative of pneumonia. In some embodiments, the one or more ultrasound images include information indicative of a pleural effusion. In some embodiments, the one or more ultrasound images include information indicative of pneumothorax. In some embodiments, the one or more ultrasound images include information indicative of chronic obstructive pulmonary disease (COPD). In some embodiments, the one or more ultrasound images include information indicative of a lung volume.

In some embodiments, the one or more ultrasound images include information indicative of an enteral feeding tube placement. In some embodiments, the one or more ultrasound images include information indicative of a gastric emptying. In some embodiments, the one or more ultrasound images include information indicative of indigestion. In some embodiments, the one or more ultrasound images include information indicative of a kidney function. In some embodiments, the one or more ultrasound images include information indicative of a renal blood flow rate.

In some embodiments, the one or more ultrasound images include information indicative of a needle placement during pericardiocentesis. In some embodiments, the one or more ultrasound images include information indicative of a needle placement during amniocentesis. In some embodiments, the one or more ultrasound images include information indicative of a vasospasm. In some embodiments, the one or more ultrasound images include information indicative of a high-intensity focused ultrasound ablation. In some embodiments, the one or more ultrasound images include information indicative of a drug delivery. In some embodiments, the one or more ultrasound images include information indicative of a hemodialysis access.

According to another aspect, a method includes insonating, for a therapeutic purpose, by a wearable ultrasound device, a subject wearing the wearable ultrasound device. In some embodiments, insonating, for the therapeutic purpose, the subject wearing the wearable ultrasound device includes insonating a carotid baroreceptor of the subject. In some embodiments, insonating, for the therapeutic purpose, the subject wearing the wearable ultrasound device includes insonating a muscle of the subject. In some embodiments, insonating, for the therapeutic purpose, the subject wearing the wearable ultrasound device includes insonating a tendon of the subject. In some embodiments, insonating, for the therapeutic purpose, the subject wearing the wearable ultrasound device includes insonating a skin portion of the subject. In some embodiments, insonating, for the therapeutic purpose, the subject wearing the wearable ultrasound device includes insonating a bone of the subject. In some embodiments, insonating, for the therapeutic purpose, the subject wearing the wearable ultrasound device includes delivering high-intensity focused ultrasound (HIFU)-based cancer treatment. In some embodiments, insonating, for the therapeutic purpose, the subject wearing the wearable ultrasound device includes delivering HIFU-based therapy that includes occlusion of a blood vessel. In some embodiments, insonating, for the therapeutic purpose, the subject wearing the wearable ultrasound device includes delivering HIFU-based therapy for augmentation of a subject's immune response. In some embodiments, insonating, for the therapeutic purpose, the subject wearing the wearable ultrasound device includes facilitating drug delivery.

According to another aspect, a method includes compounding multilines (a.k.a. A-lines) of ultrasound data on an ultrasound device configured to collect the ultrasound data. As referred to herein, a multiline should be understood to mean a set of datapoints representing ultrasound scattering locations in space, where at least one datapoint of the multiline is formed from a combination of measurements from two or more ultrasound transducers such that the measurements from the two or more ultrasound transducers are calculated to be coming from the same spatial location.

In some embodiments, compounding the multilines of the ultrasound data comprises: collecting, by the ultrasound device, N first multilines of the ultrasound data following a first ultrasound transmit event; collecting, by the ultrasound device, N second multilines of the ultrasound data following a second ultrasound transmit event that is subsequent to the first ultrasound transmit event; and compounding, on the ultrasound device, N−p of the first multilines and N−p of the second multilines, wherein p is a pitch factor of the first and second multilines of ultrasound data and is less than N. In some embodiments, compounding comprises incoherent compounding. In some embodiments, compounding comprises coherent compounding.

In some embodiments, the method further comprises offloading from the ultrasound device, following the first ultrasound transmit event, p multilines of the first multilines. In some embodiments, the method further comprises truncating the p multilines of the first multilines to 12 bits prior to offloading. In some embodiments, the method further comprises truncating the p multilines of the first multilines to 10 bits prior to offloading. In some embodiments, the p multilines of the first multilines do not overlap with any of the second multilines. In some embodiments, the N−p multilines of the first multilines and the N−p multilines of the second multilines overlap.

In some embodiments, the method further comprises offloading from the ultrasound device, following the second ultrasound transmit event, p multilines of the first multilines compounded with p multilines of the second multilines. In some embodiments, the method further comprises truncating the p multilines of the first multilines compounded with the p multilines of the second multilines to 12 bits prior to offloading. In some embodiments, the method further comprises truncating the p multilines of the first multilines compounded with the p multilines of the second multilines to 10 bits prior to offloading.

In some embodiments, N is between 2-32 and p is between 1-8. In some embodiments, the ultrasound device comprises digital circuitry having configurable bit depth. In some embodiments, compounding the multilines of the ultrasound data on the ultrasound device comprises compounding the multilines of the ultrasound data on a field-programmable gate array (FPGA) on the ultrasound device. In some embodiments, compounding the multilines of the ultrasound data on the ultrasound device comprises compounding the multilines of the ultrasound data on an application-specific integrated circuit (ASIC) on the ultrasound device. In some embodiments, compounding the multilines of the ultrasound data on the ultrasound device comprises compounding the multilines of the ultrasound data on an ultrasound-on-a-chip on the ultrasound device.

According to another aspect, a method for collecting ultrasound data on an ultrasound device, the ultrasound device having a memory buffer, comprises: collecting N multilines of ultrasound data following an ultrasound transmit event; and updating data at addresses 1 to N of the memory buffer by compounding data at addresses ((p×i) modulo N)+1 to ((p×i+N−p−1) modulo N)+1 of the memory buffer with multilines 1 to N−p of the N multilines; and overwriting data at addresses ((p×i+N−p) modulo N)+1 to ((p×i+N−1) modulo N)+1 of the memory buffer with multilines N−p+1 to N of the N multilines; wherein: p comprises a pitch factor of multilines collected by the ultrasound device following successive ultrasound transmit events; and i comprises a counter variable.

In some embodiments, compounding comprises incoherent compounding. In some embodiments, compounding comprises coherent compounding. In some embodiments, the method further comprises, prior to updating the data at the addresses 1 to N of the memory buffer, storing at the addresses 1 to N of the memory buffer multilines of ultrasound data collected following one or more ultrasound transmit events prior to the ultrasound transmit event.

In some embodiments, the method further comprises offloading data at addresses ((p×i) modulo N)+1 to ((p×i+p−1) modulo N)+1 of the memory buffer from the ultrasound device. In some embodiments, the method further comprises truncating the data at addresses 1 to p of the memory buffer to 12 bits prior to offloading. In some embodiments, the method further comprises truncating the data at addresses 1 to p of the memory buffer to 10 bits prior to offloading. In some embodiments, the method further comprises incrementing i by 1 after offloading the data at addresses 1 to p of the memory buffer. In some embodiments, N is between 2-32 and p is between 1-8. In some embodiments, the ultrasound device comprises digital circuitry having configurable bit depth.

According to another method, a method for collecting ultrasound data on an ultrasound device, the ultrasound device having a memory buffer, comprises: collecting N multilines of ultrasound data following an ultrasound transmit event; and updating data at addresses 1 to N of the memory buffer by compounding data at addresses 1 to N−p of the memory buffer with multilines 1 to N−p of the N multilines; and overwriting data at addresses N−p+1 to N of the memory buffer with multilines N−p+1 to N of the N multilines; wherein p comprises a pitch factor of multilines collected by the ultrasound device following successive ultrasound transmit events.

In some embodiments, compounding comprises incoherent compounding. In some embodiments, compounding comprises coherent compounding. In some embodiments, the method further comprises, prior to updating the data at the addresses 1 to N of the memory buffer, storing at the addresses 1 to N of the memory buffer multilines of ultrasound data collected following one or more ultrasound transmit events prior to the ultrasound transmit event.

In some embodiments, the method further comprises offloading the data at addresses 1 to p of the memory buffer from the ultrasound device. In some embodiments, the method further comprises truncating the data at addresses 1 to p of the memory buffer to 12 bits prior to offloading. In some embodiments, the method further comprises truncating the data at addresses 1 to p of the memory buffer to 10 bits prior to offloading. In some embodiments, the method further comprises moving the data at addresses p+1 to N of the memory buffer to addresses 1 to N−p of the memory buffer. In some embodiments, N is between 2-32 and p is between 1-8. In some embodiments, the ultrasound device comprises digital circuitry having configurable bit depth.

Some aspects include an ultrasound device configured to perform the above aspects and embodiments. In some embodiments of any of the aspects described herein, offloading is performed wirelessly. In some embodiments of any of the aspects described herein, wireless offloading is performed at a data rate within a range of approximately 10 megabits/second-1.73 gigabits/second. In some embodiments of any of the aspects described herein, wireless offloading is performed at a data rate within a range of approximately 10 megabits/second-1.73 gigabits/second. In some embodiments of any of the aspects described herein, wireless offloading is performed at a data rate within a range of approximately 10-866.7 megabits/second. In some embodiments of any of the aspects described herein, wireless offloading is performed at a data rate within a range of approximately 10-450 megabits/second. In some embodiments of any of the aspects described herein, wireless offloading is performed at a data rate within a range of approximately 10-100 megabits/second. In some embodiments of any of the aspects described herein, wireless offloading is performed at a data rate within a range of approximately 10-72 megabits/second. In some embodiments of any of the aspects described herein, wireless offloading is performed at a data rate within a range of approximately 10-54 megabits/second. In some embodiments of any of the aspects described herein, wireless offloading is performed at a data rate within a range of approximately 10-32 megabits/second. In some embodiments of any of the aspects described herein, wireless offloading is performed using a communication platform employing an IEEE 802.11 standard.

According to another aspect, an apparatus comprises an ultrasound device, the ultrasound device comprising a first group of ultrasound transducers, a second group of ultrasound transducers, a first transmit/receive circuit electrically coupled to the first group of ultrasound transducers, and a second transmit/receive circuit electrically coupled to the second group of ultrasound transducers, wherein the first group of ultrasound transducers comprises a greater number of ultrasound transducers than the second group of ultrasound transducers.

In some embodiments, the first group of ultrasound transducers and the second group of ultrasound transducers are disposed in a single column of an array of ultrasound transducers. In some embodiments, the single column is disposed along an elevational direction of the array of ultrasound transducers. In some embodiments, the first group of ultrasound transducers is disposed further towards to the center of the column than the second group of ultrasound transducers. In some embodiments, each group of ultrasound transducers in the column that is coupled to a single transmit/receive circuit contains fewer or an equal number of ultrasound transducers than every other group of ultrasound transducers that is coupled to a single transmit/receive and is disposed further towards the center of the column.

In some embodiments, the array of ultrasound transducers comprises a 1.75-dimensional array. In some embodiments, the first transmit/receive circuit and the second transmit/receive circuit each comprise a receive amplifier, a pulser, and a switch. In some embodiments, the column comprises 32 ultrasound transducers grouped into 11 groups of ultrasound transducers each electrically coupled to a single transmit/receive circuit.

In some embodiments of any of the aspects described herein, the wearable ultrasound device includes an ultrasound patch. In some embodiments, the wearable ultrasound device weighs no more than 4 lbs. In some embodiments, the wearable ultrasound device weighs no more than 2 lbs. In some embodiments, a volume of the wearable ultrasound device is no greater than 250 cm$^3$. In some embodiments, a volume of the wearable ultrasound device is no greater than 125 cm$^3$. In some embodiments, a volume of the wearable ultrasound device is no greater than 50 cm$^3$. In some embodiments, the wearable ultrasound device includes a two-dimensional array of ultrasound transducers. In some embodiments, the wearable ultrasound device includes a 1.75-dimensional array of ultrasound transducers. In some embodiments, a height of the wearable ultrasound device along a direction orthogonal to the array of ultrasound transducers is no greater than 7 cm. In some embodiments, a height of the wearable ultrasound device along a direction orthogonal to the array of ultrasound transducers is no greater than 5 cm. In some embodiments, a height of the wearable ultrasound device along a direction orthogonal to the array of ultrasound transducers is no greater than a dimension of the array of ultrasound transducers. In some embodiments, the ultrasound device includes between approximately 5 kilobytes and 20 megabytes of memory.

BRIEF DESCRIPTION OF THE DRAWINGS

Various aspects and embodiments will be described with reference to the following exemplary and non-limiting fig

DETAILED DESCRIPTION

Figure 1:
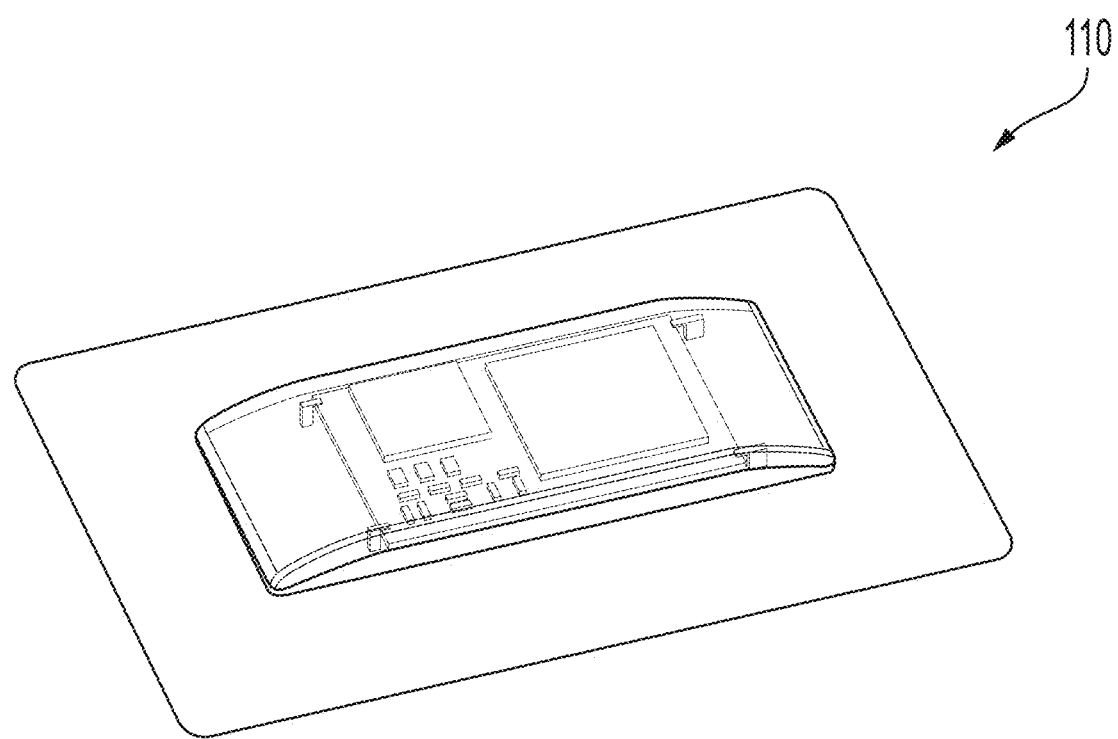
- FIG. 1 illustrates an ultrasound patch in accordance with certain embodiments described herein.

Conventional ultrasound systems are large, complex, and expensive systems that are typically only purchased by large medical facilities with significant financial resources. Recently, cheaper and less complex ultrasound imaging devices have been introduced. Such imaging devices may include ultrasound transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety. The reduced cost and increased portability of these new ultrasound devices may make them significantly more accessible to the general public than conventional ultrasound devices. Furthermore, the portability of these new ultrasound devices makes them suitable for incorporation into wearable devices, such as ultrasound patches, that can collect ultrasound data.

Imaging a subject using an ultrasound patch that adheres to the subject, rather than using a conventional ultrasound probe, may be helpful for a number of reasons. An ultrasound patch may remain adhered to a patient and may therefore allow for easier continuous imaging and monitoring with ultrasound than monitoring with a probe, which requires another individual to constantly hold the probe on the patient. Continuous monitoring may be helpful in cases where real-time, continuous information from ultrasound imaging is required, as opposed to after-the-fact or periodic information. In a similar vein, because the ultrasound patch may remain adhered to a subject for an extended period of time, the ultrasound patch may be used for long-term imaging and monitoring with ultrasound. Long-term monitoring may refer to any period of time that is longer than a conventional ultrasound imaging session with a conventional ultrasound probe, and may be minutes, hours, days, weeks, months, or years, as examples. Long-term monitoring may be useful in cases where it is not known when a particular event (e.g., an adverse physiological event) may occur. Furthermore, the ultrasound patch may collect data from a subject outside of a medical setting, such as in the subject's home.

The inventors have also recognized that it may be helpful for wearable ultrasound devices (such as ultrasound patches) to wirelessly offload to an auxiliary electronic device ultrasound data sufficient to construct an ultrasound image therefrom. Wireless offloading of ultrasound data from the ultrasound device may allow the ultrasound device to offload data while the patient wearing the ultrasound device performs routine activities. In other words, the patient wearing the ultrasound device need not be tethered, by a wired connection, to another auxiliary device to which the ultrasound device offloads data. In contrast to transmitting an alarm signal or metric automatically generated by an ultrasound device based on collected ultrasound data, offloading data sufficient to construct an ultrasound image therefrom may be helpful because an ultrasound image may provide more information than a transmitted alarm signal or metric, and because this may allow a medical professional to view the ultrasound image. For example, ultrasound data may contain an unexpected indication that an ultrasound device may not be programmed to automatically detect. By offloading data sufficient to construct a full ultrasound image, a medical professional may be able to detect the unexpected indication upon viewing the ultrasound image. Additionally, a medical professional may need to monitor ultrasound images over an extended time period to confirm a diagnosis or other assessment of a patient. Offloading ultrasound images over an extended time period may facilitate this monitoring. In addition to, or instead of, a medical professional analyzing offloaded images, a deep learning model may analyze ultrasound images to produce results (e.g., anatomical or physiological measurements).=The ultrasound device may perform continuous and/or long-term monitoring of medical indications by wirelessly offloading ultrasound data sufficient to construct an ultrasound image therefrom.

However, wirelessly offloading data sufficient to construct an ultrasound image therefrom may be difficult because the rate of data produced by an ultrasound device may exceed the data offload rate capabilities of wireless communication platforms. The inventors have recognized that the data offload rate from the ultrasound device may be reduced by implementing compounding of multilines of ultrasound data on the ultrasound device that collects the ultrasound data, rather than on an auxiliary electronic device to which the ultrasound device offloads ultrasound data. In particular, if p is the pitch factor of the multilines of ultrasound data, and N multilines are collected per ultrasound transmit event, the rate of data offloading from the ultrasound device may be reduced by a factor of p/N. As referred to herein, $N \geq 1$, $p \geq 1$, and $p < N$.

The inventors have further recognized that it may be helpful for the transducers of the ultrasound device to be arranged in a 1.75-dimensional (1.75d) array. In a 1.75d array, groups of transducers in the elevation direction (e.g., groups of transducers along a column in the transducer array) can be independently controlled to allow for limited steering of ultrasound beams in the elevation direction. Steering in the elevation direction may be helpful for an ultrasound patch because it may enable acquiring ultrasound images from different elevational planes without needing to detach the ultrasound patch from the position and orientation at which the ultrasound patch was adhered to the subject. For example, upon adhering the ultrasound patch to a subject's abdomen, it may be possible to use elevational steering to ensure that data is collected between the subject's ribs.

The inventors have further recognized that it may be helpful for groups of transducers to share a transmit/receive circuit (e.g., a pulser and a receive amplifier), rather than each transducer having its own transmit/receive circuit, in order to reduce the size of the ultrasound device. Furthermore, the inventors have recognized that it may be helpful for the number of transducers in each group of transducers that share a transmit/receive circuit to be non-uniform. In particular, one group of transducers in a column sharing a transmit/receive circuit may have a different number of transducers than another group of transducers sharing a transmit/receive circuit. For example, each group of transducers within a given column of the transducer array may contain fewer or an equal number of transducers compared with other groups of transducers located further towards the center of the column. This may be helpful because certain ultrasound beam profiles require that delays implemented at transducers located towards the ends of a column be larger delays than delays implemented at transducers located towards the center of a column. Therefore, it may be helpful to more tightly control delays at transducers located towards the ends of a column by grouping together smaller numbers of such transducers than with respect to transducers located towards the center of a column.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 2:
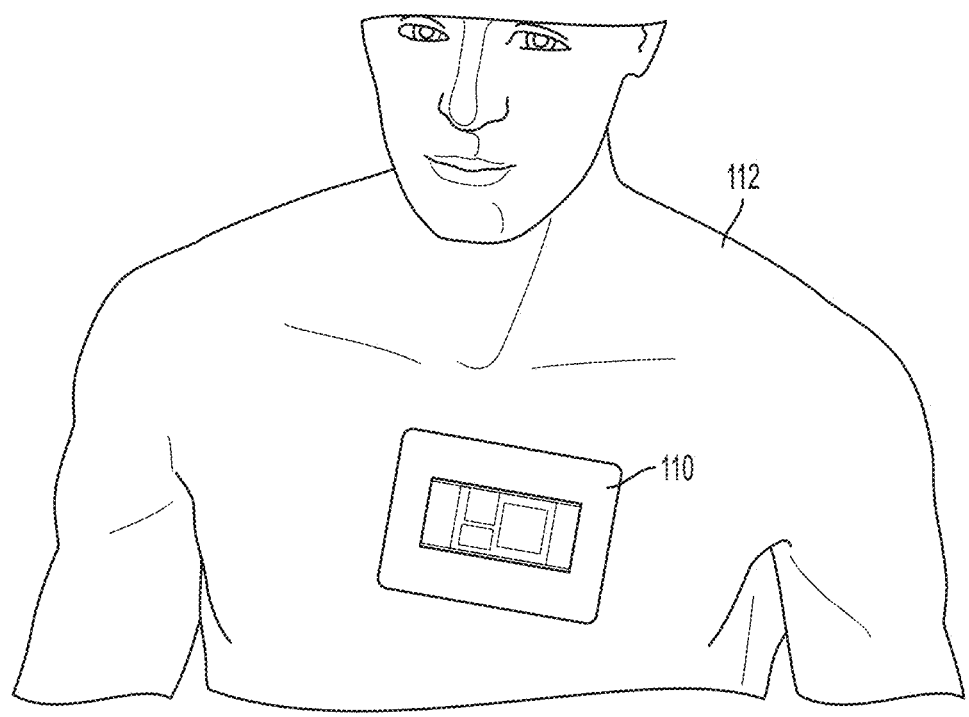
FIG. 2 illustrates the ultrasound patch coupled to a patient in accordance with certain embodiments described herein.

In some embodiments, a wearable ultrasound device may be embodied in an ultrasound patch that may be coupled to a patient. For example, FIG. 1 illustrates an ultrasound patch 110 and FIG. 2 illustrates the ultrasound patch 110 coupled to a patient 112 (FIG. 2) in accordance with certain embodiments described herein. The ultrasound patch 110 may be configured to offload, for example wirelessly, data collected by the ultrasound patch 110 to one or more external auxiliary devices (not shown) for further processing. For purposes of illustration, a to p housing of the ultrasound patch 110 is depicted in a transparent manner to depict exemplary locations of various internal components of the ultrasound patch.

Figure 3:
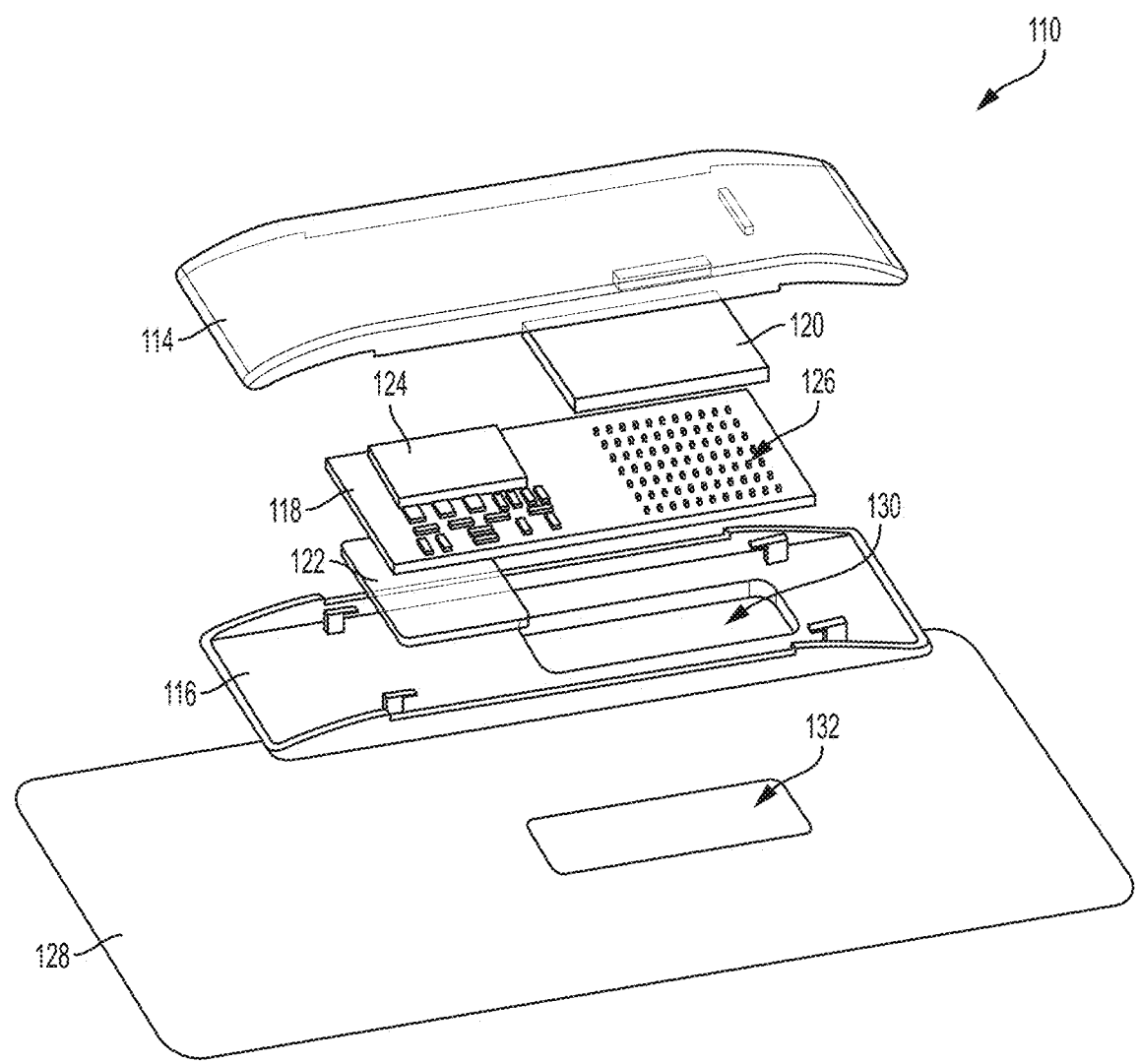
FIGS. 3 and 4 show exploded views of the ultrasound patch in accordance with certain embodiments described herein.
Figure 4:
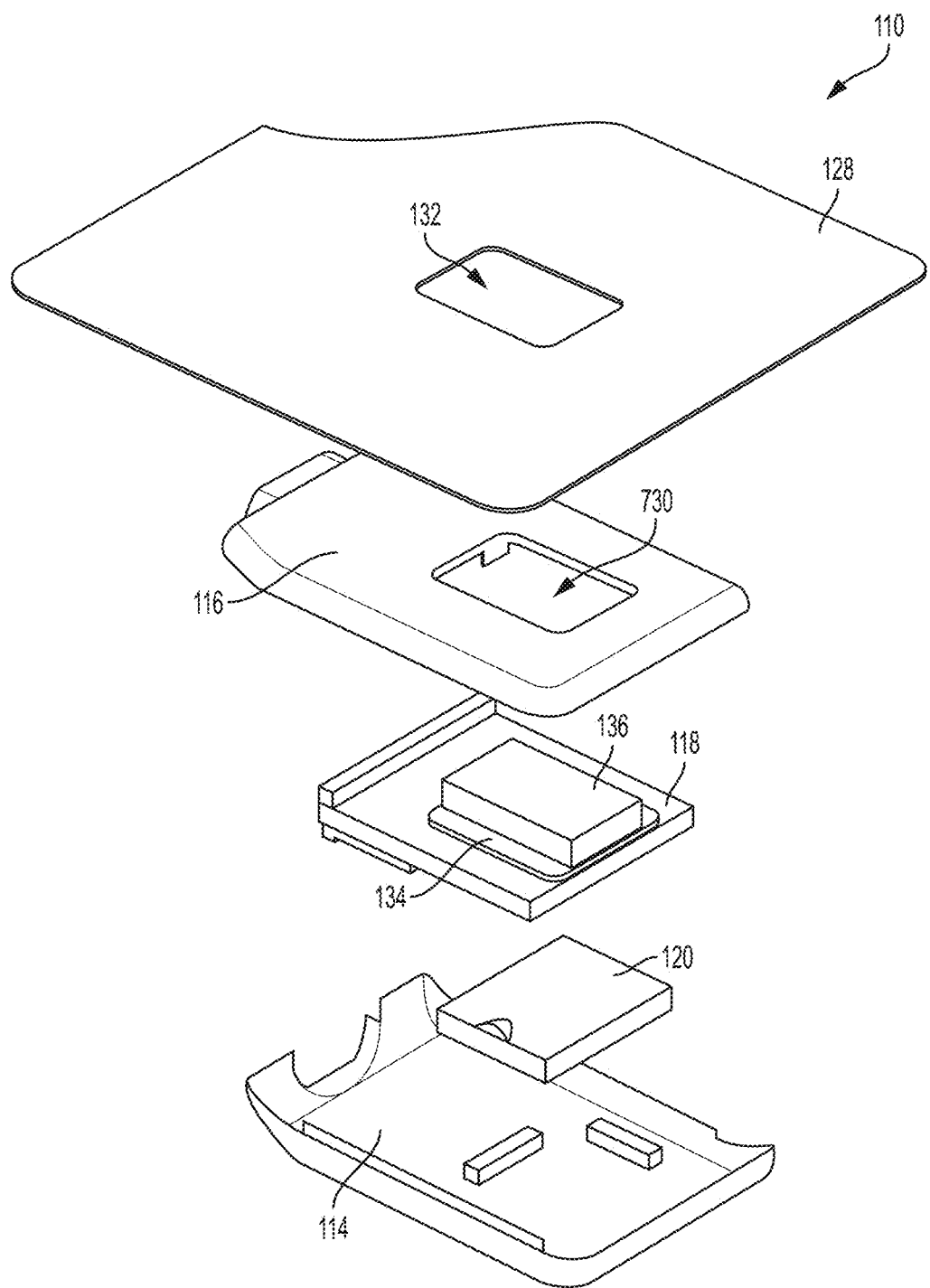

FIGS. 3 and 4 show exploded views of the ultrasound patch 110 in accordance with certain embodiments described herein. As particularly illustrated in FIG. 3, the ultrasound patch 110 includes an upper housing 114, a lower housing 116, and a circuit board 118. The circuit board 118 may be configured to support various components, such as for example a heat sink 120, a battery 122, and communications circuitry 124. In one embodiment, the communication circuitry 124 includes one or more short- or long-range communication platforms. Exemplary short-range communication platforms include Bluetooth (BT), Bluetooth Low Energy (BLE), and Near-Field Communication (NFC). Exemplary long-range communication platforms include WiFi and Cellular. While not shown, the communication circuitry 124 may include front-end radio, antenna and other processing circuitry configured to communicate radio signal to an external auxiliary electronic device (not shown). The radio signal may include ultrasound imaging information obtained by the ultrasound patch 110. In an exemplary embodiment, the communication platform transmits periodic beacon signals according to IEEE 802.11 and other prevailing standards. The beacon signal may include a BLE advertisement. Upon receipt of the beacon signal or the BLE advertisement, an external auxiliary device (not shown) may respond to the ultrasound patch 110. That is, the response to the beacon signal may initiate a communication handshake between the ultrasound patch 110 and the auxiliary device. The auxiliary device may include a lapto p computer, a deskto p computer, a smartphone, a tablet device, or any other device configured for wireless communication. The auxiliary device may act as a gateway to cloud or internet communication. In an exemplary embodiment, the auxiliary device may include the patient's own smart device (e.g., smartphone) which communicatively couples to the ultrasound patch 110 and periodically receives ultrasound information from the ultrasound patch 110. The auxiliary device may then communicate the received ultrasound information to external sources. In some embodiments, the ultrasound patch 110 may offload ultrasound information to the auxiliary device in real-time.

The circuit board 118 may include processing circuitry, including one or more controllers and/or field-programmable gate arrays (FPGAs) to direct communication through the communication circuitry 124. For example, the circuit board 118 may engage the communication circuitry 124 periodically or on as-needed basis to communicate information with one or more auxiliary devices. Ultrasound information may include signals and information defining an ultrasound image captured by the ultrasound patch 110. Ultrasound information may also include control parameters communicated from the auxiliary device to the ultrasound patch 110. The control parameters may dictate the scope of the ultrasound data/image to be obtained by ultrasound patch 110.

In one embodiment, the auxiliary device may store ultrasound information received from the ultrasound patch 110. In another embodiment, the auxiliary device may relay ultrasound information received from the ultrasound patch 110 to another station. For example, the auxiliary device may use WiFi to communicate the ultrasound information received from the ultrasound patch 110 to a cloud-based server. The cloud-based server may be a hospital server or a server accessible to the physician directing ultrasound imaging. In another exemplary embodiment, the ultrasound patch 110 may send sufficient ultrasound information to the auxiliary device such that the auxiliary device may construct an ultrasound image therefrom. In this manner, communication bandwidth and power consumption may be minimized at the ultrasound patch 110.

In still another embodiment, the auxiliary device may engage the ultrasound patch 110 through radio communication (i.e., through the communication circuitry 124) to actively direct operation of the ultrasound patch 110. For example, the auxiliary device may direct the ultrasound patch 110 to produce ultrasound data from the patient at periodic intervals. The auxiliary device may direct the depth of the ultrasound images taken by the ultrasound patch 110. In still another example, the auxiliary device may control the manner of operation of the ultrasound patch 110 so as to preserve power consumption at the battery 122. Upon receipt of ultrasound information from the ultrasound patch 110, the auxiliary device may operate to cease imaging, increase imaging rate or communicate an alarm to the patient or to a third party (e.g., physician or emergency personnel).

As shown in FIG. 3, a plurality of through vias 126 (e.g., copper) may be used for a thermal connection between the heat sink 120 and one or more CMOS chips (not shown in FIG. 3). For example, the CMOS chip may be an application-specific integrated circuit (ASIC). The ASIC may be part of an ultrasound-on-a-chip (i.e., a device including micromachined ultrasound transducers integrated with an ASIC or other semiconductor die containing integrated circuitry). As further depicted in FIG. 3, the ultrasound patch 110 may also include a dressing 128 that provides an adhesive surface for both the ultrasound patch housing as well as to the skin of a patient. One non-limiting example of such a dressing 128 is Tegaderm™, a transparent medical dressing available from 3M Corporation. A lower housing 116 includes a generally rectangular shaped opening 130 that aligns with another opening 132 in the dressing 128.

Referring to FIG. 4, another "bottom up" exploded view of the ultrasound patch 110 illustrates the location of ultrasonic transducers and integrated CMOS chip (generally indicated by 134) on the circuit board 118. An acoustic lens 136 mounted over the transducers/CMOS chip 134 is configured to protrude through openings 130 and 132 to make contact with the skin of a patient. In some embodiments, the ultrasonic transducers may be arranged in a two-dimensional array. In some embodiments, the ultrasonic transducers may be arranged in a 1.75-dimensional array (as described further below).

Figure 5:
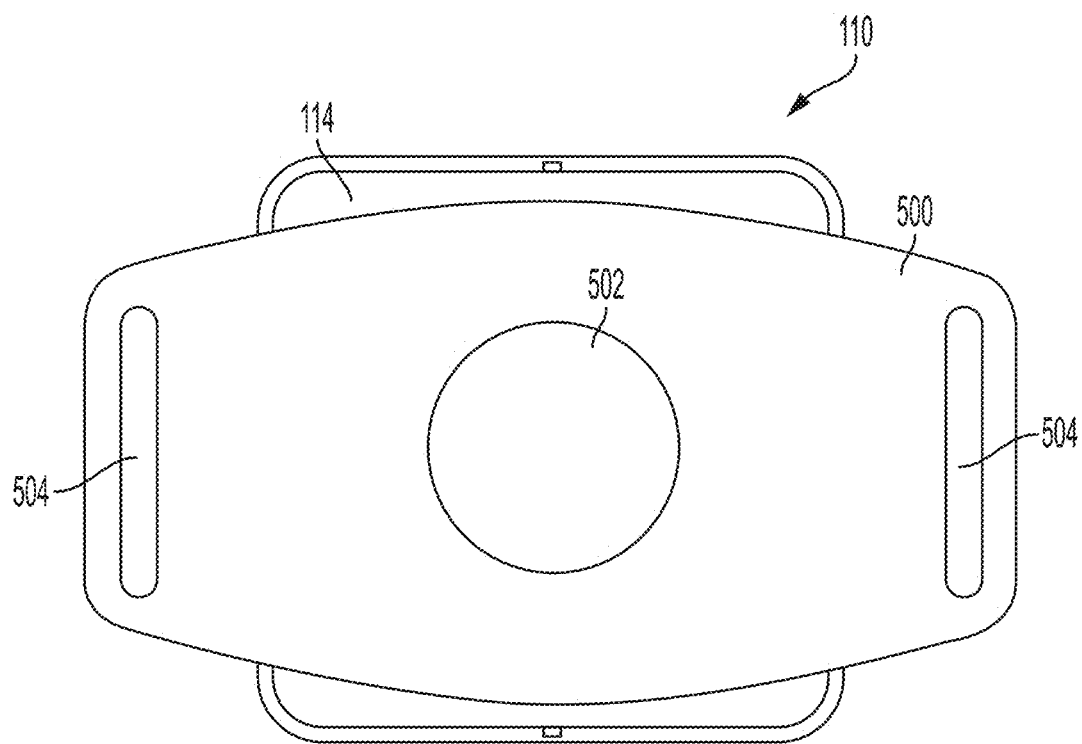
FIG. 5 shows an alternative fastening mechanism for the ultrasound patch in accordance with certain embodiments described herein.

Referring to FIG. 5, an alternative fastening mechanism for the ultrasound patch 110 in accordance with certain embodiments described herein is illustrated. In the embodiment shown, the ultrasound patch 110 further includes a buckle 500 affixed to the upper housing 114 via a post 502 using, for example, a threaded engagement between the buckle 500 and the post 502. Other attachment configurations are also contemplated, however. As further shown in FIG. 5, the buckle 500 includes a pair of slots 504 that in turn accommodate a strap 600 (FIG. 6).

Figure 6:
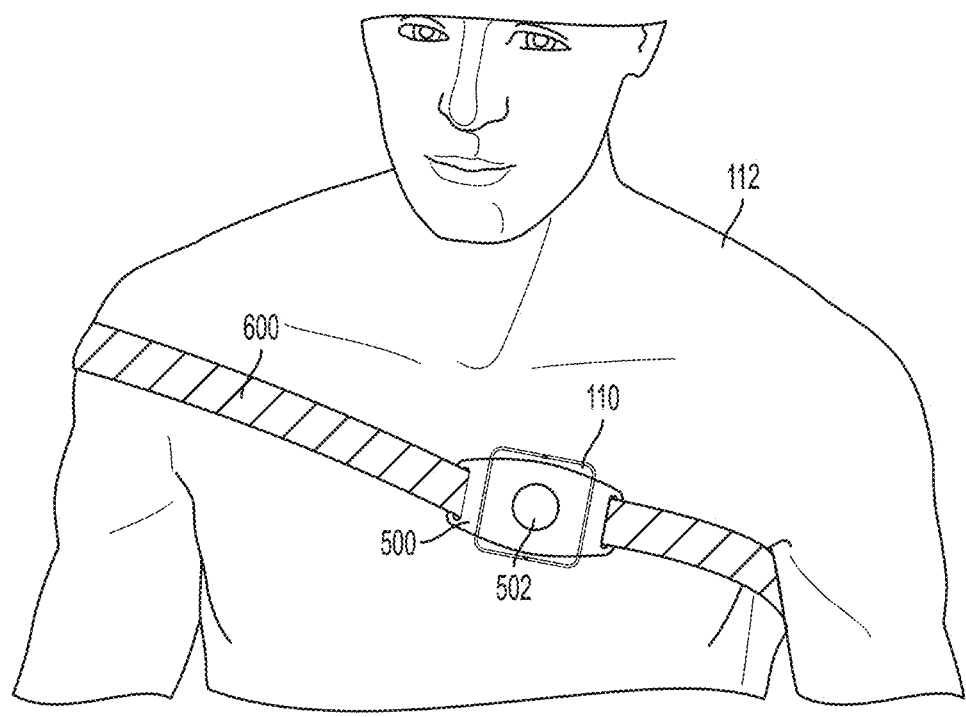
FIG. 6 shows an example of the ultrasound patch fastened to a patient using the strap of FIG. 5 in accordance with certain embodiments described herein.

FIG. 6 shows an example of the ultrasound patch 110 fastened to the patient 112 using the strap 600 in accordance with certain embodiments described herein. In this example, the strap 600 is wrapped around the patient 112 and appropriately tightened in order to secure the ultrasound patch 110 to a desired location on the patient 112 for acquisition of desired ultrasound data and/or delivery of desired ultrasound energy.

In some embodiments, the ultrasound patch 110 may weigh no more than 4 lbs (e.g., no more than 2 lbs). In some embodiments, the volume of the wearable ultrasound device may be no greater than 250 $cm^3$ (e.g., no greater than 125 $cm^3$, or no greater than 50 $cm^3$). In some embodiments, the ultrasound transducers of the ultrasound patch 110 may be arranged in an array, and the height of the wearable ultrasound device along the direction orthogonal to the array of ultrasound transducers (i.e., orthogonal to the face of the array) may be no greater than 7 cm (e.g., no greater than 5 cm.) In some embodiments, the height of the wearable ultrasound device along the direction orthogonal to the array of ultrasound transducers may be no greater than a dimension of the array of ultrasound transducers (i.e., the length or width of the array). As described above, the portability/wearability (i.e., the acceptably small size/weight) of the ultrasound patch 110 may be due, in part, to monolithically integrating ultrasound transducers onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

Additional information regarding the fabrication and integration of ultrasound transducers with CMOS wafers (e.g., to form the CMOS chip 134, which may be an ultrasound-on-a-chip) may be found in U.S. Pat. No. 9,067,779 titled MICROFABRICATED ULTRASONIC TRANSDUCERS AND RELATED APPARATUS AND METHODS, granted on Jun. 30, 2015 (and assigned to the assignee of the present application), the contents of which are incorporated by reference herein in their entirety. Additional information regarding the circuit components of the CMOS chip 134 may be found in U.S. Pat. No. 9,521,991 titled "MONOLITHIC ULTRASONIC IMAGING DEVICES, SYSTEMS, AND METHODS," granted on Dec. 20, 2016 (and assigned to the assignee of the instant application), the contents of which are incorporated by reference herein in their entirety.

As described above, an ultrasound device may wirelessly offload ultrasound data to an auxiliary device in real-time. The ultrasound information may include data sufficient to construct an ultrasound image therefrom. Wireless offloading of ultrasound data from the ultrasound device may allow the ultrasound device to offload data while the patient wearing the ultrasound device performs routine activities. In other words, the patient wearing the ultrasound device need not be tethered, by a wired connection, to another auxiliary device to which the ultrasound device offloads data. In contrast to transmitting an alarm signal or metric automatically generated by an ultrasound device based on collected ultrasound data, offloading data sufficient to construct an ultrasound image therefrom may be helpful because an ultrasound image may provide more information than a transmitted alarm signal or metric, and because this may allow a medical professional to view the ultrasound image. For example, ultrasound data may contain an unexpected indication that an ultrasound device may not be programmed to automatically detect. By offloading data sufficient to construct a full ultrasound image, a medical professional may be able to detect the unexpected indication upon viewing the ultrasound image.

However, wirelessly offloading data sufficient to construct an ultrasound image therefrom may be difficult because the rate of data produced by an ultrasound device that may be required for constructing an ultrasound image may exceed the data offload rate capabilities of wireless communication platforms. The following calculation illustrates the rate of data that may be produced by an ultrasound device in an example bladder application. For ultrasound imaging of the bladder, the ultrasound device may produce 16 multilines of data per ultrasound transmit event, each multiline having 960 samples, and each sample having 16 bits. The ultrasound device may produce 72 multilines per frame and 10 frames per second. Accordingly, the rate of data produced by the ultrasound device may be 16 (multilines per transmit)× 960 (samples per multiline)×16 (bits per sample)×72 (multilines per frame)×10 (frames per second)=177 megabits/ second. This data offload rate may exceed the data offloading capabilities of certain long-range communication platforms. For example, the IEEE 802.11n wireless networking standard may support data offload rates up to 72 megabits/ second and the IEEE 802.11g wireless networking standard may support data offload rates up to 54 megabits/second.

The inventors have recognized that the data offload rate from the ultrasound device may be reduced by implementing compounding of multilines of ultrasound data on the ultrasound device (e.g., on an FPGA in the ultrasound device, an ASIC in the ultrasound device, an ultrasound-on-a-chip in the ultrasound device, and/or other processing circuitry in the ultrasound device) that collects the ultrasound data, rather than on an auxiliary electronic device to which the ultrasound device offloads ultrasound data. For example, in embodiments in which an ultrasound probe is coupled to a host device to which the ultrasound probe transmits ultrasound data, the ultrasound probe may perform compounding of multilines rather than the host device. Multiple ultrasound transducers in the ultrasound device may transmit ultrasound waves into tissue during an ultrasound transmit event, and the ultrasound waves may be reflected off the tissue and detected by the ultrasound transducers in the ultrasound device. Using beamforming techniques, these detected reflection signals from multiple ultrasound transducers may be combined to form multilines (a.k.a. A-lines) in the direction of the transmitted beam. (It should be noted that in some embodiments, beamforming may be done first in an elevational direction and then in an azimuthal direction.) Following a subsequent ultrasound transmit event, certain of the ultrasound transducers may detect reflected ultrasound waves that are focused along the same direction as ultrasound waves collected following the previous ultrasound transmit event. In other words, multilines collected following different transmit events may overlap. (As referred to herein, multilines that "overlap" should be understood to mean that are focused along the same direction.) Compounding refers to combination of these overlapping multilines, and may include magnitude summation ("incoherent compounding") or complex summation ("coherent compounding") of overlapping multilines. In particular, incoherent compounding may include simple addition of overlapping multilines in linear or log domains, and coherent compounding may include addition of overlapping, weighted multilines with a phase shift. As an illustrative example, a single transmit event may produce N=16 multilines. Without compounding on the ultrasound device, all 16 multilines must be offloaded from the ultrasound device to an auxiliary device. The next transmit event may produce 16 more multilines, 12 of which may overlap with 12 multilines from the previous transmit event. (As described below, this may correspond to a pitch factor p=4.) Again, 16 multilines must be offloaded from the ultrasound device to an auxiliary device. The auxiliary device, or another device in communication with the auxiliary device, may then combine the 12 multilines from each transmit event together. With compounding on the ultrasound device, only the 4 nonoverlapping multilines from the first transmit event may need to be offloaded from the ultrasound device after the first transmit event. The remaining 12 multilines may remain on the ultrasound device to be combined with the 12 overlapping multilines from the second transmit. Therefore, without compounding on the ultrasound device, 16 multilines may need to be offloaded from the ultrasound device per transmit event, but with compounding on the ultrasound device, 4 multilines may need to be offloaded from the ultrasound device per transmit event.

The offset in multilines between the first multiline of successive ultrasound transmit events may be referred to as the pitch factor. Depending on the pitch factor, certain multilines may be collected following an ultrasound transmit event but not overlap with multilines collected following the subsequent ultrasound transmit event. Similarly, depending on the pitch factor, certain multilines may be collected following an ultrasound transmit and overlap with multilines collected in the following ultrasound transmit. In the bladder imaging example above, the pitch factor is 4, which means that for 16 multilines collected following each ultrasound transmit event, 12 multilines collected following one ultrasound transmit event may overlap with multilines collected following the successive ultrasound transmit event, while 4 multilines collected following the ultrasound transmit event will not overlap with multilines collected following the successive ultrasound transmit event.

As referred to herein, multilines collected "following" or "from" a transmit event should be understood to mean that ultrasound transducers may transmit ultrasound waves into tissue during a transmit event, and the ultrasound waves may be reflected off the tissue and detected by the ultrasound transducers. Using beamforming techniques, these reflection signals may be combined to form multilines.

Figure 7:
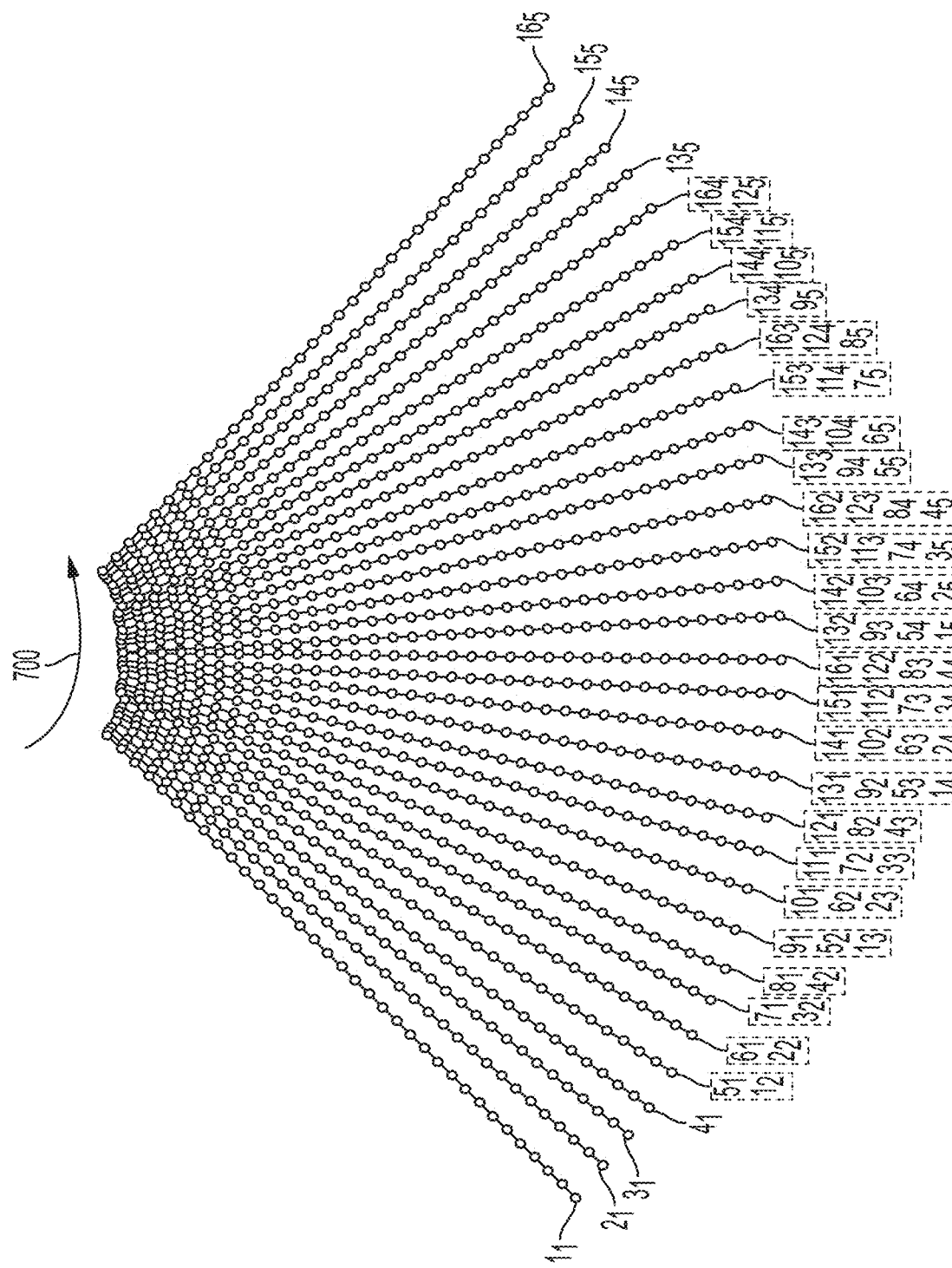
FIG. 7 shows an illustration of multilines from different ultrasound transmit events being focused in the same direction during ultrasound scanning.

FIG. 7 shows an illustration of multilines from different ultrasound transmit events being focused in the same direction during ultrasound scanning. FIG. 7 shows a direction of scanning 700 and multilines $1_1$-$16_1$, $1_2$-$16_2$, $1_3$-$16_3$, $1_4$-$16_4$, and $1_5$-$16_5$, wherein the multilines are drawn along their direction of focus. The main numeral in a multiline reference number represents the multiline's direction of focus in space relative to the other multilines collected from a particular ultrasound transmit event, with increasing numerals referring to multilines collected further along the direction of scanning 700. (In general, as referred to herein, "multilines a-b," where b>a, should be understood to refer to a−b+1 multilines, where the bth multiline is focused furthest along the direction of scanning, the (b−1)th multiline is focused next furthest along the direction of scanning, etc., and the ath multiline is focused least far along the direction of scanning.) The superscript in a multiline reference number represents the transmit event from which the multilines are collected. FIG. 7 shows multilines from 5 ultrasound transmit events with 16 multilines per transmit. Furthermore, the pitch factor is 4, meaning that the first multiline of an ultrasound transmit event is offset by 4 multilines from the first multiline of the previous ultrasound transmit event. In other words, the first multiline of an ultrasound transmit event is focused in the same direction as the fifth multiline of the previous ultrasound transmit event, and accordingly the second multiline of an ultrasound transmit event is focused in the same direction as the sixth multiline of the previous ultrasound transmit event, etc. FIG. 7 shows a box around multilines from different ultrasound transmit events that are focused in the same direction.

The multilines that are collected from an ultrasound transmit event, but do not overlap with multilines collected from the following ultrasound transmit event, are the multilines offloaded from the ultrasound device after the ultrasound transmit event. The remaining multilines collected from the ultrasound transmit event, which will overlap with multilines collected from the following ultrasound transmit event, are retained on the ultrasound device to be compounded with the overlapping multilines from the following ultrasound transmit event. Returning to the example data offload rate calculation for bladder imaging described above, the pitch factor is 4, resulting in a reduction in the data offload rate required for offloading from the ultrasound device from 177 megabits/second to 4 (multilines per transmit)×960 (samples per multiline)×16 (bits per sample)×72 (multilines per frame)×10 (frames per second)=44 megabits/second (approximately), which may be in the range of long-range communication platforms employing wireless networking standards such as an IEEE 802.11 standard (e.g., IEEE 802.11n and IEEE 802.11g).

In some embodiments, the number of multilines per transmit may be between or equal to 2-32. In some embodiments, the pitch factor may be between or equal to 1-8. Table 1 shows example values for these and other parameters that may be used for imaging different anatomical areas and structures:

TABLE 1

Example values for various parameters that may be used for imaging different anatomical areas and structures.

| Anatomical Area/Structure | Multilines/ Transmit | Transmits/ Frame | Pitch Factor | Frames/ Second |
|---|---|---|---|---|
| Abdominal | 16 | 95 | 8 | 15-30 |
| Abdominal Deep | 16 | 87 | 2 | 15-30 |
| Abdominal Vascular | 16 | 72 | 4 | 15-20 |
| Bladder | 16 | 72 | 4 | 15-20 |
| Cardiac | 4 | 40 | 2 | 25-30 |
| Cardiac Deep | 4 | 40 | 2 | 20-30 |
| Carotid | 16 | 30 | 4 | 15-20 |
| Obstetric | 16 | 72 | 4 | 15-20 |

In some embodiments, using the techniques described herein, the offload data rate from the ultrasound device may be reduced to any value between or equal to approximately 10 megabits/second-1.73 gigabits/second. For example, the offload data rate may be in the range of 10 megabits/second-32 megabits/second, 10 megabits/second-54 megabits/second, 10-megabits/second-72 megabits/second, 10-megabits/second-100 megabits/second, 10-megabits/second-450 megabits/second, 10-megabits/second-866.7 megabits/second, or any suitable offload data rate. The offload data rate may depend on the anatomical area of structure being imaged. In particular, the offload data rate may depend on the values selected for certain imaging parameters such as those shown in Table 1, as well as on truncation as described further below. In some embodiments, using the techniques described herein, ultrasound images in which objects 5 mm apart can be spatially resolved may be offloaded.

In some embodiments, the ultrasound device may include a long-range communication platform employing a store and forward technique (e.g., a Bluetooth platform). In particular, the long-range communication platform may store data in memory on the ultrasound device, thus enabling the data to be offloaded later at a lower data rate. In such embodiments, the techniques described herein may be used to reduce the amount of memory required on the ultrasound device. In some embodiments, the amount of memory on the ultrasound device may be equal to or between approximately 5 kilobytes and 20 megabytes (e.g., between approximately 5 kilobytes and 100 kilobytes, between approximately 100 kilobytes and 1 megabyte, between approximately 1 megabyte and 10 megabytes, or between approximately 10 megabytes and 20 megabytes). In other embodiments, the amount of memory on the ultrasound device may be greater than or less than these values. The amount of memory on the ultrasound device may be chosen based on the expected number of multilines per transmit event, samples per multiline, bits per sample, and acquisitions per frame, as well as the number of frames to be stored on the ultrasound device prior to offloading.

In some embodiments, when offloading multilines, the ultrasound device may truncate the digital multiline data. For example, if an analog-to-digital converter (ADC) in the ultrasound device converts analog multiline data to 16-bit digital multiline data, the ultrasound device may truncate the digital multiline data to 12 bits prior to offloading the multiline data. It should be appreciated that the ultrasound device may truncate the digital multiline data to other resolutions, such as 15 bits, 14 bits, 13 bits, 11 bits, or 10 bits. It should also be appreciated that analog-to-digital converters with other resolutions, such as 18 bits or 20 bits, may be used in the ultrasound device, and the ultrasound device may truncate the digital multiline data to 19 bits, 18 bits, 17 bits, 16 bits, 15 bits, 14 bits, or 13 bits prior to offloading the multiline data. The number of bits to which the multiline data is truncated may depend on required image quality and/or signal-to-noise ratio in ultrasound images produced from the multiline data. Truncating the digital multiline data from M bits to N bits prior to offloading reduces the data offload rate by 1−N/M times the data offload rate without truncation. For example, truncating the digital multiline data from 16 bits to 12 bits prior to offloading reduces the data offload rate by 1−12/16=0.25 times the data offload rate without truncation. In the example data offload rate calculation for bladder imaging described above, truncating the digital multiline data from 16 bits to 12 bits may reduce the data offload rate from approximately 44 megabits/second to 44−44×0.25=33 megabits/second (approximately).

In some embodiments, portions of the digital circuitry of the ultrasound device may include configurable bit depth. For example, the bit depth of the digital output of an ADC on the ultrasound device may be configurable (i.e., the ADC may be configured to convert analog ultrasound data to any of a combination of 10 bits, 11 bits, 12 bits, 13 bits, 14 bits, 15 bits, 16 bits, 17 bits, 18 bits, 19 bits, or 20 bits, for example). Similarly, portions of the digital computing pipeline and memory (e.g., any of the memory buffers described below) may be configured to operate on/store digital data having a configurable number of bits. Such portions of the digital computing pipeline may include, for example, digital filter circuitry, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, and/or output buffering circuitry. Configurable bit depth may enable reduction in data rate in a similar manner as truncation of data. In some embodiments, to configure the computing pipeline of the ultrasound device to use a particular bit depth, a user may select an option (e.g., a button or other selection means on the ultrasound device or an electronic device in communication with the ultrasound device) corresponding to the particular bit depth. Selection of that option may transmit signals to the computing pipeline in order to configure the computing pipeline to produce, operate on, and/or store digital having the particular number of bits. In some embodiments, selection of a particular bit depth may be performed automatically by the ultrasound device or an electronic device in communication with the ultrasound device. For example, the ultrasound device or electronic device may determine the offload data rate possible from the ultrasound device and calculate the maximum bit depth possible given the available offload data rate.

Figure 8:
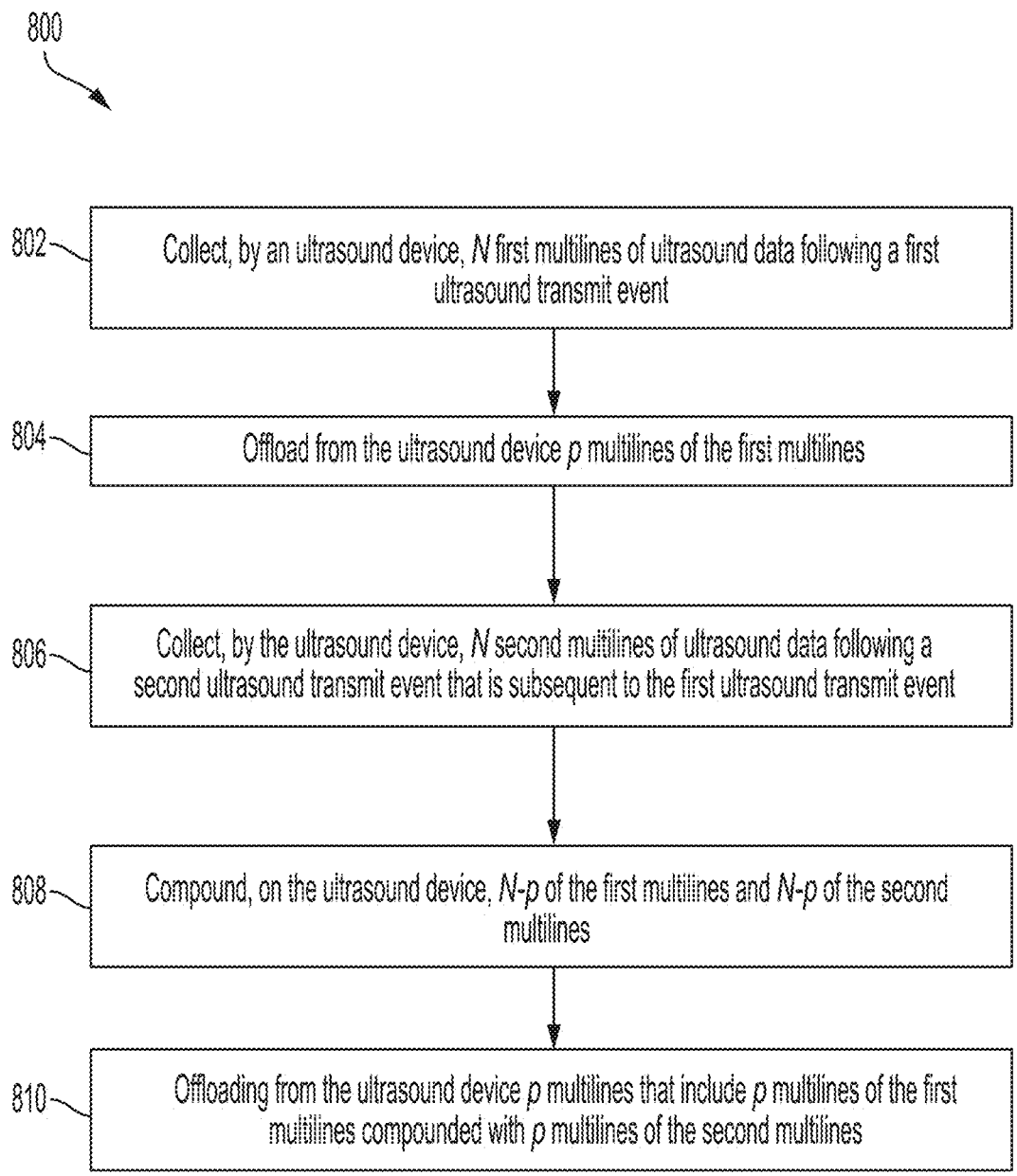
FIG. 8 shows an example process for compounding multilines of ultrasound data in accordance with certain embodiments described herein.

FIG. 8 shows an example process 800 for collecting ultrasound data in accordance with certain embodiments described herein. The process includes compounding multilines of ultrasound data on an ultrasound device configured to collect ultrasound data. The ultrasound device may be a wearable ultrasound device, such as an ultrasound patch (described in more detail with reference to FIGS. 1-6), and the process 800 may be performed by processing circuitry (e.g., a FPGA, an ASIC, and/or an ultrasound-on-a-chip) in the ultrasound device. The process 1000 begins at act 802.

In act 802, the ultrasound device collects N first multilines of ultrasound data following a first ultrasound transmit event. The process 800 then proceeds to act 804.

In act 804, the ultrasound device offloads p multilines of the first multilines. p may correspond to the pitch factor of multilines collected by the ultrasound device following successive ultrasound transmit events, and therefore the p multilines offloaded from the ultrasound device may be multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading. The process 800 then proceeds to act 806.

In act 806, the ultrasound device collects N second multilines of ultrasound data following a second ultrasound transmit event that is subsequent to the first ultrasound transmit event. The process 800 then proceeds to act 808.

In act 808, the ultrasound device compounds N−p of the first multilines and N−p of the second multilines. The N−p of the first multilines and the N−p of the second multilines may be overlapping multilines. Compounding may include magnitude summation ("incoherent compounding") or complex summation ("coherent compounding") of overlapping multilines. In particular, incoherent compounding may include adding the N−p of the first multilines and the N−p of the second multilines in linear or log domains, and coherent compounding may include adding the N−p of the first multilines and the N−p of the second multilines with weighting and phase shifting applied. The process 800 then proceeds to act 810.

In act 810, the ultrasound device offloads p multilines that include p multilines of the first multilines compounded with p multilines of the second multilines. The p multilines offloaded from the ultrasound device may be multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading.

As can be appreciated from the description of the process 800, because compounding of overlapping multilines occurs on the ultrasound device, only p multilines may be offloaded from the ultrasound device per transmit, rather than offloading N multilines, despite N (which is greater than p) multilines being collected per ultrasound transmit event. This constitutes a reduction in data offload rate by a factor of p/N. The remaining N−p multilines that were collected following an ultrasound transmit event but not offloaded may be retained on the ultrasound device to be compounded with overlapping multilines collected following the subsequent ultrasound transmit event.

It should be appreciated that while the description of process 800 may discuss compounding of multilines from the first and second ultrasound transmit events in an imaging session, the process 800 may proceed similarly for ultrasound transmit events that are not the first and second ultrasound transmit events in an imaging session. In such a case, act 808 may include compounding N−p multilines from the current ultrasound transmit event with multilines collected from two or more previous ultrasound transmit events.

Figure 9:
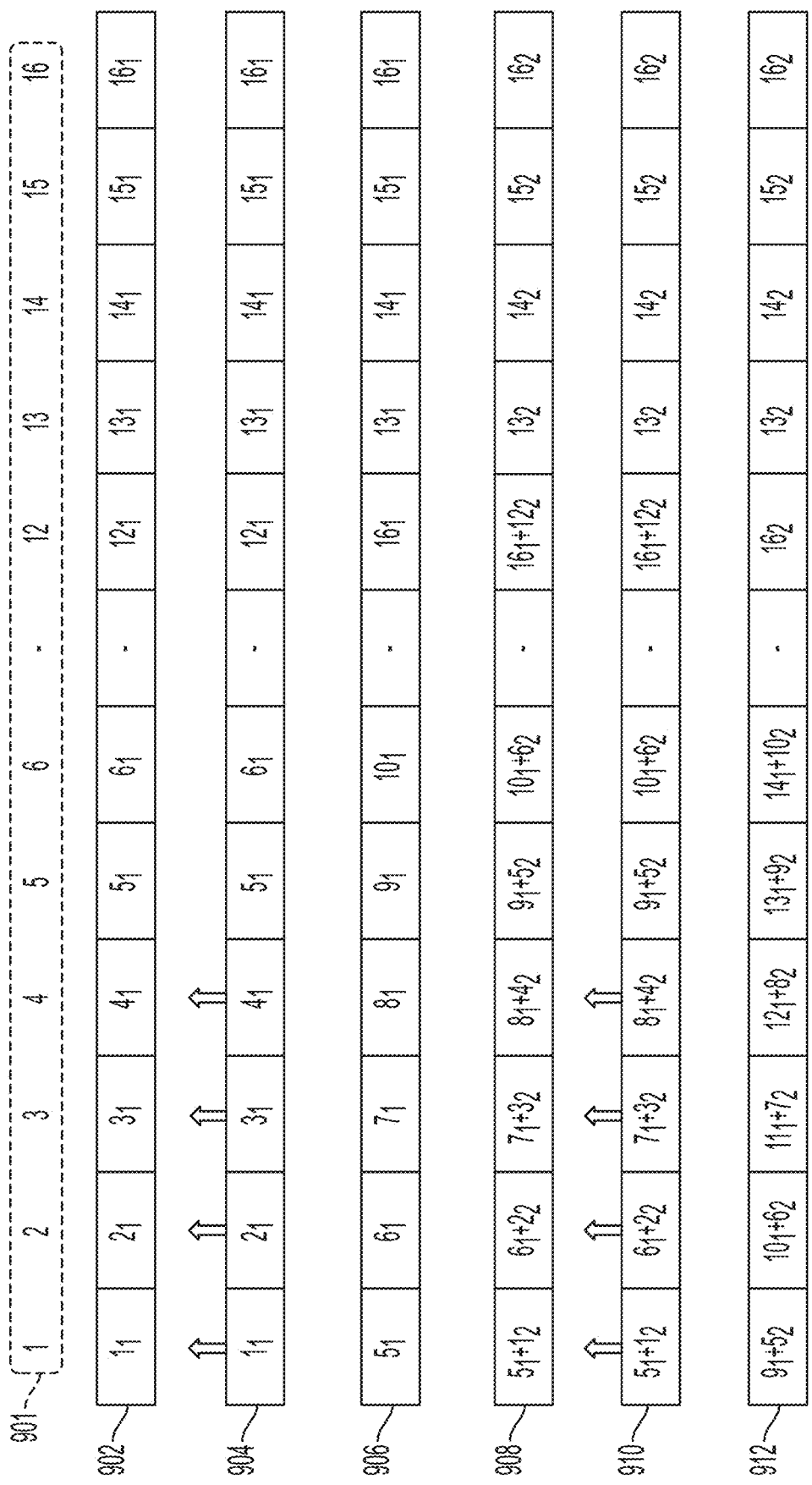
FIG. 9 shows, using a symbolic illustration of a memory buffer, an example of compounding multilines of ultrasound data in accordance with certain embodiments described herein.

FIG. 9 shows an example of collecting ultrasound data in accordance with certain embodiments described herein. The process illustrated in the example includes compounding multilines of ultrasound data on an ultrasound device configured to collect ultrasound data. The ultrasound device may be a wearable ultrasound device, such as an ultrasound patch (described in more detail with reference to FIGS. 1-6) that includes a memory buffer. FIG. 9 shows a symbolic illustration of the memory buffer (which may be part of volatile or non-volatile memory in the ultrasound device) storing data for multiple multilines at various addresses. The address indicator 901 indicates the addresses for the memory buffer. The data in the buffer is addressed with addresses 1-16. The buffer is configured to shift data out from the left side and shift data in from the right side (although it may be possible to the buffer to shift data out from the right side and shift data in from the left side). The data stored in the memory buffer is shown at different stages of the compounding process.

In the following description, multilines are represented with a main numeral and a subscript. The main numeral represents the relative position in space of the multilines collected from a particular ultrasound transmit event, with increasing numerals referring to multilines collected further along the scanning direction of the ultrasound imaging. (Because ultrasound scanning may be considered to collect data in a polar coordinate system, in the following description, scanning will be referred to as proceeding from a negative angle direction to a positive angle direction.) For example, if multilines $1_1$-$16_1$ are collected, multiline $1_1$ would be the multiline collected furthest in the negative angle direction and multiline $16_1$ would be the multiline collected furthest in the positive angle direction. The superscript represents the transmit event in which the multilines are collected.

As described above, the offset in multilines between the first multiline of successive ultrasound transmit event may be referred to as the pitch factor p. If N multilines are collected per ultrasound transmit event, p of those N multilines will not overlap with multilines collected from the following ultrasound transmit event and N−p multilines will overlap with multilines collected from the following ultrasound transmit event. As an example, if 16 multilines $1_1$-$16_1$ are collected from one ultrasound transmit event, and the pitch factor is 4, then multilines $1_1$-$4_1$ (i.e., the 4 multilines collected furthest in the negative angle direction) will not overlap with multilines collected from the following ultrasound transmit event, while multilines $5_1$-$16_1$ will overlap with multilines collected from the following ultrasound transmit event. The following ultrasound transmit event will result in 16 multilines $1_2$-$16_2$ being collected, with multilines $1_2$-$12_2$ overlapping with multilines $5_1$-$16_1$.

At stage 902, a first transmit event produces N=16 multilines $1_1$-$16_1$. The ultrasound device updates the buffer to store data for the 16 multilines produced from the first transmit event, with multiline $1_1$ stored at address 1, multiline $2_1$ stored at address 2, etc. In the example of FIG. 9, N=16 but other multilines per ultrasound transmit event values are possible.

At stage 904, the ultrasound device offloads data (as represented by the arrows) from the leftmost p=4 multilines in the buffer (i.e., multilines $1_1$-$4_1$ at addresses 1-4). p corresponds to the pitch factor of the multilines, and therefore the p multilines $1_1$-$4_1$ offloaded from the ultrasound device are multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading. In the example of FIG. 9, p is 4, but other pitch factors (e.g., 2, 8) are possible.

At stage 906, the ultrasound device shifts data from the leftmost p=4 multilines in the buffer (i.e., multilines $1_1$-$4_1$ at addresses 1-4) out of the buffer and shifts data from the remaining multilines (i.e., multilines $5_1$-$16_1$ at addresses 5-16) by p addresses to the left. The rightmost p=4 addresses retain the data they stored prior to stage 906.

At stage 908, a second transmit event produces N=16 multilines. Due to the pitch factor of 4, N−p=12 multilines produced from the second transmit event overlap with N−p=12 multilines from the first transmit. Accordingly, the multilines produced from the second transmit event are symbolized as multilines $1_2$-$16_2$, with multilines $1_2$-$12_2$ from the second transmit event overlapping with multilines $5_1$-$16_1$ from the first transmit event. The ultrasound device compounds data from multilines $1_2$-$12_2$ from the second transmit event with the data at addresses 1-12 in the buffer, respectively (as represented by the addition symbol). Compounding may include magnitude summation ("incoherent compounding") or complex summation ("coherent compounding") of overlapping multilines. In particular, incoherent compounding may include adding multilines $1_2$-$12_2$ from the second transmit event and the data at addresses 1-12 in the buffer in linear or log domains, and coherent compounding may include adding multilines $1_2$-$12_2$ from the second transmit event and the data at addresses 1-12 in the buffer with weighting and phase shifting applied. The ultrasound device further overwrites the data at the rightmost p=4 addresses with multilines $13_2$-$16_2$.

At stage 910, the ultrasound device offloads data from the leftmost p=4 multilines in the buffer (i.e., multilines $5_1$+$1_2$-$8_1$+$4_2$ at addresses 1-4), similar to stage 904. In some embodiments, the ultrasound device may truncate the multiline data (e.g., to 10 or 12 bits) prior to offloading.

At stage 912, the ultrasound device shifts data from the leftmost p=4 multilines in the buffer (i.e., multilines $5_1$+$1_2$-$8_1$+$4_2$ at addresses 1-4) out of the buffer and shifts data from the remaining multilines (i.e., multilines $9_1$+$5_2$-$16_1$+$12_2$, $13_2$-$16_2$ at addresses 5-16) to the left. The rightmost p=4 addresses retain the data they stored prior to stage 906. Update, offload, and shift operations, similar to stages 908, 910, and 912, may then be repeated. For example, the next update stage may result in multilines $9_1$+$5_2$+$1_3$-$12_1$+$8_2$+$4_3$ being offloaded from the ultrasound device.

In some embodiments, at stage 906, rather than the rightmost p addresses retaining the data they stored prior to stage 906, the rightmost p addresses may be filled with zeros. In such embodiments, the new multiline data collected at stage 908 may be compounded with the data in the rightmost p address (i.e., compounded with zeros), rather than overwriting the data in the rightmost p addresses. Accordingly, the new multiline data collected at stage 908 may be compounded with the data at all the addresses 1-16 of the memory buffer.

Figure 10:
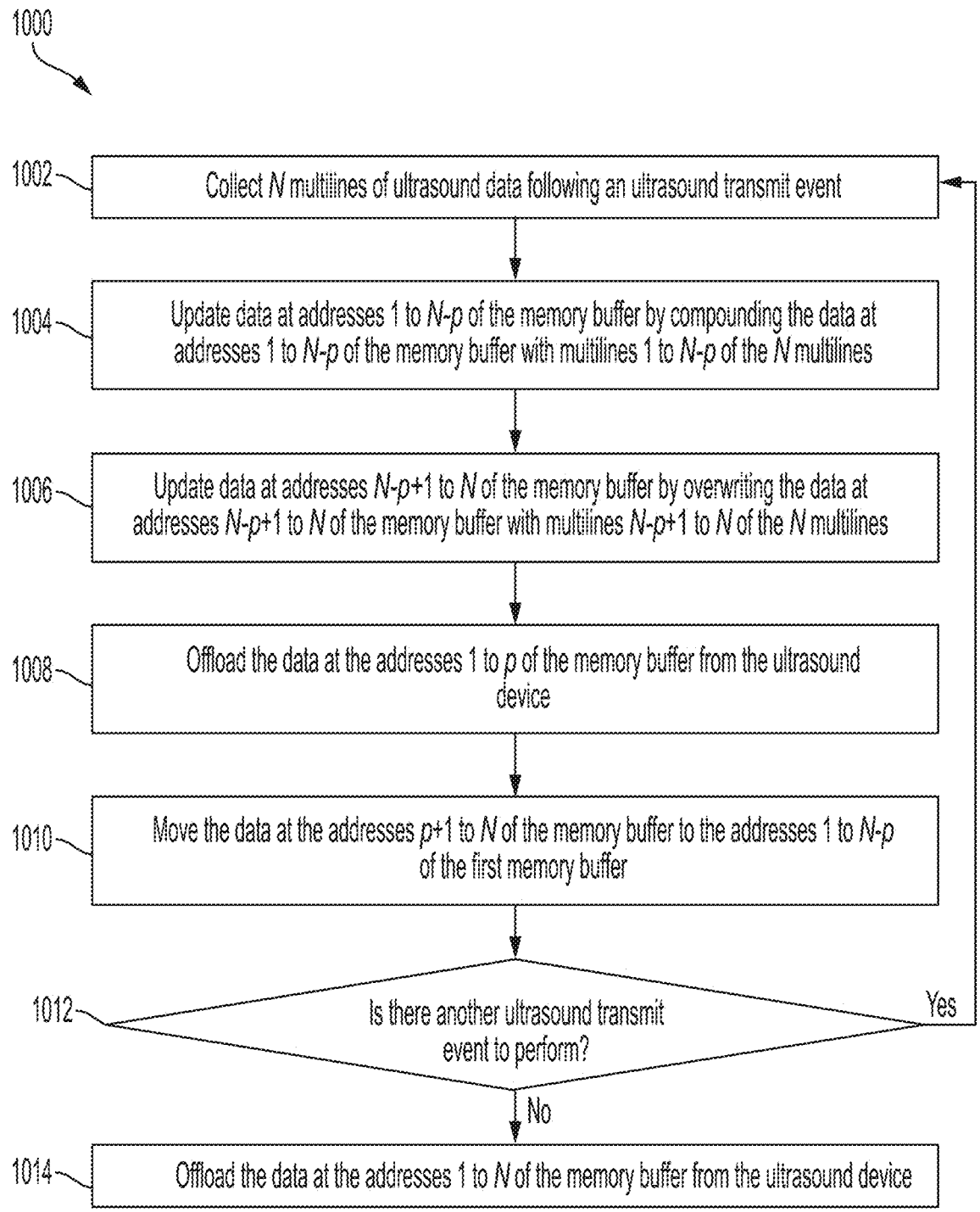
FIG. 10 shows in flow chart form the process that is illustrated through the example in FIG. 9.

FIG. 10 shows an example process 1000 for collecting ultrasound data in accordance with certain embodiments described herein. The process includes compounding multilines of ultrasound data on an ultrasound device configured to collect ultrasound data. The ultrasound device may be a wearable ultrasound device, such as an ultrasound patch (described in more detail with reference to FIGS. 1-6), and the process 1000 may be performed by processing circuitry (e.g., a FPGA, an ASIC, and/or an ultrasound-on-a-chip) in the ultrasound device. Process 1000 shows in flow chart form the process that is illustrated through the example in FIG. 9 for compounding multilines of ultrasound data on a memory buffer (which may be part of volatile or non-volatile memory) in an ultrasound device. The process 1000 begins at act 1002.

In act 1002, the ultrasound device collects N multilines of ultrasound data following an ultrasound transmit event (referred to as the "present ultrasound transmit event"). The process 1000 then proceeds to act 1004.

In act 1004, the ultrasound device updates data at addresses 1 to N−p of the memory buffer by compounding the data at addresses 1 to N−p of the memory buffer with multilines 1 to N−p of the N multilines. Compounding may include magnitude summation ("incoherent compounding") or complex summation ("coherent compounding") of overlapping multilines. In particular, incoherent compounding may include adding the data at addresses 1 to N−p of the memory buffer and multilines 1 to N−p of the N multilines in linear or log domains, and coherent compounding may include adding the data at addresses 1 to N−p of the memory buffer and multilines 1 to N−p of the N multilines with weighting and phase shifting applied. Prior to updating the data at addresses 1 to N−p of the memory buffer, the memory buffer may have stored, at addresses 1 to N−p, multilines of ultrasound data collected following one or more ultrasound transmit events prior to the ultrasound transmit event. If the ultrasound device collects multilines by scanning from a negative angle direction to a positive angle direction, the ultrasound device may compound the multiline furthest in the negative angle direction with the data at address 1, the multiline second furthest in the negative angle direction with the data at address 2, etc. As will be described further with reference to act 1010, each multiline collected following the present ultrasound transmit event may be compounded with the data in the memory buffer that, prior to the updating, stored multilines that overlap with the collected multiline. The process 1000 then proceeds to act 1006. In some embodiments, act 1006 may be performed prior to act 1004, or acts 1004 and 1006 may be performed simultaneously.

In act 1006, the ultrasound device updates data at addresses N−p+1 to N of the memory buffer by overwriting the data at addresses N−p+1 to N of the memory buffer with multilines N−p+1 to N of the N multilines. As will be described further with reference to act 1010, addresses N−p+1 to N of the memory buffer may store data that is replicated elsewhere in the memory buffer, and can therefore be overwritten in act 1006 without loss of data. Acts 1002, 1004, and 1006 correspond to stage 908 in FIG. 9. The process 1000 then proceeds to act 1008.

In act 1008, the ultrasound device offloads the data at addresses 1 to p of the memory buffer from the ultrasound device. p may correspond to the pitch factor of multilines collected by the ultrasound device following successive ultrasound transmit events, and the p multilines offloaded from the ultrasound device may be multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading. Act 1008 corresponds to stage 910. The process 1000 then proceeds to act 1010.

In act 1010, the ultrasound device moves the data at the addresses p+1 to N of the memory buffer to the addresses 1 to N−p of the memory buffer. Therefore, the data that was previously at addresses 1 to p of the memory buffer, and was already offloaded from the ultrasound device, is removed from the memory buffer. Due to the pitch factor p, the data previously at address p+1 that is moved to address 1 corresponds to a multiline collected following the present ultrasound transmit event that will overlap with the multiline collected following the subsequent ultrasound transmit event that is furthest in the negative angle direction. Similarly, the data previously at address p+2 that is moved to address 2 will correspond to a multiline collected from the present ultrasound transmit event that will overlap with the multiline collected from the subsequent ultrasound transmit event that is second furthest in the negative angle direction, etc. When new multilines are collected following the subsequent ultrasound transmit event, the ultrasound device may add the multiline furthest in the negative angle direction to the data at address 1, the multiline second furthest in the negative angle direction to the data at address 2, etc., (as described with reference to act 1004). This means that each multiline collected following the subsequent ultrasound transmit event may be added to the data in the memory buffer that, prior to the adding, stored multilines that overlap with the multiline collected following the subsequent ultrasound transmit event (as described with reference to act 1004).

When moving the data at the addresses p+1 to N of the memory buffer to the addresses 1 to N−p of the memory buffer, the memory buffer may retain at addresses N−p+1 to N the data that was stored at these addresses prior to act 1010. Accordingly, following act 1010, the data at addresses N−p+1 to N may be the same as the data at addresses N−2p+1 to N−p. Because the data at addresses N−p+1 to N may therefore be redundant, this data may be overwritten in act 1006 with loss of data. Act 1010 corresponds to stage 912. The process 1000 then proceeds to act 1012.

In some embodiments, at stage 1010, rather than the addresses N−p+1 to N retaining the data they stored prior to stage 1010, the addresses N−p+1 to N may be filled with zeros. In such embodiments, new multiline data collected following the next ultrasound transmit event may be compounded with the data at addresses N−p+1 to N (i.e., compounded with zeros), rather than overwriting the data at addresses N−p+1 to N. Accordingly, the new multiline data collected following the next ultrasound transmit event may be compounded with the data at all N addresses of the memory buffer.

In act 1012, the ultrasound device determines if there is another ultrasound transmit event to perform. If there is another ultrasound transmit event to perform, the process 1000 then proceeds to act 1002. If there is not another ultrasound transmit event to perform, the process 1000 then proceeds to act 1014.

In act 1014, the ultrasound device offloads the data at addresses 1 to N of the memory buffer from the ultrasound device. This offloaded data may represent all the remaining multiline data that has not yet been offloaded. The ultrasound device may offload the p multilines wirelessly. In some embodiments, the ultrasound device may truncate the multiline data (e.g., to 10 or 12 bits) prior to offloading. The process 1000 may then terminate.

Process 1000 is a process for compounding multilines on an ultrasound device, and particularly a process for manipulating a memory buffer on the ultrasound device to perform this compounding. As can be appreciated from the description of the process 1000, because compounding of overlapping multilines occurs on the ultrasound device, only p multilines may be offloaded from the ultrasound device per transmit, rather than offloading N multilines, despite N (which is greater than p) multilines being collected per ultrasound transmit event. This constitutes a reduction in data offload rate by a factor of p/N. The remaining N−p multilines that were collected following an ultrasound transmit event but not offloaded may be retained on the ultrasound device to be compounded with overlapping multilines collected from the following ultrasound transmit event.

Figure 11:
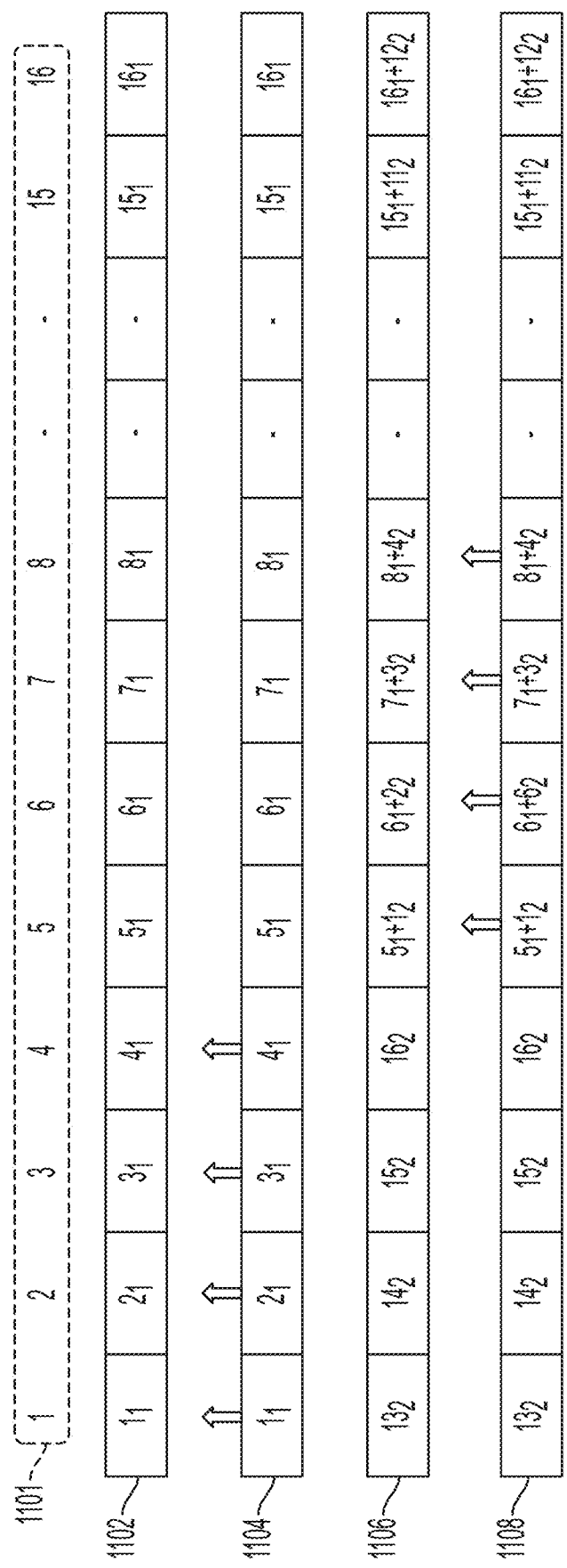
FIG. 11 shows variant of the example shown in FIG. 9.

FIG. 11 shows an example of collecting ultrasound data in accordance with certain embodiments described herein. The example shown in FIG. 11 is a variant of the example shown in FIG. 9. In particular, in FIG. 9, prior to updating the memory buffer with multilines produced from a new ultrasound transmit event, data in the memory buffer is shifted by p to the left. Because of this shift, multilines 1-N produced from the new ultrasound transmit event may be used to update addresses 1-N, respectively, in the memory buffer. In other words, the multiline farthest in the negative scanning angle direction is used to update address 1 of the memory buffer, the multiline second farthest in the negative scanning angle direction is used to update address 2 of the memory buffer, etc. In the variation shown in FIG. 11, no shifting occurs. Instead, multilines produced from a new ultrasound transmit event are used to update data in the memory buffer starting with the address directly after the rightmost address from which data was offloaded after the previous ultrasound transmit. In other words, if the rightmost address from which data was offloaded after the previous ultrasound transmit is called m, the multiline farthest in the negative scanning angle direction is used to update address m+1 of the memory buffer, the multiline second farthest in the negative scanning angle direction is used to update address m+2 of the memory buffer, etc. If the ultrasound device reaches the end of the memory buffer, the remaining multilines are used to update addresses starting with address 1. For example, if m is 8 and there are 16 multilines produced from the new ultrasound transmit event, multilines 1-8 may be used to update addresses 9-16 and multilines 9-16 may be used to update addresses 1-8. This may eliminate the shifting operation shown in FIG. 9 and increase efficiency of the compounding operation.

FIG. 11 shows a symbolic illustration of the memory buffer (which may be part of volatile or non-volatile memory in the ultrasound device) storing data for multiple multilines at various addresses. The address indicator 1101 indicates the addresses for the memory buffer. The data in the buffer is addressed with addresses 1-16. The buffer is configured to shift data out from the left side and shift data in from the right side (although it may be possible to the buffer to shift data out from the right side and shift data in from the left side). The data stored in the memory buffer is shown at different stages of the compounding process. FIG. 11 uses the same naming scheme for multilines as in FIG. 9.

At stage 1102, a first transmit event produces N=16 multilines $1_1$-$16_1$. The ultrasound device updates the buffer to store data for the 16 multilines produced from the first transmit event, with multiline $1_1$ stored at address 1, multiline $2_1$ stored at address 2, etc. In the example of FIG. 11, N=16 but other multilines per ultrasound transmit event values are possible.

At stage 1104, the ultrasound device offloads data (as represented by the arrows) from the leftmost p=4 multilines in the buffer (i.e., multilines $1_1$-$4_1$ at addresses 1-4). p corresponds to the pitch factor of the multilines, and therefore the p multilines $1_1$-$4_1$ offloaded from the ultrasound device are multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading. In the example of FIG. 11, p is 4, but other pitch factors (e.g., 2, 8) are possible.

At stage 1106, a second transmit event produces N=16 multilines. Due to the pitch factor of 4, N−p=12 multilines produced from the second transmit event overlap with N−p=12 multilines from the first transmit. Accordingly, the multilines produced from the second transmit event are symbolized as multilines $1_2$-$16_2$, with multilines $1_2$-$12_2$ from the second transmit event overlapping with multilines $5_1$-$16_1$ from the first transmit event. As further illustrated, the ultrasound device compounds data from multilines $1_2$-$12_2$ from the second transmit event with the data at addresses 5-16 in the buffer, namely multilines $5_1$-$16_1$ (as represented by the addition symbol). Compounding may include magnitude summation ("incoherent compounding") or complex summation ("coherent compounding") of overlapping multilines. In particular, incoherent compounding may include adding the data from multilines $1_2$-$12_2$ from the second transmit event and the data at addresses 5-16 in the buffer in linear or log domains), and coherent compounding may include adding the data from multilines $1_2$-$12_2$ from the second transmit event and the data at addresses 5-16 in the buffer with weighting and phase shifting applied. The ultrasound device overwrites the data that was offloaded in the stage 1104 (namely, multilines $1_1$-$4_1$ at addresses 1-4) with the multilines from the second transmit event that do not overlap with any multilines from the first transmit event (namely, multilines $13_2$-$16_2$).

More generally, the ultrasound device compounds the first N−p multilines produced from the second transmit event with data at the first N−p addresses in the memory buffer after the rightmost address from which data was offloaded in stage 1104. The ultrasound device overwrites the data at the addresses from which data was offloaded in stage 1104 with the last p multilines produced from the second transmit event.

In some cases, there may not be N−p addresses after the rightmost address from which data was offloaded in stage 1104 in the memory buffer (e.g., if the rightmost address is 8, N−p is 12, and the number of addresses is 16). In such cases, the ultrasound device compounds the multilines produced from the second transmit event, from negative angle direction to positive angle direction, with the data at the remaining addresses after the rightmost address, and then compounds remaining multilines with the data starting at address 1. For example, if the rightmost address is 8, N−p is 12, and the number of addresses is 16, the ultrasound device may compound multilines 1-8 with the data at addresses 9-16, respectively, and compound multilines 9-12 with the data at addresses 1-4, respectively.

At stage 1108, the ultrasound device offloads data from the first p=4 addresses that were updated in stage 1106 (i.e., multilines $5_1$+$1_2$−$8_1$+$4_2$ at addresses 5-8). In some embodiments, the ultrasound device may truncate the multiline data (e.g., to 10 or 12 bits) prior to offloading.

While multilines $1_1$-$16_1$ collected at stage 1102 are added to addresses 1-16, respectively, it is also possible for the multilines to be added to the memory buffer starting at any address. For example, multilines $1_1$-$15_1$ may be added to addresses 2-16 and multiline $16_1$ may be added to address 1.

Figure 12:
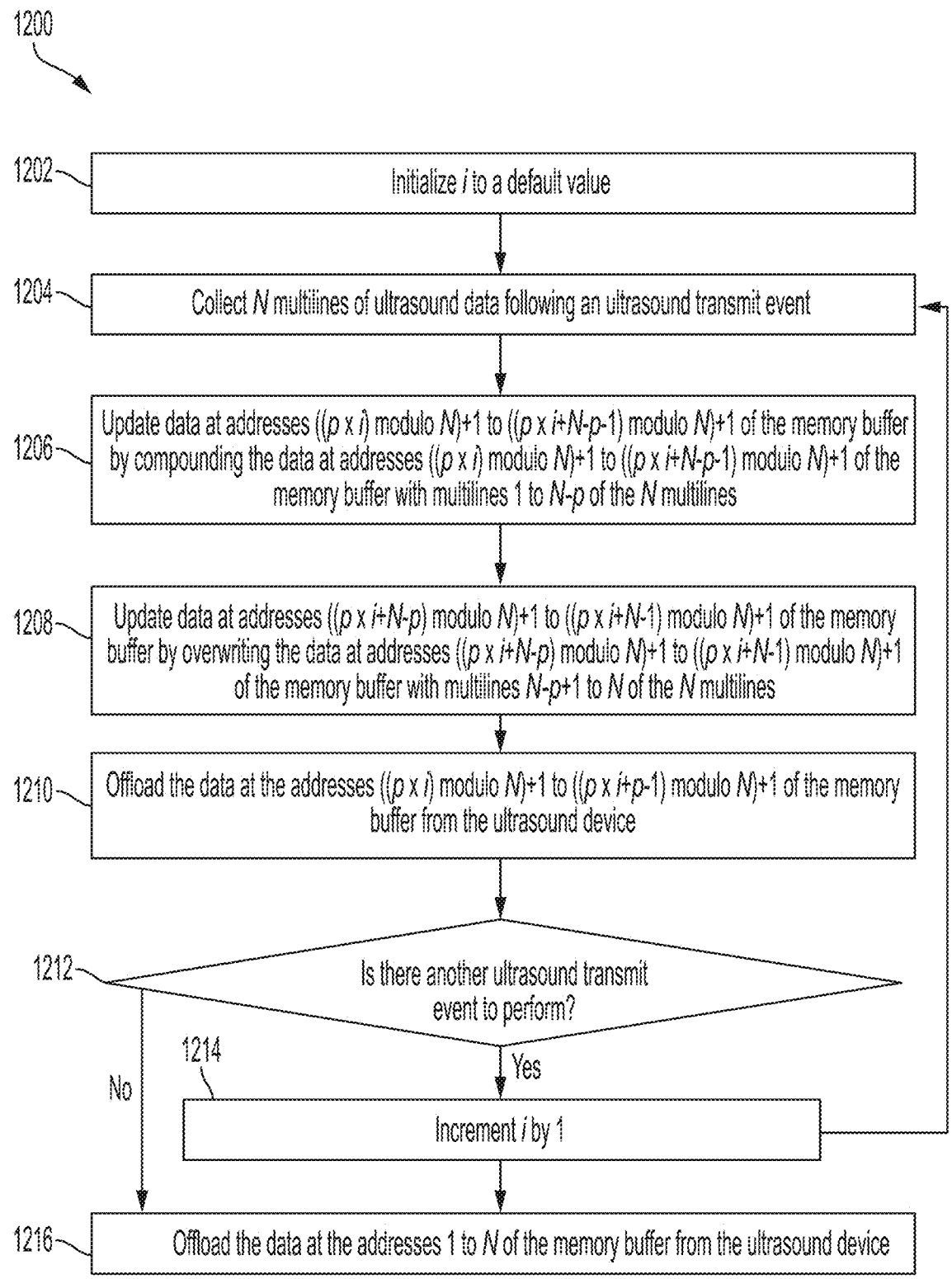
FIG. 12 shows in flow chart form the process that is illustrated through the example in FIG. 9.

FIG. 12 shows an example process 1200 for collecting ultrasound data in accordance with certain embodiments described herein. The process includes compounding multilines of ultrasound data on an ultrasound device configured to collect ultrasound data. The ultrasound device may be a wearable ultrasound device, such as an ultrasound patch (described in more detail with reference to FIGS. 1-6), and the process 1200 may be performed by processing circuitry (e.g., a FPGA, an ASIC, and/or an ultrasound-on-a-chip) in the ultrasound device. Process 1200 shows in flow chart form the process that is illustrated through the example in FIG. 11 for compounding multilines of ultrasound data on a memory buffer (which may be part of volatile or non-volatile memory) in an ultrasound device. The process 1200 begins at act 1202.

In act 1202, the ultrasound device initializes i to a default value. For example, the default value may be 0. As will be described further below, portions of the process 1200 may be iterated multiple times, and i may be a counter variable that is incremented after each iteration. The process 1200 then proceeds to act 1204.

In act 1204, the ultrasound device collects N multilines of ultrasound data following an ultrasound transmit event (referred to as the "present ultrasound transmit event"). The process 1200 then proceeds to act 1206.

In act 1206, the ultrasound device updates data at addresses ((p×i) modulo N)+1 to ((p×i+N−p−1) modulo N)+1 of the memory buffer by compounding the data at addresses ((p×i) modulo N)+1 to ((p×i+N−p−1) modulo N)+1 of the memory buffer with multilines 1 to N−p of the N multilines. p may correspond to the pitch factor of multilines collected by the ultrasound device following successive ultrasound transmit events. Compounding may include magnitude summation ("incoherent compounding") or complex summation ("coherent compounding") of overlapping multilines. In particular, incoherent compounding may include adding the data at addresses ((p×i) modulo N)+1 to ((p×i+N−p−1) modulo N)+1 of the memory buffer and multilines 1 to N−p of the N multilines in linear or log domains and coherent compounding may include adding the data at addresses ((p×i) modulo N)+1 to ((p×i+N−p−1) modulo N)+1 of the memory buffer and multilines 1 to N−p of the N multilines with weighting and phase shifting applied.

As an example, assume i was initialized to 0, the process 1200 proceeded through one iteration, i was incremented to 1, and the process 1200 returned to act 1206 (as will be described further below). Furthermore, consider that as a result of the first iteration through the process 1200, multilines $1_1$-$16_1$ were stored at addresses 1-16, respectively. During the second iteration through processes 1200, at act 1204, the ultrasound device may collect multilines $1_2$-$16_2$. At act 1206, multilines $1_2$-$12_2$ may be compounded with the data at addresses 5-16, which contain multilines $5_1$-$16_1$, respectively. Due to the pitch factor p=4, multilines $5_1$-$16_1$ may overlap with multilines $1_1$-$12_1$, and accordingly act 1206 may result in compounding overlapping multilines from successive transmit events. The process 1200 then proceeds to act 1208.

In act 1208, the ultrasound device updates data at addresses ((p×i+N−p) modulo N)+1 to ((p×i+N−1) modulo N)+1 of the memory buffer by overwriting the data at addresses ((p×i+N−p) modulo N)+1 to ((p×i+N−1) modulo N)+1 of the memory buffer with multilines N−p+1 to N of the N multilines. Following the example above, in act 1208, multilines $13_2$-$16_2$ may overwrite the data at addresses 1-4, which previously contained multilines $1_1$-$4_1$. Due to the pitch factor p=4, these multilines may not overlap with any multilines from successive ultrasound transmit events (and were already offloaded during the previous iteration through process 1200 at act 1210, as will be described further below). Accordingly, these multilines may be overwritten without loss of data. Acts 1204, 1206, and 1208 correspond to stage 1106. The process 1200 then proceeds to act 1210.

In act 1210, the ultrasound device offloads the data at addresses ((p×i) modulo N)+1 to ((p×i+p−1) modulo N)+1 of the memory buffer from the ultrasound device. Following the example above, in act 1210, the data at addresses 5-8 may be offloaded from the ultrasound device. These addresses contain multilines $5_1$-$8_1$ compounded with multilines $1_2$-$4_2$. Due to the pitch factor p=4, these offloaded multilines may be multilines that will not overlap with any multilines collected following subsequent ultrasound transmit events. The ultrasound device may offload the p multilines wirelessly. In some embodiments, the ultrasound device may truncate the multiline data (e.g., to 10 or 12 bits) prior to offloading. Act 1210 corresponds to stage 1108. The process 1200 then proceeds to act 1212.

In act 1212, the ultrasound device determines if there is another ultrasound transmit event to perform. If there is another ultrasound transmit event to perform, the process 1200 then proceeds to act 1214. If there is not another ultrasound transmit event to perform, the process 1200 then proceeds to act 1216.

In act 1214, the ultrasound device increments i by 1. For example, if i=0, at act 1214 the ultrasound device may increment i to 1. The process 1200 then proceeds back to act 1204 to collect more multilines and update the memory buffer with the new multilines. By incrementing i by 1, the ultrasound device may ensure that multilines produced from a new ultrasound transmit event during the next iteration through the process 1200 will be used to update data in the memory buffer starting with the address directly after the rightmost address from which data was offloaded in act 1210 during the previous iteration through the process 1200. For example, following the example above, if the ultrasound device offloaded data at addresses 5-8 during one iteration through the process 1200, the ultrasound device may update data in the memory buffer starting with address 9 during the next iteration through the process 1200.

In act 1216, if there is not another ultrasound transmit event to perform, the ultrasound device offloads the data at addresses 1 to N of the memory buffer from the ultrasound device. This offloaded data may represent all the remaining multiline data that has not yet been offloaded. The ultrasound device may offload the p multilines wirelessly. In some embodiments, the ultrasound device may truncate the multiline data (e.g., to 10 or 12 bits) prior to offloading. The process 1200 may then terminate.

In some embodiments, the process 1200 may proceed using the addresses described above plus an offset. For example, at act 1206, the ultrasound device may update data at addresses ((p×i) modulo N)+1+z to ((p×i+N−p−1) modulo N)+1+z of the memory buffer by compounding the data at addresses ((p×i) modulo N)+1+z to ((p×i+N−p−1) modulo N)+1+z of the memory buffer with multilines 1 to N−p of the N multilines, where z>0. All other addresses in the process 1200 may be similarly offset by the same z.

While this description has described methods and apparatuses for compounding multilines (a.k.a, A-lines) along a single dimension, it should be appreciated that the same methods may be used to compound ultrasound data, slices, or A-lines along multiple dimensions. For example, these methods and apparatuses may be used for forming three-dimensional ultrasound images.

In some embodiments, the transducers of a wearable ultrasound device (e.g., an ultrasound patch such as that described with reference to FIGS. 1-6) may be arranged in a 1.75-dimensional (1.75d) array. In a 1.75d array, groups of transducers in the elevation direction (e.g., groups of transducers along a column in the transducer array) can be independently controlled to allow for limited steering of ultrasound beams in the elevation direction. In particular, groups of transducers in the elevation direction may share a transmit/receive circuit (e.g., a pulser and a receive amplifier). In some embodiments of a 1.75d array, there may be more transducers along the azimuthal direction than along the elevational direction. Steering in the elevation direction may be helpful for an ultrasound patch because it may enable acquiring ultrasound images from different elevational planes without needing to detach the ultrasound patch from the position and orientation at which the ultrasound patch was adhered to the subject. For example, upon adhering the ultrasound patch to a subject's abdomen, it may be possible to use elevational steering to ensure that data is collected between the subject's ribs.

The inventors have further recognized that it may be helpful for groups of transducers to share a transmit/receive circuit (e.g., a pulser, a receive amplifier, and a switch), rather than each transducer having its own transmit/receive circuit, in order to reduce the size of the ultrasound device. Furthermore, the inventors have recognized that it may be helpful for the number of transducers in each group of transducers that share a transmit/receive circuit to be non-uniform. In particular, one group of transducers in a column sharing a transmit/receive circuit may have a different number of transducers than another group of transducers sharing a transmit/receive circuit. For example, each group in a column in the transducer array may contain fewer or an equal number of transducers compared with groups further towards the center of the column. This may be helpful because certain ultrasound beam profiles require that delays implemented at transducers towards the ends of a column be larger delays than delays implemented at transducers towards the center of a column. Therefore, it may be helpful to more tightly control delays at transducers towards the ends of a column by grouping together smaller numbers of transducers than transducers towards the center of a column.

Figure 13:
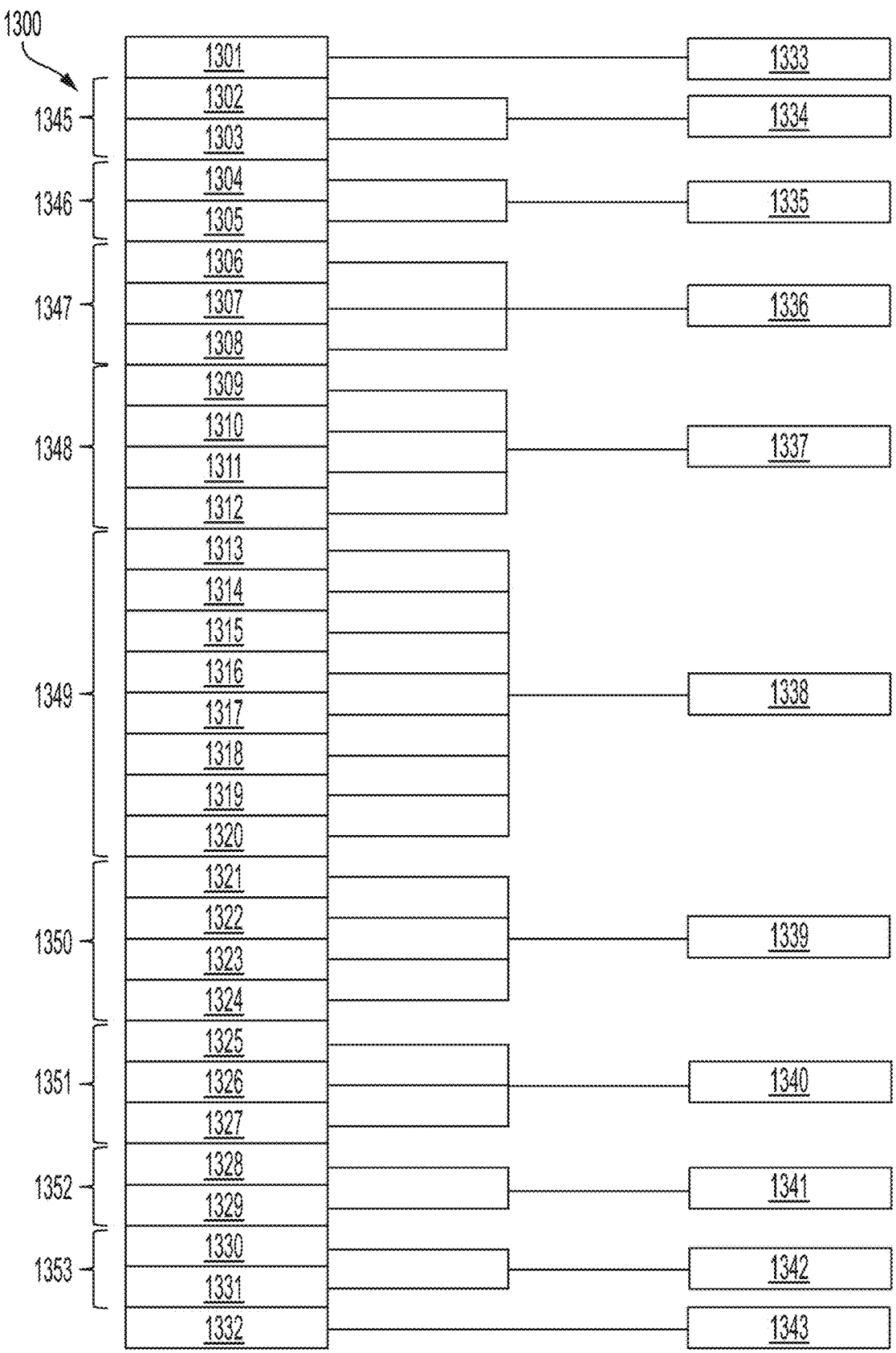
FIG. 13 shows an example of electrically coupling groups of ultrasound transducers within a column of ultrasound transducers to transmit/receive circuits in accordance with certain embodiments described herein.
Figure 15:
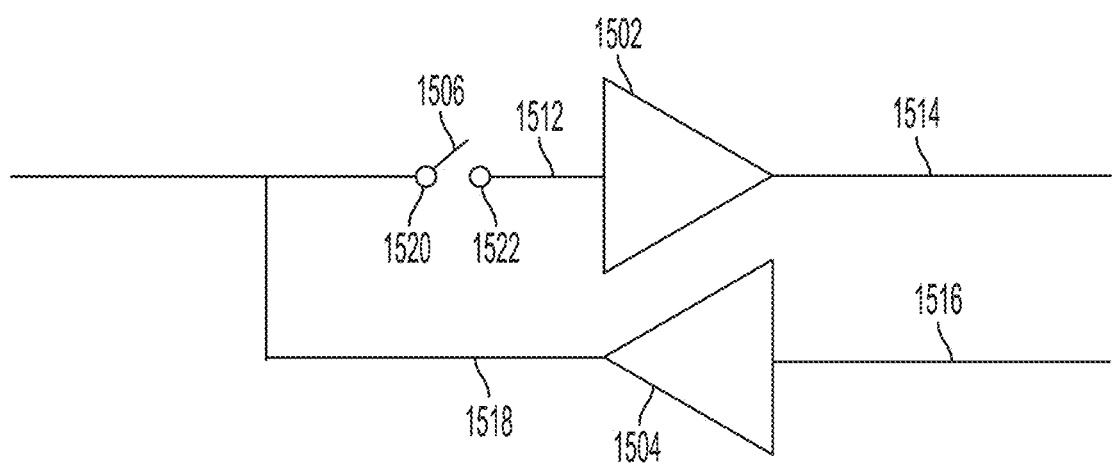
FIG. 15 shows example circuitry that may be included in each of the transmit/receive circuits of FIGS. 13 and 14 in accordance with certain embodiments described herein.

FIG. 13 shows an example of electrically coupling groups of ultrasound transducers within a column 1300 of ultrasound transducers to transmit/receive circuits in accordance with certain embodiments described herein. The column 1300 may be along the elevational direction of an ultrasound transducer array. The column 1300 includes 32 ultrasound transducers 1301-1332, with the ultrasound transducer 1301 disposed at one end of the column 1300 and consecutively numbered ultrasound transducers disposed sequentially one after another until the ultrasound transducer 1332, which is disposed at the other end of the column 1300. FIG. 13 further shows 11 transmit/receive circuits 1333-1343. FIG. 15 shows an example of the circuitry included within each of the transmit/receive circuits 1333-1343.

The ultrasound transducer 1301 is coupled to the transmit/receive circuit 1333. The ultrasound transducers 1302 and 1303 form a group 1345 of ultrasound transducers that are coupled to the transmit/receive circuit 1334. The ultrasound transducers 1304 and 1305 form a group 1346 of ultrasound transducers that are coupled to the transmit/receive circuit 1335. The ultrasound transducers 1306-1308 form a group 1347 of ultrasound transducers that are coupled to the transmit/receive circuit 1336. The ultrasound transducers 1309-1312 form a group 1348 of ultrasound transducers that are coupled to the transmit/receive circuit 1337. The ultrasound transducers 1313-1320 form a group 1349 of ultrasound transducers that are coupled to the transmit/receive circuit 1338. The ultrasound transducers 1321-1324 form a group 1350 of ultrasound transducers that are coupled to the transmit/receive circuit 1339. The ultrasound transducers 1325-1327 form a group 1351 of ultrasound transducers that are coupled to the transmit/receive circuit 1340. The ultrasound transducers 1328 and 1329 form a group 1352 of ultrasound transducers that are coupled to the transmit/receive circuit 1341. The ultrasound transducers 1330 and 1331 form a group 1353 of ultrasound transducers that are coupled to the transmit/receive circuit 1342. The ultrasound transducer 1332 is coupled to the transmit/receive circuit 1343.

It can be seen that each group of ultrasound transducers in the column 1300 that shares a single transmit/receive circuit contains fewer or an equal number of transducers compared with groups further towards the center of the column 1300. In particular, the group 1349 contains eight ultrasound transducers and is the centermost group of ultrasound transducers in the column 1300. The groups 1348 and 1350 each contain four ultrasound transducers which is fewer transducers than in the group 1349, which is further towards the center of the column 1300. The groups 1347 and 1351 each contain three ultrasound transducers which is fewer transducers than in the groups 1348-1350, which are further towards the center of the column 1300. The groups 1346 and 1352 each contain two ultrasound transducers which is fewer transducers than in the groups 1347-1351, which are further towards the center of the column 1300. The groups 1345 and 1353 each contain two ultrasound transducers which is fewer transducers than or an equal number of transducers as in the groups 1346-1352, which are further towards the center of the column 1300. The ultrasound transducers 1301 and 1332 are each connected to a transmit/receive circuit that is coupled to only one ultrasound transducer. According, the ultrasound transducers 1301 and 1332 may be considered to constitute groups of one ultrasound transducer, which is fewer transducers than in the groups 1345-1353, which are further towards the center of the column 1300. As is evident from FIG. 13, the number of ultrasound transducers per group is symmetric about the center of the column 1300 (i.e., proceeding from one end of the column 1300 to the other end, the number of ultrasound transducers per group is 1, 2, 2, 3, 4, 8, 4, 3, 2, 2, 1).

It should be appreciated that other groupings are ultrasound transducers are possible. For example, the number of ultrasound transducers per group may still be symmetric about the center of the column 1300, but there may be different numbers of ultrasound transducers in each group compared with the groups shown in FIG. 13). As another example, there may be a different number of groups of ultrasound transducers (i.e., a different number of groups than 11, which is how many groups are shown in the example of FIG. 13). As another example, each group may have the same number of ultrasound transducers (e.g., two or eight ultrasound transducers in each group).

It should be appreciated that while the above description refers to transducers along the elevational direction being arranged in a column, in some embodiments transducers along the elevational direction may be arranged in a row.

Figure 14:
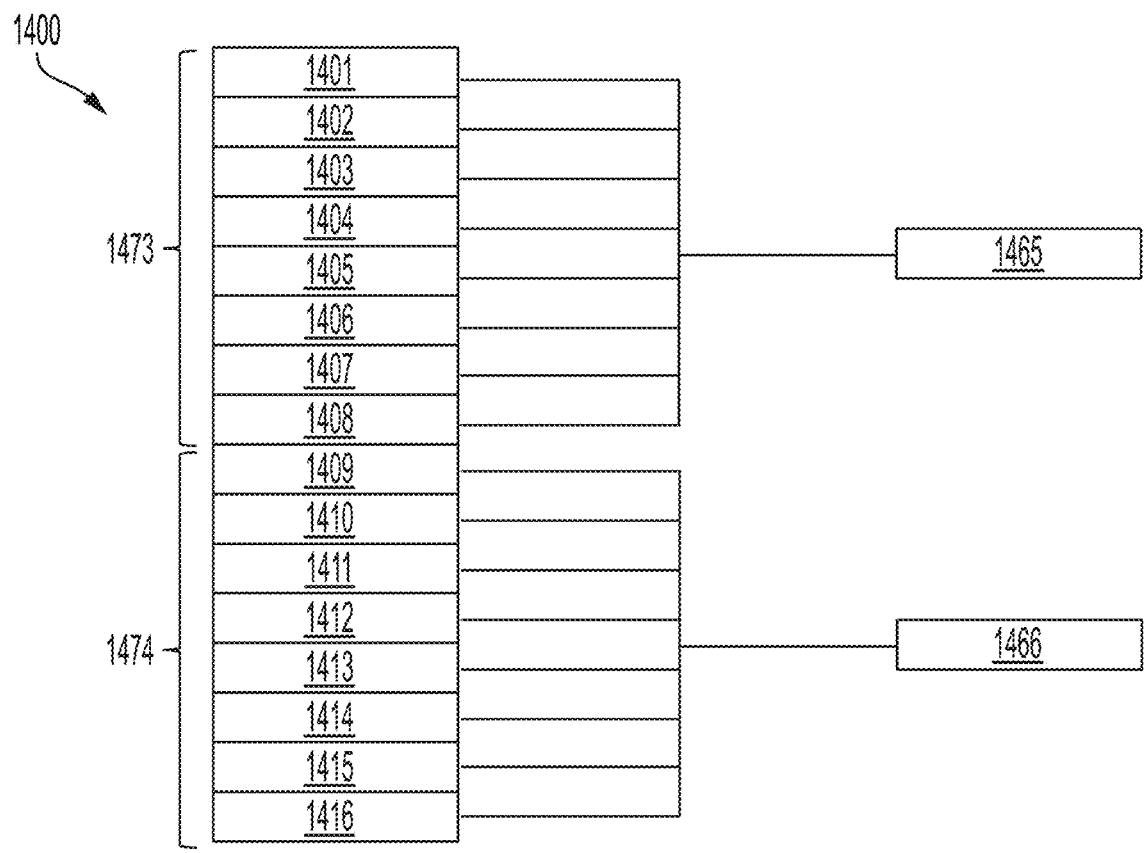
FIG. 14 shows an example of electrically coupling groups of ultrasound transducers within a column of ultrasound transducers to transmit/receive circuits in accordance with certain embodiments described herein.
Figure 14:
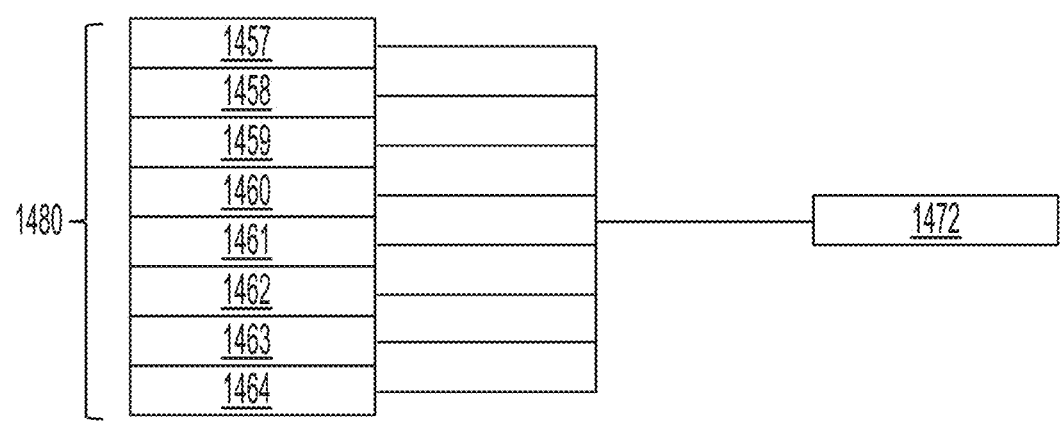

FIG. 14 shows an example of electrically coupling groups of ultrasound transducers within a column 1400 of ultrasound transducers to transmit/receive circuits in accordance with certain embodiments described herein. The column 1400 may be along the elevational direction of an ultrasound transducer array. The column 1400 includes 64 ultrasound transducers 1401-1464 (not all of which are shown in FIG. 14), with the ultrasound transducer 1401 disposed at one end of the column 1400 and consecutively numbered ultrasound transducers disposed sequentially one after another until the ultrasound transducer 1464, which is disposed at the other end of the column 1400. FIG. 14 further illustrates 8 transmit/receive circuits 1465-1472 (not all of which are shown explicitly in FIG. 14). FIG. 15 shows an example of the circuitry included within each of the transmit/receive circuits 1465-1472.

The ultrasound transducers 1401-1408 form a group 1473 of ultrasound transducers that are coupled to the transmit/receive circuit 1465. The ultrasound transducers 1409-1416 form a group 1474 of ultrasound transducers that are coupled to the transmit/receive circuit 1466. The ultrasound transducers 1417-1424 form a group 1475 of ultrasound transducers that are coupled to the transmit/receive circuit 1467. The ultrasound transducers 1425-1432 form a group 1476 of ultrasound transducers that are coupled to the transmit/receive circuit 1468. The ultrasound transducers 1433-1440 form a group 1477 of ultrasound transducers that are coupled to the transmit/receive circuit 1469. The ultrasound transducers 1441-1448 form a group 1478 of ultrasound transducers that are coupled to the transmit/receive circuit 1470. The ultrasound transducers 1449-1456 form a group 1479 of ultrasound transducers that are coupled to the transmit/receive circuit 1471. The ultrasound transducers 1457-1464 form a group 1480 of ultrasound transducers that are coupled to the transmit/receive circuit 1472.

It can be seen that each group of ultrasound transducers in the column 1400 contains the same number of transducers. In the example of FIG. 14, this number is 8, but other numbers of transducers per group are possible (e.g., 1, 2, 4, etc.). A column 1400 having an equal number of ultrasound transducers per group may be helpful for forming three-dimensional ultrasound images, for example.

It should be appreciated that while the above description of FIGS. 13 and 14 refers to transducers along the elevational direction being arranged in a column, in some embodiments transducers along the elevational direction may be arranged in a row. It should also be noted that in some embodiments, it may be possible to switch any of the transducers in FIGS. 13 and 14 on or off, and it may be possible to switch the polarity of any of the transducers in FIGS. 13 and 14. For further description of switches that may be used in combination with the transducers may be found in U.S. patent application Ser. No. 14/957,051 titled "ULTRASOUND RECEIVER CIRCUITRY AND RELATED APPARATUS AND METHODS," filed on Dec. 2, 2015 (and assigned to the assignee of the instant application), which is incorporated by reference herein in its entirety.

FIG. 15 shows example circuitry that may be included in one or more (e.g., each) of the transmit/receive circuits 1333-1343 and 1465-1472 in accordance with certain embodiments described herein. The circuitry includes a receive amplifier (e.g., a transimpedance amplifier) 1502, a pulser 1504, and a switch 1506. The receive amplifier 1502 includes an input 1512 and an output 1514. The pulser 1504 includes an input 1516 and an output 1518. The switch 1506 includes a first port 1520 and a second port 1522. The input 1512 of the receive amplifier 1502 is electrically coupled to the second port 1522 of the switch 1506. The output 1518 of the pulser 1504 is electrically coupled to the first port 1520 of the switch 1506. When the switch 1506 is closed, the first port 1520 and the second port 1522 of the switch are electrically coupled together. When the switch 1506 is open, the first port 1520 and the second port 1522 of the switch are electrically isolated from each other.

The output 1518 of the pulser 1504 and the first port 1520 of the switch 1506 may be electrically coupled to one or more of the ultrasound transducers (not shown in figure, e.g., any of the ultrasound transducers 1301-1332 and 1401-1464). The output 1514 of the receive amplifier 1502 may be coupled to a portion of an analog processing block, such as an averaging circuit. The input 1516 of the pulser may be electrically coupled to a waveform generating circuit (not shown in figure).

In operation, the pulser 1504 may be configured to output (through the output 1518) a driving signal to one or more ultrasound transducers (e.g., any of the ultrasound transducers 1301-1332 and 1401-1464). The pulser 1504 may receive a waveform from a waveform generating circuit (not shown) and be configured to output a driving signal corresponding to the received waveform. When the pulser 1504 is driving the ultrasound transducers (the "transmit phase"), the switch 1506 may be open such that the driving signal is not applied to the receive amplifier 1502. The ultrasound transducers may be configured to emit pulsed ultrasound signals into a structure, such as a patient, in response to the driving signal received from the pulser 1504. The pulsed ultrasonic signals may be back-scattered from structures in the body, such as blood cells or muscular tissue, to produce echoes that return to the ultrasound transducers. The ultrasound transducers may be configured to convert these echoes into electrical signals. When the ultrasound transducers are receiving the echoes (the "receive phase"), the switch 1506 may be closed such that the ultrasound transducers may transmit the electrical signals representing the received echoes to the receive amplifier 1502.

Imaging a subject using an ultrasound patch that adheres to the subject, rather than using a conventional ultrasound probe, may be helpful for a number of reasons. An ultrasound patch may remain adhered to a patient and may therefore allow for easier continuous imaging and monitoring with ultrasound than monitoring with a probe, which requires another individual to constantly hold the probe on the patient. Continuous monitoring may be helpful in cases where real-time, continuous information from ultrasound imaging is required, as opposed to after-the-fact or periodic information. In a similar vein, because the ultrasound patch may remain adhered to a subject for an extended period of time, the ultrasound patch may be used for long-term imaging and monitoring with ultrasound. Long-term monitoring may refer to any period of time that is longer than a conventional ultrasound imaging session with a conventional ultrasound probe, and may be minutes, hours, days, weeks, months, or years, as examples. Long-term monitoring may be useful in cases where it is not known when a particular event (e.g., an adverse physiological event) may occur. Furthermore, the ultrasound patch may collect data from a subject outside of a medical setting, such as in the subject's home. It should be appreciated that using the processes described with reference to FIGS. 8-12, the ultrasound device may perform continuous and/or long-term monitoring of medical indications by wirelessly offloading ultrasound data sufficient to construct an ultrasound image therefrom. In particular, the ultrasound device may be configured to wirelessly offload ultrasound data sufficient to construct an ultrasound image containing information indicative of a medical indication. Offloading data sufficient to construct an ultrasound image may be helpful because an ultrasound image may provide more information than a transmitted alarm signal or metric, and because this allows a medical professional to view the ultrasound image. For example, ultrasound data may contain an unexpected indication that a conventional device is not programmed to automatically detect. By offloading data sufficient to construct a full ultrasound image, a medical professional may be able to detect the unexpected indication upon viewing the ultrasound image. Additionally, automatic determination of conditions and metrics may be more prone to error than a medical professional performing the determination based on ultrasound images.

There are numerous indications for which continuous and/or long-term monitoring with an ultrasound patch may be helpful. The following is a non-limiting list of example indications.

1. An event may occur that may cause changes in a subject's body during a period of time following the event. Accordingly, after the event occurs, an ultrasound patch may be adhered to the subject for a period of time to monitor for those changes using ultrasound imaging. As specific examples, a subject may be monitored for healing after surgery, for a response to a drug after initiation of a drug delivery regimen, for adverse physiological events following an invasive procedure (e.g., after placement of a stent or for embedding a pacemaker), or for a response to cancer therapy. Types of cancer therapies to monitor may include brachytherapy, radiation therapy (e.g., x-rays, gamma rays, charged particles targeting cancer), chemotherapy, immunotherapy, targeted therapy (e.g., small-molecule drugs or monoclonal antibodies), hormone therapy, post-therapy recovery (e.g., after stem cell transplant), genetic-guided precision medicine (e.g., DNA sequencing, genomic testing, molecular profiling, or tumor profiling), and high intensity focused ultrasound therapy (HIFU); 2. An individual at risk for a particular adverse event may be monitored for that event. For example, an individual with cancer that is considered susceptible to metastasis (whether before or after surgery) may be monitored for metastasis, fetal development may be monitored (e.g., by monitoring fetal heart, head, femur, or other organ size) in individuals with high risk pregnancies (e.g., history of miscarriage, or possible drug side effects in fetal development), or viability of a transplanted organ may be monitored. Other individuals who may be at risk for adverse events may include individuals with peripheral artery disease, diabetes, or those who have undergone heart bypass surgery; 3. Complications during surgery may be monitored in a patient by monitoring certain physiological parameters (e.g., cardiac function parameters) in real-time; 4. The location and/or trajectory of an instrument (e.g., a needle, catheter, or stent) being placed within a patient before a surgical procedure may be monitored in real-time; 5. Certain physiological parameters (e.g., left ventricular wall motion) may be monitored during a stress exercise in real-time.

It should be appreciated that any indication for which conventional ultrasound imaging is used may be able to be monitored with an ultrasound patch. In particular, for any indication that can be detected by placing a conventional ultrasound probe at a specific location on a subject with a specific orientation relative to the subject and acquiring an image using specific imaging parameters (e.g., frequency), that indication may be monitored by adhering the ultrasound patch to the specific location on the subject with the specific orientation relative to the subject and configuring the ultrasound patch to acquire images using the specific imaging parameters. The ultrasound patch may further be configured to acquire images continuously or with a specific period, and left on the subject for a period of time (e.g., minutes, hours, days, weeks, months, or years). The ultrasound patch may be configured to wirelessly offload ultrasound data to an electronic device. In some embodiments, the ultrasound patch may be configured to wirelessly offload the ultrasound data to an electronic device such as a smartphone, tablet, or lapto p configured to generate ultrasound images from the ultrasound data and display the ultrasound images. In some embodiments, the ultrasound patch may be configured to wirelessly offload the ultrasound data to one or remote servers (a.k.a., a "cloud" configuration). The one or more remote servers may be configured to generate ultrasound images from the ultrasound data and to transmit the ultrasound images to an electronic device such as a smartphone, tablet, or lapto p configured to display the ultrasound images in real-time. Alternatively or additionally, the one or more remote servers may be configured to transmit the ultrasound images to an electronic device such as a smartphone, tablet, or lapto p configured to generate ultrasound images from the ultrasound data and display the ultrasound images. The electronic device may be configured to generate the ultrasound images in real-time. This may be helpful, for example, for real-time monitoring for complications during surgery or for real-time monitoring of instrument placement. As another example, a medical professional may use the electronic device to access the ultrasound images not in real time. For example, the ultrasound images may be downloaded to the electronic device, or transmitted to the electronic device in an email or text message, and the medical professional may access the ultrasound images at a time after the ultrasound data was collected. As another example, the medical professional may actively download ultrasound images from the one or more remote servers (e.g., by accessing a website) at a time after the ultrasound data was collected. This may be helpful in situations where real-time feedback is not critical, for example, monitoring a subject for healing after surgery, for a response to a drug after initiation of a drug delivery regimen, for adverse physiological events following an invasive procedure, or for a response to cancer therapy. Additional examples in which real-time feedback is not critical include monitoring cancer for metastasis, fetal development, organ viability, and stress exercise. The medical professional may follow up with the subject with feedback after viewing the ultrasound images.

The following is a description of specific indications which the ultrasound patch may monitor. In particular, the ultrasound patch may be configured to wirelessly offload ultrasound data sufficient to construct an ultrasound image containing information indicative of these indications. In some embodiments, the ultrasound patch may be used to monitor tumor size and/or shape. For further description of tumor size/shape and ultrasound imaging, see Fornage, Bruno D., Olivier Toubas, and Michel Morel, "Clinical, mammographic, and sonographic determination of preoperative breast cancer size," *Cancer* 60.4 (1987): 765-771; Ahuja, A. T., et al., "Ultrasound of malignant cervical lymph nodes," *Cancer Imaging* 8.1 (2008): 48; and Jalaguier-Coudray, A., and J. Thomassin-Piana, "Solid masses: what are the underlying histo pathological lesions?" *Diagnostic and interventional imaging* 95.2 (2014): 153-168, which are incorporated by reference herein in their entireties.

In some embodiments, the ultrasound patch may be used to monitor tumor elasticity. For further description of tumor elasticity and ultrasound imaging, see Garra, Brian S., "Tissue elasticity imaging using ultrasound," *Applied radiology* 40.4 (2011): 24 and Grajo, Joseph R., and Richard G. Barr, "Compression elasticity imaging of the breast: an overview," *Applied Radiology* 41.10 (2012): 18, which are incorporated by reference herein in their entireties.

In some embodiments, the ultrasound patch may be used to monitor tumor vascularity. For further description of tumor vascularity and ultrasound imaging, see Park, Ah Young, et al., "An innovative ultrasound technique for evaluation of tumor vascularity in breast cancers: superb micro-vascular imaging," *Journal of breast cancer* 19.2 (2016): 210-213; Schroeder, Ralf-Juergen, et al., "Role of power Doppler techniques and ultrasound contrast enhancement in the differential diagnosis of focal breast lesions," *European radiology* 13.1 (2003): 68-79; and Gokhale, Sudheer, "Ultrasound characterization of breast masses," *The Indian journal of radiology & imaging* 19.3 (2009): 242, which are incorporated by reference herein in their entireties.

In some embodiments, the ultrasound patch may be used to monitor bladder fullness and/or volume, particularly in individuals with dysfunctional voiding. For further description of bladder fullness/volume and ultrasound imaging, see van Leuteren, P. G., et al., "URIKA, continuous ultrasound monitoring for the detection of a full bladder in children with dysfunctional voiding: a feasibility study," *Biomedical Physics & Engineering Express* 3.1 (2017): 017005 and Dicuio, Mauro, et al., "Measurements of urinary bladder volume: comparison of five ultrasound calculation methods in volunteers," Arch Ital Urol Androl 77.1 (2005): 60-62, which are incorporated by reference herein in their entireties.

In some embodiments, the ultrasound patch may be used to monitor for bladder outlet obstruction. For further description of bladder outlet obstruction and ultrasound imaging, see Arif, Muhammad, et al., "Noninvasive Diagnosis of Bladder Outlet Obstruction in Patients with Lower Urinary Tract Symptoms Using Ultrasound Decorrelation Analysis," *The Journal of urology* 196.2 (2016): 490-497; Manieri, Carlo, et al., "The diagnosis of bladder outlet obstruction in men by ultrasound measurement of bladder wall thickness," *The Journal of urology* 159.3 (1998): 761-765; Han, Deok Hyun, et al., "The diagnostic efficacy of 3-dimensional ultrasound estimated bladder weight corrected for body surface area as an alternative nonurodynamic parameter of bladder outlet obstruction," *The Journal of urology* 185.3 (2011): 964-969; Kessler, Thomas M., et al., "Ultrasound assessment of detrusor thickness in men—can it predict bladder outlet obstruction and replace pressure flow study?" *The Journal of urology* 175.6 (2006): 2170-2173; Franco, Giorgio, et al., "Ultrasound assessment of intravesical prostatic protrusion and detrusor wall thickness—new standards for noninvasive bladder outlet obstruction diagnosis?" *The Journal of urology* 183.6 (2010): 2270-2274; and Bright, Elizabeth, et al., "Ultrasound estimated bladder weight and measurement of bladder wall thickness—useful noninvasive methods for assessing the lower urinary tract?" *The Journal of urology* 184.5 (2010): 1847-1854, which are incorporated by reference herein in their entireties.

In some embodiments, the ultrasound patch may be used to monitor pulse wave velocity and/or blood pressure. For further description of pulse wave velocity, blood pressure, and ultrasound imaging, see Seo, Joohyun, et al., "Noninvasive arterial blood pressure waveform monitoring using two-element ultrasound system," *IEEE transactions on ultrasonics, ferroelectrics, and frequency control* 62.4 (2015): 776-784 and Luo, Jianwen, Ronny X. Li, and Elisa E. Konofagou, "Pulse wave imaging of the human carotid artery: an in vivo feasibility study," *IEEE transactions on ultrasonics, ferroelectrics, and frequency control* 59.1 (2012): 132-181, which are incorporated by reference herein in their entireties.

In some embodiments, the ultrasound patch may be used to monitor inferior vena cava (IVC) diameter. For further description of IVC diameter and ultrasound imaging, see Goldflam, Katja, Turan Saul, and Resa Lewiss, "Focus on: inferior vena cava ultrasound," *ACEP News* 6 (2011): 24-25, which is incorporated by reference herein in its entirety.

In some embodiments, the ultrasound patch may be used to monitor IVC volume. For further description of IVC volume and ultrasound imaging, see Pershad, Jay, et al., "Bedside limited echocardiography by the emergency physician is accurate during evaluation of the critically ill patient." *Pediatrics* 114.6 (2004): e667-e671, which is incorporated by reference herein in its entirety.

In some embodiments, the ultrasound patch may be used to monitor IVC collapsibility. IVC collapsibility may be calculated by measuring maximum IVC diameter ($IVC_{max}$) and minimum IVC diameter ($IVC_{min}$) and calculating IVC collapsibility as ($IVC_{max}-IVC_{min}$)/$IVC_{max} \times 100$. $IVC_{min}$ may be measured at the end of inspiration and $IVC_{max}$ may be measured at the end of expiration. For further description of IVC collapsibility and ultrasound imaging, see Brennan, J. Matthew, et al., "Handcarried ultrasound measurement of the inferior vena cava for assessment of intravascular volume status in the outpatient hemodialysis clinic," *Clinical Journal of the American Society of Nephrology* 1.4 (2006): 749-753, which is incorporated by reference herein in its entirety.

In some embodiments, the ultrasound patch may be used to monitor IVC blood flow rate. For further description of IVC blood flow rate and ultrasound imaging, see Indik, Julia H., Victor Chen, and Kathryn L. Reed, "Association of umbilical venous with inferior vena cava blood flow velocities," *Obstetrics & Gynecology* 77.4 (1991): 551-557, which is incorporated by reference herein in its entirety.

In some embodiments, the ultrasound patch may be used to monitor IVC wall motion. For further description of IVC wall motion and ultrasound imaging, see Gullace, G., and M. T. Savoia, "Echocardiographic assessment of the inferior vena cava wall motion for studies of right heart dynamics and function," *Clinical cardiology* 7.7 (1984): 393-404, which is incorporated by reference herein in its entirety.

It should be appreciated that description of monitoring diameter, volume, blood flow rate, and wall motion of the IVC using ultrasound imaging may also be relevant to monitoring diameter, volume, blood flow rate, and wall motion of other blood vessels.

In some embodiments, the ultrasound patch may be used to monitor intravascular volume. For further description of intravascular volume and ultrasound imaging, see Brennan, J. Matthew, et al., "Handcarried ultrasound measurement of the inferior vena cava for assessment of intravascular volume status in the outpatient hemodialysis clinic.," *Clinical Journal of the American Society of Nephrology* 1.4 (2006): 749-753, which is incorporated by reference herein in its entirety.

In some embodiments, the ultrasound patch may be used to monitor left ventricular wall motion. For further description of left ventricular wall motion and ultrasound imaging, see Nakashiki, Kenichi, et al., "Usefulness of a novel ultrasound transducer for continuous monitoring treadmill exercise echocardiography to assess coronary artery disease," *Circulation Journal* 70.10 (2006): 1297-1302, which is incorporated by reference herein in its entirety.

In some embodiments, the ultrasound patch may be used to monitor cardiac output. For further description of cardiac output and ultrasound imaging, see Haude, M., et al., "Continuous and Noninvasive Monitoring of Cardiac Output by Transesophageal Doppler Ultrasound," *Transesophageal Echocardiography: A New Window to the Heart* (1989): 260, which is incorporated by reference herein in its entirety.

In some embodiments, the ultrasound patch may be used to monitor ejection fraction. For further description of ejection fraction and ultrasound imaging, see Quiñones, Miguel A., et al., "A new, simplified and accurate method for determining ejection fraction with two-dimensional echocardiography," *Circulation* 64.4 (1981): 744-753, which is incorporated by reference herein in its entirety.

In some embodiments, the ultrasound patch may be used to monitor central venous pressure. For further description of central venous pressure and ultrasound imaging, see Lipton, Bruce, "Estimation of central venous pressure by ultrasound of the internal jugular vein," *The American journal of emergency medicine* 18.4 (2000): 432-434 and Baumann, Ulrich A., et al., "Estimation of central venous pressure by ultrasound," *Resuscitation* 64.2 (2005): 193-199, which is incorporated by reference herein in its entirety.

In some embodiments, the ultrasound patch may be used to monitor peripheral blood flow rate. For further description of peripheral blood flow and ultrasound imaging, see Wladimiroff, J. W., H. M. Tonge, and P. A. Stewart, "Doppler ultrasound assessment of cerebral blood flow in the human fetus," *BJOG: An International Journal of Obstetrics & Gynaecology* 93.5 (1986): 471-475), which is incorporated by reference herein in its entirety.

In some embodiments, the ultrasound patch may be used to monitor for abdominal aortic aneurysm. For further description of abdominal aortic aneurysm and ultrasound imaging, see Wu, Stanley, et al. "Focus on: bedside ultrasound of the abdominal aorta." *ACEP News* (2010) and Creditt, Angela B., and Michael Joyce, "Abdominal Aortic Aneurysm Ultrasound," *Clinical Ultrasound*. Springer, Cham, 2018. 135-147, which are incorporated by reference herein in their entireties.

In some embodiments, the ultrasound patch may be used to monitor for deep vein thrombosis. For further description of deep vein thrombosis and ultrasound imaging, see Lensing, Anthonie W A, et al., "Detection of deep-vein thrombosis by real-time B-mode ultrasonography," *New England Journal of Medicine* 320.6 (1989): 342-345, which is incorporated by reference herein in its entirety.

In some embodiments, the ultrasound patch may be used to monitor fetal heartbeat. For further description of fetal heartbeat and ultrasound imaging, see Rakhmetova, Assel, *Ultrasound Transducer Design for Continuous Fetal Heartbeat Monitoring*, MS thesis, Høgskolen i Sørøst-Norge, 2016, which is incorporated by reference herein in its entirety.

In some embodiments, the ultrasound patch may be used to monitor for pregnancy. For further description of pregnancy and ultrasound imaging, see Batzer, Frances R., et al., "Landmarks during the first forty-two days of gestation demonstrated by the β-subunit of human chorionic gonadotropin and ultrasound," *American journal of obstetrics and gynecology* 146.8 (1983): 973-979, which is incorporated by reference herein in its entirety.

In some embodiments, the ultrasound patch may be used to monitor follicle growth in ovaries. For further description of follicle growth in ovaries and ultrasound imaging, see Queenan, John T., et al., "Ultrasound scanning of ovaries to detect ovulation in women," *Fertility and sterility* 34.2 (1980): 99-105 and Adams, J., et al., "Multifollicular ovaries: clinical and endocrine features and response to pulsatile gonadotropin releasing hormone," *The Lancet* 326.8469-8470 (1985): 1375-1379, which are incorporated by reference herein in their entireties.

In some embodiments, the ultrasound patch may be used to monitor for dehydration using ultrasound imaging of the IVC. For further description of dehydration and ultrasound imaging, see Modi, Payal, et al., "Accuracy of inferior vena cava ultrasound for predicting dehydration in children with acute diarrhea in resource-limited settings," *PloS one* 11.1 (2016): e0146859 and Chen, Lei, et al. "Use of bedside ultrasound to assess degree of dehydration in children with gastroenteritis." *Academic Emergency Medicine* 17.10 (2010): 1042-1047, which are incorporated by reference herein in their entireties.

In some embodiments, the ultrasound patch may be used to monitor skin moisturization. For further description of skin moisturization, see Mlosek, Robert K., et al., "The use of high frequency ultrasound imaging in skin moisturization measurement," *Skin Research and Technology* 19.2 (2013): 169-175, which is incorporated by reference herein in its entirety.

In some embodiments, the ultrasound patch may be used to monitor amniotic fluid volume. For further description of amniotic fluid volume and ultrasound imaging, see Rutherford, Susan E., et al., "The four-quadrant assessment of amniotic fluid volume: an adjunct to antepartum fetal heart rate testing," *Obstetrics & Gynecology* 70.3 (1987): 353-356; Phelan, J. P., et al., "Amniotic fluid volume assessment with the four-quadrant technique at 36-42 weeks' gestation," *The Journal of reproductive medicine* 32.7 (1987): 540-542; Magann, E. F., et al., "Ultrasound estimation of amniotic fluid volume using the largest vertical pocket containing umbilical cord: measure to or through the cord?" *Ultrasound in obstetrics & gynecology* 20.5 (2002): 464-467; Phelan, J. P., et al., "Polyhydramnios and perinatal outcome," *Journal of perinatology: official journal of the California Perinatal Association* 10.4 (1990): 347-350; and Patrelli, Tito Silvio, et al., "Maternal Hydration Therapy Improves the Quantity of Amniotic Fluid and the Pregnancy Outcome in Third-Trimester Isolated Oligohydramnios," *Journal of Ultrasound in Medicine* 31.2 (2012): 239-244, which are incorporated by reference herein in their entireties.

In some embodiments, the ultrasound patch may be used to monitor for pneumonia. For further description of pneumonia and ultrasound imaging, see Wang, Guyi, et al. "Lung ultrasound: a promising tool to monitor ventilator-associated pneumonia in critically ill patients," *Critical Care* 20.1 (2016): 320, which is incorporated by reference herein in its entirety.

In some embodiments, the ultrasound patch may be used to monitor for pleural effusion. For further description of pleural effusion and ultrasound imaging, see Prina, Elena, Antoni Torres, and Carlos Roberto Ribeiro Carvalho, "Lung ultrasound in the evaluation of pleural effusion." *Jornal Brasileiro de Pneumologia* 40.1 (2014): 1-5, which is incorporated by reference herein in its entirety.

In some embodiments, the ultrasound patch may be used to monitor for pneumothorax. For further description of pneumothorax and ultrasound imaging, see Husain, Lubna F., et al., "Sonographic diagnosis of pneumothorax," *Journal of emergencies, trauma, and shock* 5.1 (2012): 76, which is incorporated by reference herein in its entirety.

In some embodiments, the ultrasound patch may be used to monitor for chronic obstructive pulmonary disease (COPD). For further description of COPD and ultrasound imaging, see Lichtenstein, D., and G. Meziere. "A lung ultrasound sign allowing bedside distinction between pulmonary edema and COPD: the comet-tail artifact." *Intensive care medicine* 24.12 (1998): 1331-1334, which is incorporated by reference herein in its entirety.

In some embodiments, the ultrasound patch may be used to monitor lung volume. For further description of lung volume and ultrasound imaging, see Pohls, U. G., and A. Rempen, "Fetal lung volumetry by three-dimensional ultrasound," *Ultrasound in obstetrics & gynecology* 11.1 (1998): 6-12, which is incorporated by reference herein in its entirety.

In some embodiments, the ultrasound patch may be used to monitor enteral feeding tube placement. For further description of enteral feeding tube placement and ultrasound imaging, see Gubler, C., et al., "Bedside sonographic control for positioning enteral feeding tubes: a controlled study in intensive care unit patients," *Endoscopy* 38.12 (2006): 1256-1260 and Nedel, Wagner Luis, Mariana Nunes Ferreira Jost, and João Wilney Franco Filho, "A simple and fast ultrasonographic method of detecting enteral feeding tube placement in mechanically ventilated, critically ill patients," *Journal of intensive care* 5.1 (2017): 55, which are incorporated by reference herein in their entireties.

In some embodiments, the ultrasound patch may be used to monitor gastric emptying. For further description of gastric emptying and ultrasound imaging, see Darwiche, Gassan, et al., "Measurement of gastric emptying by standardized real-time ultrasonography in healthy subjects and diabetic patients," *Journal of Ultrasound in Medicine* 18.10 (1999): 673-682 and Bateman, D. N., and T. A. Whittingham, "Measurement of gastric emptying by real-time ultrasound," *Gut* 23.6 (1982): 524-527, which are incorporated by reference herein in their entireties.

In some embodiments, the ultrasound patch may be used to monitor for indigestion. Studies have been performed on detecting indigestion using electrogastrography (EGG). If both EGG and ultrasound imaging are simultaneously performed, the EGG results may be correlated with the ultrasound imaging to enable detection and monitoring of indigestion using ultrasound imaging. For further description of indigestion and electrogastrography, see Van der Voort, I. R., et al., "Electrogastrography as a diagnostic tool for delayed gastric emptying in functional dyspepsia and irritable bowel syndrome," *Neurogastroenterology & Motility* 15.5 (2003): 467-473, which is incorporated by reference herein in its entirety.

In some embodiments, the ultrasound patch may be used to monitor kidney function. For further description of kidney function and ultrasound imaging, see Ikee, Ryota, et al., "Correlation between the resistive index by Doppler ultrasound and kidney function and histology," *American Journal of Kidney Diseases* 46.4 (2005): 603-609 and Petersen, L. J., et al. "The pulsatility index and the resistive index in renal arteries. Associations with long-term progression in chronic renal failure," *Nephrology, dialysis, transplantation: official publication of the European Dialysis and Transplant Association-European Renal Association* 12.7 (1997): 1376-1380, which are incorporated by reference herein in their entireties.

In some embodiments, the ultrasound patch may be used to monitor renal blood flow rate. For further description of renal blood flow rate and ultrasound imaging, see Wei, Kevin, et al., "Quantification of renal blood flow with contrast-enhanced ultrasound," *Journal of the American College of Cardiology* 37.4 (2001): 1135-1140s, which is incorporated by reference herein in its entirety.

In some embodiments, the ultrasound patch may be used to monitor needle placement during pericardiocentesis. For further description of needle placement during pericardiocentesis and ultrasound imaging, see Chandraratna, P. A. N., et al., "'Hands-Free' Continuous Transthoracic Monitoring of Pericardiocentesis Using a Novel Ultrasound Transducer," *Echocardiography* 20.6 (2003): 491-494, which is incorporated by reference herein in its entirety.

In some embodiments, the ultrasound patch may be used to monitor needle placement during amniocentesis. For further description of needle placement during amniocentesis and ultrasound imaging, see Milunsky, Aubrey, and Jeff M. Milunsky, *Genetic disorders and the fetus: diagnosis, prevention, and treatment*, John Wiley & Sons, 2015, which is incorporated by reference herein in its entirety.

In some embodiments, the ultrasound patch may be used to monitor for vasospasm. For further description of vasospasm and ultrasound imaging, see Lee, Benjamin, "Signal processing techniques for operator independent Doppler ultrasound: potential for use in transcranial Doppler ultrasound," MS Thesis, Ryerson University, 2011), which is incorporated by reference herein in its entirety.

In some embodiments, the ultrasound patch may be used to monitor high-intensity focused ultrasound ablation. For further description of high-intensity focusing ultrasound ablation and ultrasound imaging, see Grondin, Julien, et al., "Real-time monitoring of high intensity focused ultrasound (HIFU) ablation of in vitro canine livers using harmonic motion imaging for focused ultrasound (HMIFU)," *Journal of visualized experiments: JoVE* 105 (2015), which is incorporated by reference herein in its entirety.

In some embodiments, the ultrasound patch may be used to monitor drug delivery. For further description of drug delivery and ultrasound imaging, see Payen, T., and S. L. Bridal, "Ultrasonic strategies to monitor drug delivery," *Journal of Drug Delivery Science and Technology* 23.1 (2013): 47-56 and Coussios, C. C., et al., "Role of acoustic cavitation in the delivery and monitoring of cancer treatment by high-intensity focused ultrasound (HIFU)," *International Journal of Hyperthermia* 23.2 (2007): 105-120, which are incorporated by reference herein in their entireties.

In some embodiments, the ultrasound patch may be used to monitor hemodialysis access. For further description of hemodialysis access and ultrasound imaging, see Finlay, David E., et al., "Duplex and Color Doppler Sonography of hemodialysis arteriovenous fistulas and grafts," *Radiographics* 13.5 (1993): 983-989 and Teodorescu, Victoria, Susan Gustayson, and Harry Schanzer, "Duplex ultrasound evaluation of hemodialysis access: a detailed protocol," *International journal of nephrology* 2012 (2012), which are incorporated by reference herein in their entireties.

In some embodiments, the ultrasound patch may be used to monitor the vascular system, the liver, the gallbladder, the biliary system, the spleen, the pancreas, the gastrointestinal tract, the peritoneal cavity and abdominal wall, the urinary system, the retroperitoneum, the breast, the thyroid and parathyroid glands, the scrotum, the musculoskeletal system, the neonatal and pediatric abdomen, the neonatal and pediatric adrenal and urinary system, the neonatal and infant head, the infant and pediatric hip, the neonatal and infant spine, the thoracic cavity, the cerebrovascular system, the female pelvis, the uterus, the ovaries, the adnexa, obstetric measurements, gestational age, fetal growth, fetal congenital abnormalities, the placenta, the umbilical cord, amniotic fluid, fetal membranes, fetal hydrops, the fetal face and neck, the fetal neural axis, the fetal thorax, the fetal anterior abdominal wall, the fetal abdomen, the fetal urogenital system, the fetal skeleton, fetal situs, and fetal nuchal translucency. For further description of ultrasound imaging of these anatomical structures, systems, and features, see Textbook of Diagnostic Sonography, 8th Edition, which is incorporated by reference herein in its entirety.

The ultrasound patch may also be used to emit ultrasonic energy for therapeutic purposes. For example, ultrasonic energy may stimulate the baroreceptor reflex and help to reduce hypertension. In some embodiments, the ultrasound patch may be adhered to a subject's carotid sinus, the location of the carotid receptors, and be configured to emit ultrasonic energy for a period of time (e.g., minutes, hours, days, months, years) in order to stimulate the carotid baroreceptors and help to reduce hypertensions. For further description of hypertension and ultrasound see J. T. Yen, Yu Chen, M. J. Partsch and A. Covalin, "Ultrasound stimulation of carotid baroreceptors: Initial canine results," 2015 *IEEE International Ultrasonics Symposium (IUS)*, Taipei, 2015, pp. 1-4, which is incorporated by reference herein in its entirety.

In some embodiments, the ultrasound patch may be adhered adjacent to a subject's muscle and used to help heal the muscle by insonating the muscle with ultrasonic energy. For further description of muscle healing and ultrasound, see Rantanen, Jussi, et al., "Effects of therapeutic ultrasound on the regeneration of skeletal myofibers after experimental muscle injury," *The American journal of sports medicine* 27.1 (1999): 54-59; Wilkin, L. D., et al., "Influence of therapeutic ultrasound on skeletal muscle regeneration following blunt contusion," *International journal of sports medicine* 25.01 (2004): 73-77; and Markert, Chad D., et al., "Nonthermal ultrasound and exercise in skeletal muscle regeneration," *Archives of physical medicine and rehabilitation* 86.7 (2005): 1304-1310, which are incorporated by reference herein in their entireties.

In some embodiments, the ultrasound patch may be adhered adjacent to a subject's tendon and used to help heal the tendon by insonating the tendon with ultrasonic energy. For further description of tendon healing and ultrasound, see Enwemeka, Chukuka S. "The Effects of Therapeutic Ultrasound on Tendon Healing: A Biomechanical Study." *American journal of physical medicine & rehabilitation* 68.6 (1989): 283-287, which is incorporated by reference herein in its entirety.

In some embodiments, the ultrasound patch may be adhered to a subject's skin and used to help heal the skin by insonating the skin with ultrasonic energy. For further description of skin healing and ultrasound, see Young, S. R., and M. Dyson. "Effect of therapeutic ultrasound on the healing of full-thickness excised skin lesions." *Ultrasonics* 28.3 (1990): 175-180, which is incorporated by reference herein in its entirety.

In some embodiments, the ultrasound patch may be adhered adjacent to a subject's bone and used to help heal the bone (e.g., a bone fracture) by insonating the bone with ultrasonic energy. For further description of bone healing and ultrasound, see Takikawa, Satoshi, et al. "Low-intensity pulsed ultrasound initiates bone healing in rat nonunion fracture model." *Journal of ultrasound in medicine* 20.3 (2001): 197-205, which is incorporated by reference herein in its entirety.

In some embodiments, the ultrasound patch may be used to deliver HIFU-based cancer treatment (e.g., for tumors of the brain, uterus, prostate, and soft tissue). For further description of HIFU and cancer treatment, see Lin, Win-Li, et al., "Treatable domain and optimal frequency for brain tumors during ultrasound hyperthermia," *International Journal of Radiation Oncology\* Biology\* Physics* 46.1 (2000): 239-247; Mencaglia, L., "Energy focused ultrasound for the clinical treatment of uterine myoma," *Ultrasound Med. Biol.* 26 (2000): A207; Keshavarzi, Amid, et al., "Treatment of uterine leiomyosarcoma in a xenograft nude mouse model using high-intensity focused ultrasound: a potential treatment modality for recurrent pelvic disease," *Gynecologic oncology* 86.3 (2002): 344-350; Gelet, A., et al., "Transrectal high intensity focused ultrasound for the treatment of localized prostate cancer: factors influencing the outcome," *European urology* 40.2 (2001): 124-129; Uchida, Toyoaki, et al., "Transrectal high-intensity focused ultrasound for treatment of patients with stage T1b-2n0m0 localized prostate cancer: a preliminary report," *Urology* 59.3 (2002): 394-398; Visioli, A. G., et al., "Preliminary results of a phase I dose escalation clinical trial using focused ultrasound in the treatment of localised tumours," *European journal of ultrasound* 9.1 (1999): 11-18; and Wu, Feng, et al., "Pathological changes in human malignant carcinoma treated with high-intensity focused ultrasound," *Ultrasound in medicine & biology* 27.8 (2001): 1099-1106, which are incorporated by reference herein in their entireties.

In some embodiments, the ultrasound patch may be used to deliver HIFU-based therapy that includes occlusion of blood vessels. The blood vessel occlusion may help, for example, in inducing hemostasis of internal bleeding, intervening in fetal blood sharing anomalies, and confining tumor blood supply. For further description of HIFU-based therapy that includes occlusion of blood vessels, see Delon-Martin, C., et al., "Venous thrombosis generation by means of high-intensity focused ultrasound," *Ultrasound in medicine & biology* 21.1 (1995): 113-119; Hynynen, Kullervo, et al., "Potential adverse effects of high-intensity focused ultrasound exposure on blood vessels in vivo," *Ultrasound in medicine & biology* 22.2 (1996): 193-201; Vaezy, Shahram, et al., "Control of splenic bleeding by using high intensity ultrasound," *Journal of Trauma and Acute Care Surgery* 47.3 (1999): 521-525; Denbow, M. L., et al., "Preclinical development of noninvasive vascular occlusion with focused ultrasonic surgery for fetal therapy," *American journal of obstetrics and gynecology* 182.2 (2000): 387-392; and Hynynen, Kullervo, et al., "Noninvasive arterial occlusion using MRI-guided focused ultrasound," *Ultrasound in medicine & biology* 22.8 (1996): 1071-1077, which are incorporated by reference herein in their entireties.

In some embodiments, the ultrasound patch may be used to deliver HIFU-based therapy for augmentation of the body immune response. For further description of HIFU-based therapy for augmentation of the body immune response, see Burov, V. A., N. P. Dmitrieva, and O. V. Rudenko, "Nonlinear ultrasound: Breakdown of microscopic biological structures and nonthermal impact on a malignant tumor," *Doklady Biochemistry and Biophysics*. Vol. 383. No. 1. MAIK Nauka/Interperiodica, 2002, which is incorporated by reference herein in its entirety.

It should be appreciated that HIFU-based therapy may be delivered in the low-thermal regime (i.e., approximately 47 degrees Celsius or less), high-thermal regime (i.e., above 47 degrees Celsius), low-mechanical regime (i.e., just under the cavitation limit), and/or the high-mechanical regime (i.e., just above the cavitation limit). For further description of using HIFU for therapy, see Curra, Francesco P., and Lawrence A. Crum. "Therapeutic ultrasound: Surgery and drug delivery." *Acoustical Science and Technology* 24.6 (2003): 343-348, which is incorporated by reference herein in its entirety.

Examples of suitable ultrasound systems for use in HIFU are described in U.S. Pat. No. 9,327,142, which is assigned to the Assignee of the current application and which is incorporated herein by reference in its entirety. U.S. Pat. No. 8,852,103 also describes HIFU, is assigned to the Assignee of the present application, and is incorporated herein by reference in its entirety.

In some embodiments, the ultrasound patch may be used to facilitate drug delivery. For further description of drug delivery and ultrasound, see Mitragotri, Samir, Daniel Blankschtein, and Robert Langer, "Ultrasound-mediated transdermal protein delivery," *Science* 269 (1995): 850-853; Mitragotri, Samir, and Joseph Kost, "Transdermal delivery of heparin and low-molecular weight heparin using low-frequency ultrasound," *Pharmaceutical research* 18.8 (2001): 1151-1156; Tachibana, Katsuro, "Transdermal delivery of insulin to alloxan-diabetic rabbits by ultrasound exposure," *Pharmaceutical research* 9.7 (1992): 952-954; Mitragotri, Samir, and Joseph Kost, "Low-Frequency Sonophoresis: A Noninvasive Method of Drug Delivery and Diagnostics," *Biotechnology progress* 16.3 (2000): 488-492, which are incorporated by reference herein in their entireties.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

According to an aspect of the present application, a method is provided, comprising wirelessly offloading, from a wearable ultrasound device, ultrasound data sufficient for forming one or more ultrasound images therefrom. The wearable ultrasound device comprises an ultrasound patch in some embodiments. The wearable ultrasound device weighs no more than 4 lbs in some embodiments, and no more than 2 lbs in some embodiments. A volume of the wearable ultrasound device is no greater than 250 cm$^3$ in some embodiments, and no greater than 125 cm$^3$ in some embodiments, and no greater than 50 cm$^3$ in some embodiments.

The wearable ultrasound device comprises a two-dimensional array of ultrasound transducers in some embodiments. The wearable ultrasound device comprises a 1.75-dimensional array of ultrasound transducers in some embodiments.

The height of the wearable ultrasound device along a direction orthogonal to the array of ultrasound transducers is no greater than 7 cm in some embodiments. The height of the wearable ultrasound device along a direction orthogonal to the array of ultrasound transducers is no greater than 5 cm in some embodiments. The height of the wearable ultrasound device along a direction orthogonal to the array of ultrasound transducers is no greater than a dimension of the array of ultrasound transducers in some embodiments.

Wirelessly offloading the ultrasound data comprises wirelessly offloading the ultrasound data at a data rate within a range of approximately 10 megabits/second-1.73 gigabits/second in some embodiments. Wirelessly offloading the ultrasound data comprises wirelessly offloading the ultrasound data at a data rate within a range of approximately 10-866.7 megabits/second in some embodiments. Wirelessly offloading the ultrasound data sufficient for forming the one or more ultrasound images therefrom comprises wirelessly offloading the ultrasound data at a data rate within a range of approximately 10-450 megabits/second in some embodiments. Wirelessly offloading the ultrasound data comprises wirelessly offloading the ultrasound data at a data rate within a range of approximately 10-100 megabits/second in some embodiments. Wirelessly offloading the ultrasound data comprises wirelessly offloading the ultrasound data at a data rate within a range of approximately 10-72 megabits/second in some embodiments. Wirelessly offloading the ultrasound data comprises wirelessly offloading the ultrasound data at a data rate within a range of approximately 10-54 megabits/second in some embodiments. Wirelessly offloading the ultrasound data comprises wirelessly offloading the ultrasound data at a data rate within a range of approximately 10-32 megabits/second. Wirelessly offloading the ultrasound data comprises wirelessly offloading the ultrasound data using a communication platform employing an IEEE 802.11 standard.

The one or more ultrasound images include information indicative of a size or shape of a tumor in some embodiments. The one or more ultrasound images include information indicative of an elasticity of a tumor in some embodiments. The one or more ultrasound images include information indicative of a vascularity of a tumor in some embodiments. The one or more ultrasound images include information indicative of a fullness or a volume of a bladder in some embodiments. The one or more ultrasound images include information indicative of a bladder outlet obstruction in some embodiments. The one or more ultrasound images include information indicative of a pulse wave velocity or a blood pressure in some embodiments. The one or more ultrasound images include information indicative of a diameter of a blood vessel in some embodiments. The one or more ultrasound images include information indicative of a volume of a blood vessel in some embodiments. The one or more ultrasound images include information indicative of a collapsibility of a blood vessel in some embodiments. The one or more ultrasound images include information indicative of a blood flow rate through a blood vessel in some embodiments. The one or more ultrasound images include information indicative of a wall motion of a blood vessel in some embodiments. The blood vessel is an inferior vena cava in some embodiments. The one or more ultrasound images include information indicative of an intravascular volume in some embodiments. The one or more ultrasound images include information indicative of a left ventricular wall motion in some embodiments. The one or more ultrasound images include information indicative of a cardiac output in some embodiments. The one or more ultrasound images include information indicative of an ejection fraction in some embodiments. The one or more ultrasound images include information indicative of a central venous pressure in some embodiments. The one or more ultrasound images include information indicative of a peripheral blood flow rate in some embodiments. The one or more ultrasound images include information indicative of an abdominal aortic aneurysm in some embodiments. The one or more ultrasound images include information indicative of a deep vein thrombosis in some embodiments. The one or more ultrasound images include information indicative of a fetal heartbeat in some embodiments. The one or more ultrasound images include information indicative of a pregnancy in some embodiments. The one or more ultrasound images include information indicative of a follicle growth in ovaries in some embodiments. The one or more ultrasound images include information indicative of dehydration in some embodiments. The one or more ultrasound images include information indicative of a skin moisturization in some embodiments. The one or more ultrasound images include information indicative of an amniotic fluid volume in some embodiments. The one or more ultrasound images include information indicative of pneumonia in some embodiments. The one or more ultrasound images include information indicative of a pleural effusion in some embodiments. The one or more ultrasound images include information indicative of pneumothorax in some embodiments. The one or more ultrasound images include information indicative of chronic obstructive pulmonary disease (COPD) in some embodiments. The one or more ultrasound images include information indicative of a lung volume in some embodiments. The one or more ultrasound images include information indicative of an enteral feeding tube placement in some embodiments. The one or more ultrasound images include information indicative of a gastric emptying in some embodiments. The one or more ultrasound images include information indicative of indigestion in some embodiments. The one or more ultrasound images include information indicative of a kidney function in some embodiments. The one or more ultrasound images include information indicative of a renal blood flow rate in some embodiments. The one or more ultrasound images include information indicative of a needle placement during pericardiocentesis in some embodiments. The one or more ultrasound images include information indicative of a needle placement during amniocentesis in some embodiments. The one or more ultrasound images include information indicative of a vasospasm in some embodiments. The one or more ultrasound images include information indicative of a high-intensity focused ultrasound ablation in some embodiments. The one or more ultrasound images include information indicative of a drug delivery in some embodiments. The one or more ultrasound images include information indicative of a hemodialysis access in some embodiments.

According to an aspect of the present application, a method is provided, comprising insonating, for a therapeutic purpose, by a wearable ultrasound device, a subject wearing the wearable ultrasound device. The wearable ultrasound device may be any of the types described above, of any of the weights and volumes described above. The wearable ultrasound device may comprise any of the arrays of ultrasound transducers described above and may have any of the heights described above.

Insonating, for the therapeutic purpose, the subject wearing the wearable ultrasound device may comprise insonating any of a carotid baroreceptor of the subject, a muscle of the subject, a tendon of the subject, or a skin portion of the subject, a bone of the subject.

Insonating, for the therapeutic purpose, the subject wearing the wearable ultrasound device comprises delivering high-intensity focused ultrasound (HIFU)-based cancer treatment in some embodiments. Insonating, for the therapeutic purpose, the subject wearing the wearable ultrasound device comprises delivering HIFU-based therapy that includes occlusion of a blood vessel in some embodiments. Insonating, for the therapeutic purpose, the subject wearing the wearable ultrasound device comprises delivering HIFU-based therapy for augmentation of a subject's immune response in some embodiments. Insonating, for the therapeutic purpose, the subject wearing the wearable ultrasound device comprises facilitating drug delivery in some embodiments.

According to an aspect of the present application, a method is provided comprising compounding multilines of ultrasound data on an ultrasound device configured to collect the ultrasound data. In some embodiments, compounding the multilines of the ultrasound data comprises: collecting, by the ultrasound device, N first multilines of the ultrasound data following a first ultrasound transmit event; collecting, by the ultrasound device, N second multilines of the ultrasound data following a second ultrasound transmit event that is subsequent to the first ultrasound transmit event; and compounding, on the ultrasound device, N–p of the first multilines and N–p of the second multilines, wherein p is a pitch factor of the first and second multilines of ultrasound data and is less than N. Compounding comprises incoherent compounding in some embodiments. Compounding comprises coherent compounding in some embodiments. The method further comprises offloading from the ultrasound device, following the first ultrasound transmit event, p multilines of the first multilines in some embodiments. The method further comprises truncating the p multilines of the first multilines to 12 bits prior to offloading in some embodiments. The method further comprises truncating the p multilines of the first multilines to 10 bits prior to offloading in some embodiments. Offloading the p multilines of the first multilines comprises wirelessly offloading the p multilines in some embodiments.

Offloading the p multilines of the first multilines comprises wirelessly offloading the p multilines at a data rate within a range of approximately 10 megabits/second-1.73 gigabits/second in some embodiments. Offloading the p multilines of the first multilines comprises wirelessly offloading the p multilines at a data rate within a range of approximately 10-866.7 megabits/second in some embodiments. Offloading the p multilines of the first multilines comprises wirelessly offloading the p multilines at a data rate within a range of approximately 10-450 megabits/second in some embodiments. Offloading the p multilines of the first multilines comprises wirelessly offloading the p multilines at a data rate within a range of approximately 10-100 megabits/second in some embodiments. Offloading the p multilines of the first multilines comprises wirelessly offloading the p multilines at a data rate within a range of approximately 10-72 megabits/second in some embodiments. Offloading the p multilines of the first multilines comprises wirelessly offloading the p multilines at a data rate within a range of approximately 10-54 megabits/second in some embodiments. Offloading the p multilines of the first multilines comprises wirelessly offloading the p multilines at a data rate within a range of approximately 10-32 megabits/second in some embodiments. Offloading the p multilines of the first multilines comprises wirelessly offloading the p multilines using a communication platform employing an IEEE 802.11 standard in some embodiments.

The p multilines of the first multilines do not overlap with any of the second multilines in some embodiments. The N–p multilines of the first multilines and the N–p multilines of the second multilines overlap in some embodiments. The method further comprises offloading from the ultrasound device, following the second ultrasound transmit event, p multilines of the first multilines compounded with p multilines of the second multilines in some embodiments. The method further comprises truncating the p multilines of the first multilines compounded with the p multilines of the second multilines to 12 bits prior to offloading, in some embodiments. The method further comprises truncating the p multilines of the first multilines compounded with the p multilines of the second multilines to 10 bits prior to offloading in some embodiments. Offloading the p multilines of the first multilines compounded with the p multilines of the second multilines comprises wirelessly offloading the p multilines in some embodiments. Wirelessly offloading the p multilines of the first multilines compounded with the p multilines of the second multilines comprises wirelessly offloading the p multilines at a data rate within a range of approximately 10 megabits/second-1.73 gigabits/second in some embodiments. Wirelessly offloading the p multilines of the first multilines compounded with the p multilines of the second multilines comprises wirelessly offloading the p multilines at a data rate within a range of approximately 10-866.7 megabits/second in some embodiments. Wirelessly offloading the p multilines of the first multilines compounded with the p multilines of the second multilines comprises wirelessly offloading the p multilines at a data rate within a range of approximately 10-450 megabits/second in some embodiments. Wirelessly offloading the p multilines of the first multilines compounded with the p multilines of the second multilines comprises wirelessly offloading the p multilines at a data rate within a range of approximately 10-100 megabits/second in some embodiments. Wirelessly offloading the p multilines of the first multilines compounded with the p multilines of the second multilines comprises wirelessly offloading the p multilines at a data rate within a range of approximately 10-72 megabits/second in some embodiments. Wirelessly offloading the p multilines of the first multilines compounded with the p multilines of the second multilines comprises wirelessly offloading the p multilines at a data rate within a range of approximately 10-54 megabits/second in some embodiments. Wirelessly offloading the p multilines of the first multilines compounded with the p multilines of the second multilines comprises wirelessly offloading the p multilines at a data rate within a range of approximately 10-32 megabits/second in some embodiments. Wirelessly offloading the p multilines of the first multilines compounded with the p multilines of the second multilines comprises wirelessly offloading the p multilines using a communication platform employing an IEEE 802.11 standard in some embodiments. N is between 2-32 and p is between 1-8 in some embodiments. The ultrasound device comprises digital circuitry having configurable bit depth in some embodiments. Compounding the multilines of the ultrasound data on the ultrasound device comprises compounding the multilines of the ultrasound data on a field-programmable gate array (FPGA) on the ultrasound device in some embodiments.

Compounding the multilines of the ultrasound data on the ultrasound device comprises compounding the multilines of the ultrasound data on an application-specific integrated circuit (ASIC) on the ultrasound device in some embodiments. Compounding the multilines of the ultrasound data on the ultrasound device comprises compounding the multilines of the ultrasound data on an ultrasound-on-a-chip on the ultrasound device in some embodiments. The ultrasound device comprises a wearable ultrasound device in some embodiments. The ultrasound device may comprise an ultrasound patch of any of the weights and sizes described previously. The ultrasound device may include of the arrays of ultrasound transducers described previously, with any of the heights previously described. The ultrasound device comprises between approximately 5 kilobytes and 20 megabytes of memory in some embodiments.

According to an aspect of the present application, a method for collecting ultrasound data on an ultrasound device is provided. The ultrasound device has a memory buffer. The method comprises: collecting N multilines of ultrasound data following an ultrasound transmit event; and updating data at addresses 1 to N of the memory buffer by: compounding data at addresses ((p×i) modulo N)+1 to ((p×i+N−p−1) modulo N)+1 of the memory buffer with multilines 1 to N−p of the N multilines; and overwriting data at addresses ((p×i+N−p) modulo N)+1 to ((p×i+N−1) modulo N)+1 of the memory buffer with multilines N−p+1 to N of the N multilines, wherein: p comprises a pitch factor of multilines collected by the ultrasound device following successive ultrasound transmit events; and i comprises a counter variable. Compounding comprises incoherent compounding in some embodiments. Compounding comprises coherent compounding in some embodiments.

The method further comprises: prior to updating the data at the addresses 1 to N of the memory buffer, storing at the addresses 1 to N of the memory buffer multilines of ultrasound data collected following one or more ultrasound transmit events prior to the ultrasound transmit event in some embodiments. The method further comprises offloading data at addresses ((p×i) modulo N)+1 to ((p×i+p−1) modulo N)+1 of the memory buffer from the ultrasound device in some embodiments. The method further comprises truncating the data at addresses 1 to p of the memory buffer to 12 bits prior to offloading in some embodiments. The method further comprises truncating the data at addresses 1 to p of the memory buffer to 10 bits prior to offloading in some embodiments.

Offloading the data at addresses 1 to p of the memory buffer comprises wirelessly offloading the data at addresses 1 to p of the memory buffer in some embodiments. Wirelessly offloading the data at addresses 1 to p of the memory buffer comprises wirelessly offloading the data at addresses 1 to p of the memory buffer at a data rate within a range of approximately 10 megabits/second-1.73 gigabits/second in some embodiments. Wirelessly offloading the data at addresses 1 to p of the memory buffer comprises wirelessly offloading the data at addresses 1 to p of the memory buffer at a data rate within a range of approximately 10-866.7 megabits/second in some embodiments. Wirelessly offloading the data at addresses 1 to p of the memory buffer comprises wirelessly offloading the data at addresses 1 to p of the memory buffer at a data rate within a range of approximately 10-450 megabits/second in some embodiments. Wirelessly offloading the data at addresses 1 to p of the memory buffer comprises wirelessly offloading the data at addresses 1 to p of the memory buffer at a data rate within a range of approximately 10-100 megabits/second in some embodiments. Wirelessly offloading the data at addresses 1 to p of the memory buffer comprises wirelessly offloading the data at addresses 1 to p of the memory buffer at a data rate within a range of approximately 10-72 megabits/second in some embodiments. Wirelessly offloading the data at addresses 1 to p of the memory buffer comprises wirelessly offloading the data at addresses 1 to p of the memory buffer at a data rate within a range of approximately 10-54 megabits/second in some embodiments. Wirelessly offloading the data at addresses 1 to p of the memory buffer comprises wirelessly offloading the data at addresses 1 to p of the memory buffer at a data rate within a range of approximately 10-32 megabits/second in some embodiments. Wirelessly offloading the data at addresses 1 to p of the memory buffer comprises wirelessly offloading the data at addresses 1 to p of the memory buffer using a communication platform employing an IEEE 802.11 standard in some embodiments.

The method further comprises incrementing i by 1 after offloading the data at addresses 1 to p of the memory buffer in some embodiments. N is between 2-32 and p is between 1-8 in some embodiments.

The ultrasound device comprises digital circuitry having configurable bit depth in some embodiments. The ultrasound device may be a wearable ultrasound patch, and may have any of the weights or sizes previously described, including any of the volumes and heights previously described. The ultrasound device may comprise an array of any of the types previously described, with any of the heights previously described.

The ultrasound device comprises between approximately 5 kilobytes and 20 megabytes of memory in some embodiments.

According to an aspect of the present application, a method for collecting ultrasound data on an ultrasound device is provided. The ultrasound device has a memory buffer. The method comprises collecting N multilines of ultrasound data following an ultrasound transmit event; and updating data at addresses 1 to N of the memory buffer by: compounding data at addresses 1 to N−p of the memory buffer with multilines 1 to N−p of the N multilines; and overwriting data at addresses N−p+1 to N of the memory buffer with multilines N−p+1 to N of the N multilines, wherein p comprises a pitch factor of multilines collected by the ultrasound device following successive ultrasound transmit events. Compounding comprises incoherent compounding in some embodiments. Compounding comprises coherent compounding in some embodiments.

The method further comprises prior to updating the data at the addresses 1 to N of the memory buffer, storing at the addresses 1 to N of the memory buffer multilines of ultrasound data collected following one or more ultrasound transmit events prior to the ultrasound transmit event in some embodiments. The method further comprises offloading the data at addresses 1 to p of the memory buffer from the ultrasound device in some embodiments. The method further comprises truncating the data at addresses 1 to p of the memory buffer to 12 bits prior to offloading in some embodiments. The method further comprises truncating the data at addresses 1 to p of the memory buffer to 10 bits prior to offloading in some embodiments.

Offloading the data at addresses 1 to p of the memory buffer comprises wirelessly offloading the data at addresses 1 to p of the memory buffer in some embodiments. Wirelessly offloading the data at addresses 1 to p of the memory buffer comprises wirelessly offloading the data at addresses 1 to p of the memory buffer at any of the data rates previously described. Wirelessly offloading the data at addresses 1 to p of the memory buffer comprises wirelessly offloading the data at addresses 1 to p of the memory buffer using a communication platform employing an IEEE 802.11 standard in some embodiments. The method further comprises moving the data at addresses p+1 to N of the memory buffer to addresses 1 to N−p of the memory buffer in some embodiments. N is between 2-32 and p is between 1-8 in some embodiments.

The ultrasound device comprises digital circuitry having configurable bit depth in some embodiments. The ultrasound device is any of the types previously described herein, with any of the sizes, weights, and volumes previously described.

According to an aspect of the present application, an apparatus is provided comprising an ultrasound device configured to collect ultrasound data and compound multilines of the ultrasound data. The ultrasound device is configured in some embodiments, when compounding the multilines of the ultrasound data, to: collect N first multilines of the ultrasound data following a first ultrasound transmit event; collect N second multilines of the ultrasound data following a second ultrasound transmit event that is subsequent to the first ultrasound transmit event; and compound N−p of the first multilines and N−p of the second multilines, wherein p is a pitch factor of the first and second multilines of ultrasound data and is less than N. Compounding comprises incoherent compounding in some embodiments. Compounding comprises coherent compounding in some embodiments. N is between 2-32 and p is between 1-8 in some embodiments. The ultrasound device is further configured to offload, following the first ultrasound transmit event, p multilines of the first multilines in some embodiments. The ultrasound device is further configured to truncate the p multilines of the first multilines to 12 bits prior to offloading in some embodiments. The ultrasound device is further configured to truncate the p multilines of the first multilines to 10 bits prior to offloading in some embodiments.

Offloading the p multilines of the first multilines comprises wirelessly offloading the p multilines in some embodiments. The ultrasound device is configured, when wirelessly offloading the p multilines of the first multilines, to wirelessly offload the p multilines at a data rate within a range of approximately 10 megabits/second-1.73 gigabits/second, within a range of approximately 10-866.7 megabits/second, within a range of approximately 10-450 megabits/second, within a range of approximately 10-100 megabits/second, within a range of approximately 10-72 megabits/second, within a range of approximately 10-54 megabits/second, within a range of approximately 10-32 megabits/second, or within any other suitable range.

The ultrasound device is configured, when wirelessly offloading the p multilines of the first multilines, to wirelessly offload the p multilines using a communication platform employing an IEEE 802.11 standard in some embodiments.

The p multilines of the first multilines do not overlap with any of the second multilines in some embodiments. The N−p multilines of the first multilines and the N−p multilines of the second multilines overlap in some embodiments. The ultrasound device is further configured to offload, following the second ultrasound transmit event, p multilines of the first multilines compounded with p multilines of the second multilines in some embodiments. The ultrasound device is further configured to truncate the p multilines of the first multilines compounded with the p multilines of the second multilines to 12 bits prior to offloading in some embodiments. The ultrasound device is further configured to truncate the p multilines of the first multilines compounded with the p multilines of the second multilines to 10 bits prior to offloading in some embodiments. Offloading the p multilines of the first multilines compounded with the p multilines of the second multilines comprises wirelessly offloading the p multilines in some embodiments. The ultrasound device is configured, when wirelessly offloading the p multilines of the first multilines compounded with the p multilines of the second multilines, to wirelessly offload the p multilines at any of the data rates described previously herein.

The ultrasound device is configured in some embodiments, when wirelessly offloading the p multilines of the first multilines compounded with the p multilines of the second multilines, to wirelessly offload the p multilines using a communication platform employing an IEEE 802.11 standard. The ultrasound device is configured to compound the multilines of ultrasound data on a field-programmable gate array (FPGA) on the ultrasound device in some embodiments.

The ultrasound device is configured to compound the multilines of ultrasound data on an application-specific circuit (ASIC) on the ultrasound device in some embodiments. The ultrasound device is configured to compound the multilines of ultrasound data on an ultrasound-on-a-chip on the ultrasound device in some embodiments. The ultrasound device comprises digital circuitry having configurable bit depth in some embodiments.

The ultrasound device comprises a wearable ultrasound device. The ultrasound device may be any of the types described previously herein, having any of the weights and sizes, including heights and volumes. The wearable ultrasound device may comprise any of the arrays described previously herein, having any of the described sizes. The ultrasound device comprises between approximately 5 kilobytes and 20 megabytes of memory in some embodiments.

According to an aspect of the present application, an apparatus comprising an ultrasound device is provided, the ultrasound device having a memory buffer. The ultrasound device is configured to: collect N multilines of ultrasound data following an ultrasound transmit event; and update data at addresses 1 to N of the memory buffer by: compounding data at addresses $((p \times i) \text{ modulo } N)+1$ to $((p \times i+N-p-1) \text{ modulo } N)+1$ of the memory buffer with multilines 1 to N−p of the N multilines; and overwriting data at addresses $((p \times i+N-p) \text{ modulo } N)+1$ to $((p \times i+N-1) \text{ modulo } N)+1$ of the memory buffer with multilines N−p+1 to N of the N multilines, wherein: p comprises a pitch factor of multilines collected by the ultrasound device following successive ultrasound transmit events; and i comprises a counter variable.

Compounding comprises incoherent compounding in some embodiments. Compounding comprises coherent compounding in some embodiments.

The ultrasound device is configured in some embodiments to store, prior to updating the data at the addresses 1 to N of the memory buffer, multilines of ultrasound data collected following one or more ultrasound transmit events prior to the ultrasound transmit event at the addresses 1 to N of the memory buffer. The ultrasound device is further configured in some embodiments to offload data at addresses $((p \times i) \text{ modulo } N)+1$ to $((p \times i+p-1) \text{ modulo } N)+1$ of the memory buffer from the ultrasound device. The ultrasound device is further configured in some embodiments to truncate the data at addresses $((p \times i) \text{ modulo } N)+1$ to $((p \times i+p-1) \text{ modulo } N)+1$ of the memory buffer to 12 bits prior to offloading. The ultrasound device is further configured in some embodiments to truncate the data at addresses $((p \times i) \text{ modulo } N)+1$ to $((p \times i+p-1) \text{ modulo } N)+1$ of the memory buffer to 10 bits prior to offloading. The ultrasound device is configured in some embodiments, when offloading the data at addresses $((p \times i) \text{ modulo } N)+1$ to $((p \times i+p-1) \text{ modulo } N)+1$, to wirelessly offload the data at addresses $((p \times i) \text{ modulo } N)+1$ to $((p \times i+p-1) \text{ modulo } N)+1$ of the memory buffer. The ultrasound device is configured in some embodiments, when wirelessly offloading the data at addresses $((p \times i) \text{ modulo } N)+1$ to $((p \times i+p-1) \text{ modulo } N)+1$ of the memory buffer, to wirelessly offload the data at addresses $((p \times i) \text{ modulo } N)+1$ to $((p \times i+p-1) \text{ modulo } N)+1$ of the memory buffer at any of the data rates described previously herein.

The ultrasound device is configured in some embodiments, when wirelessly offloading the data at addresses ((p×i) modulo N)+1 to ((p×i+p−1) modulo N)+1 of the memory buffer, to wirelessly offload the data at addresses ((p×i) modulo N)+1 to ((p×i+p−1) modulo N)+1 of the memory buffer using a communication platform employing an IEEE 802.11 standard.

The ultrasound device is further configured in some embodiments to increment i by 1 after offloading the data at addresses ((p×i) modulo N)+1 to ((p×i+p−1) modulo N)+1 of the memory buffer. N is between 2-32 and p is between 1-8 in some embodiments. The ultrasound device comprises digital circuitry having configurable bit depth in some embodiments. The ultrasound device is any of the types described previously herein, having any of the weights and sizes, including heights and volumes. The ultrasound device may comprise any of the types of arrays described herein, having any of the sizes (including heights). The ultrasound device comprises between approximately 5 kilobytes and 20 megabytes of memory in some embodiments.

According to an aspect of the present application, an apparatus is provided comprising an ultrasound device. The ultrasound device has a memory buffer and is configured to: collect N multilines of ultrasound data following an ultrasound transmit event; and update data at addresses 1 to N of the memory buffer by: compounding data at addresses 1 to N−p of the memory buffer with multilines 1 to N−p of the N multilines; and overwriting data at addresses N−p+1 to N of the memory buffer with multilines N−p+1 to N of the N multilines, wherein p comprises a pitch factor of multilines collected by the ultrasound device following successive ultrasound transmit events. The compounding comprises incoherent compounding in some embodiments. The compounding comprises coherent compounding in some embodiments.

The ultrasound device is configured to store, prior to updating the data at the addresses 1 to N of the memory buffer, multilines of ultrasound data collected following one or more ultrasound transmit events prior to the ultrasound transmit event at the addresses 1 to N of the memory buffer in some embodiments. The ultrasound device is further configured to offload the data at addresses 1 to p of the memory buffer from the ultrasound device in some embodiments. The ultrasound device is further configured to truncate the data at addresses 1 to p of the memory buffer to 12 bits prior to offloading in some embodiments. The ultrasound device is further configured to truncate the data at addresses 1 to p of the memory buffer to 10 bits prior to offloading in some embodiments. The ultrasound device is configured, when offloading the data at addresses 1 to p, to wirelessly offload the data at addresses 1 to p of the memory buffer in some embodiments. The ultrasound device is configured, when wirelessly offloading the data at addresses 1 to p of the memory buffer, to wirelessly offload the data at addresses 1 to p of the memory buffer at a data rate within a range of approximately 10 megabits/second-1.73 gigabits/second in some embodiments.

The ultrasound device is configured, when wirelessly offloading the data at addresses 1 to p of the memory buffer, to wirelessly offload the data at addresses 1 to p of the memory buffer at a data rate within a range of approximately 10-866.7 megabits/second in some embodiments. The ultrasound device is configured, when wirelessly offloading the data at addresses 1 to p of the memory buffer, to wirelessly offload the data at addresses 1 to p of the memory buffer at a data rate within a range of approximately 10-450 megabits/second in some embodiments. The ultrasound device is configured, when wirelessly offloading the data at addresses 1 to p of the memory buffer, to wirelessly offload the data at addresses 1 to p of the memory buffer at a data rate within a range of approximately 10-100 megabits/second in some embodiments. The ultrasound device is configured, when wirelessly offloading the data at addresses 1 to p of the memory buffer, to wirelessly offload the data at addresses 1 to p of the memory buffer at a data rate within a range of approximately 10-72 megabits/second in some embodiments. The ultrasound device is configured, when wirelessly offloading the data at addresses 1 to p of the memory buffer, to wirelessly offload the data at addresses 1 to p of the memory buffer at a data rate within a range of approximately 10-54 megabits/second in some embodiments. The ultrasound device is configured, when wirelessly offloading the data at addresses 1 to p of the memory buffer, to wirelessly offload the data at addresses 1 to p of the memory buffer at a data rate within a range of approximately 10-32 megabits/second in some embodiments. The ultrasound device is configured, when wirelessly offloading the data at addresses 1 to p of the memory buffer, to wirelessly offload the data at addresses 1 to p of the memory buffer using a communication platform employing an IEEE 802.11 standard in some embodiments. The ultrasound device is further configured to move the data at addresses p+1 to N of the memory buffer to addresses 1 to N−p of the memory buffer in some embodiments. N is between 2-32 and p is between 1-8 in some embodiments.

The ultrasound device comprises digital circuitry having configurable bit depth in some embodiments. The ultrasound device comprises a wearable ultrasound device in some embodiments. The wearable ultrasound device comprises an ultrasound patch in some embodiments. The weights and volumes may be any of those described above. The wearable ultrasound device may comprise any of the arrays of ultrasound transducers described above and may have any of the heights described above.

According to an aspect of the present application, an apparatus is provided comprising an ultrasound device. The ultrasound device comprises a first group of ultrasound transducers; a second group of ultrasound transducers; a first transmit/receive circuit electrically coupled to the first group of ultrasound transducers; and a second transmit/receive circuit electrically coupled to the second group of ultrasound transducers. The first group of ultrasound transducers comprises a greater number of ultrasound transducers than the second group of ultrasound transducers. The first group of ultrasound transducers and the second group of ultrasound transducers are disposed in a single column of an array of ultrasound transducers in some embodiments. The single column is disposed along an elevational direction of the array of ultrasound transducers in some embodiments. The first group of ultrasound transducers is disposed further towards to the center of the column than the second group of ultrasound transducers in some embodiments. Each group of ultrasound transducers in the column that is coupled to a single transmit/receive circuit contains fewer or an equal number of ultrasound transducers than every other group of ultrasound transducers that is coupled to a single transmit/receive and is disposed further towards the center of the column. The array of ultrasound transducers comprises a 1.75-dimensional array in some embodiments. The first transmit/receive circuit and the second transmit/receive circuit each comprise a receive amplifier, a pulser, and a switch in some embodiments. The column comprises 32 ultrasound transducers grouped into 11 groups of ultrasound transducers each electrically coupled to a single transmit/receive circuit in some embodiments. The ultrasound device comprises a wearable ultrasound device in some embodiments. The ultrasound device may be any of the types described above, of any of the weights and volumes described above.

The wearable ultrasound device comprises a two-dimensional array of ultrasound transducers in some embodiments. The wearable ultrasound device comprises a 1.75-dimensional array of ultrasound transducers in some embodiments. A height of the wearable ultrasound device along a direction orthogonal to the array of ultrasound transducers is no greater than 7 cm in some embodiments. A height of the wearable ultrasound device along a direction orthogonal to the array of ultrasound transducers is no greater than 5 cm in some embodiments. A height of the wearable ultrasound device along a direction orthogonal to the array of ultrasound transducers is no greater than a dimension of the array of ultrasound transducers in some embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound probe having a data memory with a first set of addresses and a second set of addresses and configured to collect ultrasound data and compound multilines of the ultrasound data, wherein the ultrasound device is configured, when compounding the multilines of the ultrasound data, to:
   collect N first multilines of the ultrasound data following a first ultrasound transmit event and store the N first multines with the memory;
   offload, following the first ultrasound transmit event, p multilines of the first multilines from the first set of addresses in the memory,
   collect N second multilines of the ultrasound data following a second ultrasound transmit event that is subsequent to the first ultrasound transmit event;
   compound N-p of the first multilines that are stored at the second set of addresses in the memory with N-p of the second multilines, such that the compounded N-p of the first multilines and the N-p of the second multilines are stored at the second set of addresses in the memory, and wherein p is a number of multilines offset between the first and second multilines of ultrasound data and is less than N.

2. The apparatus of claim 1, wherein compounding comprises incoherent compounding.

3. The apparatus of claim 1, wherein compounding comprises coherent compounding.

4. The apparatus of claim 1, wherein N is between 2-32 and p is between 1-8.

5. The apparatus of claim 1, wherein the ultrasound device is further configured to truncate the p multilines of the first multilines to 12 bits prior to offloading.

6. The apparatus of claim 1, wherein the ultrasound device is further configured to truncate the p multilines of the first multilines to 10 bits prior to offloading.

7. The apparatus of claim 1, wherein offloading the p multilines of the first multilines comprises wirelessly offloading the p multilines.

8. The apparatus of claim 7, wherein the ultrasound device is configured, when wirelessly offloading the p multilines of the first multilines, to wirelessly offload the p multilines at a data rate within a range of approximately 10 megabits/second-1.73 gigabits/second.

9. The apparatus of claim 7, wherein the ultrasound device is configured, when wirelessly offloading the p multilines of the first multilines, to wirelessly offload the p multilines at a data rate within a range of approximately 10-866.7 megabits/second.

10. The apparatus of claim 7, wherein the ultrasound device is configured, when wirelessly offloading the p multilines of the first multilines, to wirelessly offload the p multilines at a data rate within a range of approximately 10-450 megabits/second.

11. The apparatus of claim 7, wherein the ultrasound device is configured, when wirelessly offloading the p multilines of the first multilines, to wirelessly offload the p multilines at a data rate within a range of approximately 10-100 megabits/second.

12. The apparatus of claim 7, wherein the ultrasound device is configured, when wirelessly offloading the p multilines of the first multilines, to wirelessly offload the p multilines at a data rate within a range of approximately 10-72 megabits/second.

13. The apparatus of claim 7, wherein the ultrasound device is configured, when wirelessly offloading the p multilines of the first multilines, to wirelessly offload the p multilines at a data rate within a range of approximately 10-54 megabits/second.

14. The apparatus of claim 7, wherein the ultrasound device is configured, when wirelessly offloading the p multilines of the first multilines, to wirelessly offload the p multilines at a data rate within a range of approximately 10-32 megabits/second.

15. The apparatus of claim 7, wherein the ultrasound device is configured, when wirelessly offloading the p multilines of the first multilines, to wirelessly offload the p multilines using a communication platform employing an IEEE 802.11 standard.

16. The apparatus of claim 1, wherein the p multilines of the first multilines do not overlap with any of the second multilines.

17. The apparatus of claim 1, wherein the N-p multilines of the first multilines and the N-p multilines of the second multilines overlap.

18. The apparatus of claim 1, wherein the ultrasound device is further configured to offload, following the second ultrasound transmit event, p multilines of the first multilines compounded with p multilines of the second multilines.

19. The apparatus of claim 1, wherein the ultrasound device is configured to compound the multilines of ultrasound data on a field-programmable gate array (FPGA) on the ultrasound device.

20. The apparatus of claim 1, wherein the ultrasound device is configured to compound the multilines of ultrasound data on an application-specific circuit (ASIC) on the ultrasound device.

21. The apparatus of claim 1, wherein the ultrasound device is configured to compound the multilines of ultrasound data on an ultrasound-on-a-chip on the ultrasound device.

22. The apparatus of claim 1, wherein the ultrasound device comprises digital circuitry having configurable bit depth.

23. A wearable ultrasound patch having a data memory with a first set of addresses and a second set of addresses and configured to collect ultrasound data and compound multilines of the ultrasound data, wherein the ultrasound device is configured, when compounding the multilines of the ultrasound data, to:

collect N first multilines of the ultrasound data following a first ultrasound transmit event and store the N first multines with the memory;

offload, following the first ultrasound transmit event, p multilines of the first multilines from the first set of addresses in the memory, collect N second multilines of the ultrasound data following a second ultrasound transmit event that is subsequent to the first ultrasound transmit event;

compound N-p of the first multilines that are stored at the second set of addresses in the memory with N-p of the second multilines, such that the compounded N-p of the first multilines and the N-p of the second multilines are stored at the second set of addresses in the memory, and wherein p is a number of multilines offset between the first and second multilines of ultrasound data and is less than N.

* * * * *